US007858738B2

(12) United States Patent
Mozes

(10) Patent No.: US 7,858,738 B2
(45) Date of Patent: Dec. 28, 2010

(54) SYNTHETIC HUMAN PEPTIDES AND PHARMACEUTICAL COMPOSITIONS COMPRISING THEM FOR THE TREATMENT OF SYSTEMIC LUPUS ERYTHEMATOSUS

(75) Inventor: Edna Mozes, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 213 days.

(21) Appl. No.: 11/894,472

(22) Filed: Aug. 20, 2007

(65) Prior Publication Data

US 2008/0119390 A1 May 22, 2008

Related U.S. Application Data

(63) Continuation of application No. 10/468,924, filed as application No. PCT/IL02/00148 on Feb. 26, 2002, now abandoned.

(30) Foreign Application Priority Data

Feb. 26, 2001 (IL) .................................. 141647

(51) Int. Cl.
| A61K 38/00 | (2006.01) |
| A61K 38/04 | (2006.01) |
| A61K 38/16 | (2006.01) |
| C07K 7/00 | (2006.01) |
| C07K 14/00 | (2006.01) |

(52) U.S. Cl. ........................... 530/300; 530/326; 514/2; 514/13

(58) Field of Classification Search ...................... None
See application file for complete search history.

(56) References Cited

U.S. PATENT DOCUMENTS

| 4,656,158 | A | | 4/1987 | Matsuo et al. |
| 5,126,249 | A | | 6/1992 | Becker et al. |
| 5,134,127 | A | | 7/1992 | Stella et al. |
| 5,356,779 | A | * | 10/1994 | Mozes et al. ............... 435/7.24 |
| 5,376,645 | A | | 12/1994 | Stella et al. |
| 5,646,131 | A | | 7/1997 | Badwan et al. |
| 5,730,969 | A | | 3/1998 | Hora et al. |
| 5,997,856 | A | | 12/1999 | Hora et al. |
| 6,066,621 | A | * | 5/2000 | Sela et al. ...................... 514/15 |
| 6,228,363 | B1 | | 5/2001 | Naparstek |
| 6,407,079 | B1 | | 6/2002 | Muller et al. |
| 6,613,536 | B1 | | 9/2003 | Mozes et al. |
| 7,294,687 | B2 | | 11/2007 | Cohen-Vered et al. |
| 2002/0054872 | A1 | | 5/2002 | Naparstek |
| 2003/0105000 | A1 | * | 6/2003 | Pero et al. ...................... 514/12 |
| 2004/0127408 | A1 | | 7/2004 | Mozes et al. |
| 2004/0180059 | A1 | | 9/2004 | Cohen-Vered et al. |
| 2005/0008634 | A1 | | 1/2005 | Cohen-Vered et al. |

FOREIGN PATENT DOCUMENTS

EP 0495049 7/1992

| WO | 9630057 | 10/1996 |
| WO | 9931066 | 6/1999 |
| WO | 02067848 | 9/2002 |
| WO | 2004064787 | 8/2004 |
| WO | 2004064788 | 8/2004 |

OTHER PUBLICATIONS

Ibragimova and Eade (Biophysical Journal, Oct. 1999, vol. 77, pp. 2191-2198).*
Burgess et al (J of Cell Bio. 111:2129-2138, 1990).*
Scott et al (Nature Genetics, 1999, 21:440-443).*
Berg et al. (Biochemistry, 5th ed., W. H. Freeman and Co. 2002, section 3.2).*
Lazar et al (Molecular and Cellular Biology, 1988, 8:1247-1252).*
Anderson, B.D. et al. (1996), "The Practice of Medicinal Chemistry" *Academic Press* 34:739-754.
Audibert et al. (1981) Active antitoxic immunization by a diphtheria toxin synthetic oligopeptide. *Nature*, 289:593-4.
Axelrod, O. and Mozes, E. (1986) Analysis of the biological functions and fine specificity of (T,G)-A—L specific T cell clones. *Immunobiology*, 172:99-109.
Bombardier C. et al. (1992) Derivation of the SLEDAI. A disease activity index for lupus patients. The Committee on Prognosis Studies in SLE. *Arthritis Rheum.*, 35:630-40.
Brosch N. et al. (2000) A Peptide Based on the Sequence of the CDR3 of a Murine Anti-DNA mAb is a Better Modulator of Experimental SLE than its Single Amino Acid-Substituted Analogs. *Cellular Immunology*, 205:52-61.
Brosch N. et al. (2000) Characterization and Role in Experimental Systemic Lupus Erythematosus of T-cell Lines Specific to Peptides Based on Complementarity-Determining Region-1 and Complementarity-Determining Region-3 of a Pathogenic Anti-DNA Monoclonal Antibody. *Immunology* 99:257-264.
Conlon, P.J. (1983) A rapid biologic assay for the detection of interleukin 1. *J. Immunol.*, 134:1280-2.
Dayan M. et al. (2000) Immune response of SLE patients to peptides based on the complementarity determining regions of a pathogenic anti-DNA monoclonal antibody. *J. Clin. Immunol.*,20(3):187-94.
Dean G.S. et al. (2000) Cytokines and systemic lupus erythematosus. *Ann. Rheum. Dis.*, 59:243-51.
Eilat, E., et al. (2000) Prevention of systemic lupus erythematosus-like disease in (NZBxNZW)F1 mice by treating with CDR1- and CDR3- based peptides of pathogenic autoantibody. *J. Clin. Immunol.*, 20:268-78.
U.S. Appl. No. 10/758,572, filed Jan. 14, 2004.
U.S. Appl. No. 11/985,068, filed Jan. 14, 2004.
Eilat, E., et al. (2001) The mechanism by which a peptide based on complementarity determining region-1 of pathogenic anti-DNA antibody ameliorates experimental SLE. *Proc. Natl. Acad. Sci. U.S.A.*, 98: 1148-53.

(Continued)

*Primary Examiner*—Peter J Reddig
(74) *Attorney, Agent, or Firm*—John P. White; Cooper & Dunham LLP

(57) ABSTRACT

Synthetic peptides of at least 12 and at most 30 amino acid residues comprising a sequence consisting of, or found within, a complementarity-determining region (CDR) found in the heavy or light chain of the human anti-DNA 16/6Id monoclonal antibody, or a sequence obtained by replacement and/or deletion and/or addition of one or more amino residues to said sequence, and salts, chemical derivatives and polymers of said peptides can be used for immunomodulation of systemic lupus erythematosus-associated responses.

22 Claims, 33 Drawing Sheets

OTHER PUBLICATIONS

Fricke, H. et al. (1991) Idiotype specific T-cell lines inducing experimental systemic lupus erythematosus in mice. *Immunology*, 73:421-7.

Fricke, H. et al. (1990) Induction of experimental systemic lupus erythematosus in mice by immunization with a monoclonal anti-La autoantibody. *Int. Immunol.*, 2:225-30.

Gearing, A.J.H. et al. (1994) Processing of tumor necrosis factor-alpha precursor by metalloproteinases. *Nature*, 370:555-7.

Gijbels, K. et al. (1992) Gelatinase in the cerebrospinal fluid of patients with multiple sclerosis and other inflammatory neurological disorders. *J. Neuroimmunol.*, 41:29-34.

Goetzl, E.J. et al. (1996) Matrix metalloproteinases in immunity. *J. Immunol.*, 156:1-4.

Guedez, L. et al. (1996) The role of metalloproteinases and their inhibitors in hematological disorders. *Crit. Rev. Oncog.*, 7:205-25.

Hay, E.M. et al. (1993) The BILAG index: a reliable and valid instrument for measuring clinical disease activity in systemic lupus erythematosus. *Q. J. Med.*, 86:447-58.

Isenberg, D.A., et al. (1984) Anti-DNA antibody idiotypes in systemic lupus erythematosus. *Lancet*, 2(8400):417-22.

Isenberg, D.A., et al. (1985) Detection of cross-reactive anti-DNA antibody idiotypes on renal tissue-bound immunoglobulins from lupus patients. *J. Clin. Invest.*, 76(1):287-94.

Katchalski, E. et al. (1955) Molecular weight distribution of linear and multichain polyamino acids. Statistical analysis. *J. Am. Chem. Soc.*, 77:6175-82.

Kotajima, L., et al., (1998) Increased levels of matrix metalloproteinase-3 in sera from patients with active lupus nephritis. *Clin. Exp. Rheumatol.*, 16(4):409-15.

Mendlovic, S. et al. (1988) Induction of a systemic lupus erythematosus-like disease in mice by a common human anti-DNA idiotype. *Proc. Natl. Acad. Sci. U.S.A.*, 85:2260-4.

Mendlovic, S. et al. (1989) The role of anti-idiotypic antibodies in the induction of experimental systemic lupus erythematosus in mice. *Eur. J. Immunol.*, 19:729-34.

Mendlovic, S. et al. (1990) The genetic regulation of the induction of experimental SLE. *Immunology*, 69:228-36.

Mozes, E. et al. (1989) Direct binding of a myasthenia gravis related epitope to MHC class II molecules on living murine antigen-presenting cells. *EMBO J.*, 8:4049-52.

Muller, G.M. et al. (1982) Anti-influenza response achieved by immunization with a synthetic conjugate. *Proc. Natl. Acad. Sci. U.S.A.*, 79:569-73.

Nakamura, T. et al. (1993) Gene expression of metalloproteinases and their inhibitor in renal tissue of New Zealand black/white F1 mice. *Clin. Sci.*, 85:295-301.

Naparstek, Y. et al. (1989) Sequential Anti-Idiotypes Define Reciprocal Idiotopes on the Same Anti-DNA Antibody. *Clinical Immunology and Immunopathology*, 50:S106-S116.

Paemen, L. et al. (1994) Evaluation of gelatinases and IL-6 in the cerebrospinal fluid of patients with optic neuritis, multiple sclerosis and other inflammatory neurological diseases. *Eur. J. Neurol.*, 1:55-63.

Ruiz, P.J. et al. (1994) Induction of experimental systemic lupus erythematosus in mice by immunization with the F(ab')2 fragment of the human anti-DNA monoclonal antibody carrying the 16/6 idiotype. *Immunol. Lett.*, 41:79-84.

Saren, P. et al. (1996) TNF-alpha and IL-1beta selectively induce expression of 92-kDa gelatinase by human macrophages. *J. Immunol.*, 157:4159-65.

Schnolzer, M. et al. (1992) In situ neutralization in Boc-chemistry solid phase synthesis. Rapid, High yield assembly of difficult sequences. Int. J. Pept. Protein Res., 40: 180-93.

Segal, R. et al. (1997) Kinetics of cytokine production in experimental systemic lupus erythematosus: involvement of T helper cell 1/T helper cell 2-type cytokines in disease. *J. Immunol.*, 158:3009-16.

Shoenfeld, Y. et al. (1983) Idiotypic cross-reactions of monoclonal human lupus autoantibodies. *J. Exp. Med.*, 158:718-30.

Shoenfeld, Y. et al. (1982) Production of autoantibodies by human-human hybridomas. *J. Clin. Invest.*, 70:205-8.

Sthoeger, Z.M. et al. (1993) Monoclonal anticardiolipin antibodies derived from mice with experimental lupus erythematosus: characterization and the induction of a secondary antiphospholipid syndrome. *J. Clin. Immunol.*, 13:127-38.

Tan, E.M. et al. (1982) The 1982 revised criteria for the classification of systemic lupus erythematosus. *Arthritis Rheum.*, 25:1271-7.

Theofilopoulos, A.N. et al. (1999) Tumour necrosis factor and other cytokines in murine lupus. *Ann. Rheum. Dis.*, 58(Suppl.):149-55.

Tsokos G.C. et al. (1999) Immune Cell Signaling Defects in Lupus: Activation, Anergy and Death. *Immunology Today*.

Ueda et al., "Evaluation of a Sulfobutyl Ether Beta-cyclodextrin as a solubilizing /Stabilizing agent for Several Drugs", Drug Development and Industrial Pharmacy, New York, NY, US, vol. 24, No. 9, Sep. 1, 1998, pp. 863-867.

Waisman, A. et al. (1993) The role of the 16/6 idiotype network in the induction and manifestations of systemic lupus erythematosus. *Int. Immunol.*, 5:1293-300.

Waisman, A. et al. (1993) Variable region sequences of autoantibodies from mice with experimental systemic lupus erythematosus. *Eur. J. Immunol.*, 23:1566-73.

Waisman, A. et al. (1995) The pathogenic human monoclonal anti-DNA that induces experimental systemic lupus erythematosus in mice is encoded by a VH4 gene segment. *Int. Immunol.*, 7:689-696.

Waisman, A., et al. (1997) Modulation of murine systemic lupus erythematosus with peptides based on complementarity determining regions of pathogenic anti-DNA monoclonal antibodies. *Proc. Natl. Acad. Sci. U.S.A.*, 94(4): 4620-5.

Zucker, S. et al. (1999) Increased serum stromelysin-1 levels in systemic lupus erythematosus: lack of correlation with disease activity. *J. Rheumatol.*, 26:78-80.

Supplemental European Search Report of European Application No. EP 04702214.0, issued Aug. 13, 2008.

Supplemental European Search Report of European Application No. EP 04702215.7, issued Aug. 13, 2008.

International Search Report and Written Opinion of the International Searching Authority for PCT International Application No. PCT/US04/00955, issued Dec. 30, 2004.

International Search Report and Written Opinion of the International Searching Authority and International Preliminary Report on Patentability for PCT International Application No. PCT/US04/00948, issued Oct. 12, 2005.

U.S. Appl. No. 12/291,439, filed Nov. 10, 2008, Cohen-Vered et al.

\* cited by examiner

SYNTHETIC HUMAN PEPTIDES AND PHARMACEUTICAL COMPOSITIONS COMPRISING THEM FOR THE TREATMENT OF SYSTEMIC LUPUS ERYTHEMATOSUS

This application is a continuation of U.S. Ser. No. 10/468,924, now abandoned, which is a §371 national stage of PCT International Application No. PCT/IL02/00148, filed Feb. 26, 2002, designating the United States of America, which claims priority of Israeli Application No. 141647, filed Feb. 26, 2001, the contents of each of which are incorporated by reference herein.

FIELD OF THE INVENTION

The present invention relates to synthetic peptides and, more particularly, to synthetic peptides based on the complementarity-determining region (CDR) of a human monoclonal anti-DNA antibody, to pharmaceutical compositions comprising them, and to their use in the immunomodulation of systemic lupus erythematosus (SLE)-associated responses.

Abbreviations: 16/6Id: human 16/6Id mAb; CDR: complementarity-determining region; CFA: complete Freund's adjuvant; hCDR peptide: a peptide based on a CDR region of the human 16/6Id mAb; hCDR1: the human peptide of the SEQ ID NO:6; hCDR3: the human peptide of the SEQ ID NO:7; human 16/6Id mAb: human pathogenic anti-DNA mAb that bears the 16/6Id; ICD: immune complex deposits; Id: idiotype; LNC: lymph node cells; mAb: monoclonal antibody; MMP: matrix metalloproteinase; mCDR1: the murine peptide of the SEQ ID NO:1; mCDR3: the murine peptide of the SEQ ID N3; PBL: peripheral blood lymphocytes; PBS: phosphate-buffered saline; rev: reversed peptide; SLE: systemic lupus erythematosus; SLEDAI: SLE disease activity index; TGF-β: transforming growth factor-β; UT: untreated.

BACKGROUND OF THE INVENTION

Systemic lupus erythematosus (SLE) is an autoimmune disease characterized by the presence of an array of autoantibodies, including antibodies to DNA, antibodies to nuclear antigens and antibodies to ribonucleoproteins. The progression of the disease is associated with general clinical manifestations and damage to tissues and organs caused by deposition of immune complexes. Similar to other autoimmune conditions, the etiology of SLE is multifactorial entailing genetic, environmental, hormonal and immunological factors. No specific treatment aimed towards the prevention or cure of SLE is available.

The human monoclonal anti-DNA antibody termed 16/6Id bears a common idiotype (Shoenfeld et al., 1983). The idiotype was found to have clinical relevance in SLE patients. Thus, the 16/6Id was found to be expressed on anti-DNA antibodies of 54% of SLE patients with active disease (Isenberg et al., 1984) and in affected organs of patients with SLE (Isenberg and Collins, 1985). Mice of inbred strains that do not develop any spontaneous autoimmune diseases were immunized with this human anti-DNA 16/6Id mAb and developed the major hallmarks of SLE in humans and in the spontaneous murine models for this disease (Mendlovic et al., 1988). Thus, following immunization, the mice produced antibodies specific to the 16/6Id, antibodies that bear the 16/6Id and antibodies directed against different nuclear antigens (dsDNA, ssDNA, Sm, ribonucleoprotein, Ro, La and others). The serological findings were associated with leukopenia, elevated erythrocyte sedimentation rate, proteinuria, abundance of immune complexes in the kidneys and sclerosis of the glomeruli (Mendlovic et al., 1988), which are typical manifestations of SLE.

A murine anti-16/6Id mAb (Ab2) derived from mice with experimental SLE was also capable of inducing the experimental disease in mice (Mendlovic et al., 1989) similar to the 16/6Id (Ab1). Moreover, a murine anti-DNA mAb that expresses the 16/6Id was prepared from mice afflicted with experimental SLE. The antibody Ab3 termed 5G12 reacted with antibodies specific to the 16/6Id. Immunization with the latter antibody resulted in the induction of experimental SLE with similar manifestations as observed following immunization with the human 16/6Id (Ab1) and with the murine anti-16/6Id (Ab2) mAbs (Waisman et al., 1993). These results show the importance of the 16/6Id network in the induction and progression of SLE in mice.

In order to understand the mechanism by which self-antibodies associated with SLE arise, the present inventor has produced a variety of monoclonal autoantibodies derived from C3H.SW mice in which experimental SLE was induced. As a rule, the monoclonal autoantibodies that were capable of eliciting antibodies that bear the 16/6Id or react with it were found to be pathogenic and thus capable of inducing experimental SLE in mice (Fricke et al., 1990; Sthoeger et al., 1993).

Later on, the variable (V) regions of nine autoantibodies that bind either DNA or HeLa nuclear extract (NE), isolated from the C3H.SW mice with experimental SLE, were sequenced (Waisman and Mozes, 1993). Monoclonal antibodies with different specificity were analyzed in an attempt to determine the connections between the different autoantibodies. Three mAb were found to bind DNA, and were shown to exhibit sequence characteristics of pathogenic anti-DNA antibodies. One of these mAb, designated 2C4C2, was shown to use a heavy (H) chain V region gene ($V_H$) identical to the $V_H$ of anti-DNA mAb isolated from other lupus-prone mice, namely (NZB×NZW)F$_1$. The light (L) chain V region gene ($V_L$) of mAb 2C4C2 is 98% homologous to the $V_L$ of another anti-DNA mAb, also isolated from (NZB×NZW)F$_1$ mice. The other two anti-DNA mAb, designated 5G12-4 and 5G12-6, share 93% of their $V_H$ sequences with that of mAb 2C4C2. Based on the analysis of these mAbs, it appeared that autoantibodies found in mice with experimental SLE use genetic elements similar to those used by mAb that were isolated from mouse strains which develop lupus spontaneously.

T cells play an important role in the induction and development of experimental SLE. Thus, T cell lines and clones specific to the 16/6Id were shown to induce experimental SLE in syngeneic recipients similarly to the 16/6Id antibody. Therefore, following the inoculation of the activated cells of the lines, the mice developed both the serology and the renal damage which is typical to SLE (Fricke et al., 1991).

As described above, the mAb 5G12 that was isolated from mice with experimental SLE and was shown to bind DNA and bear the 16/6Id, is capable of inducing experimental SLE in mice (Waisman et al., 1993). T cells that react specifically to mAb by proliferation, are probably reacting to peptides representing sequences from their complementarity-determining regions (CDR). It is very likely that the T cells recognize the V regions of the above antibodies since they do not react with other antibodies that carry the same constant region but have different specificities. Within the variable region, the regions with the highest probability to be recognized are the CDR, since those are the regions that differ the most between the various antibodies. The CDR regions of the $V_H$ sequences of the nine pathogenic murine mAb mentioned above that induce SLE in mice, are boxed in FIG. 1 of Waisman and Mozes, 1993, in which the complete nucleotide and deduced amino acid sequences for the variable heavy chains ($V_H$) of the nine mAbs are presented.

International PCT Patent Publication No. WO 96/30057 of the present applicants describes peptides based on the CDR regions of pathogenic mAbs isolated from mice with experimental SLE, in particular peptides Ia to IIIa, based on the CDR1, CDR2 and CDR3 regions, respectively, of the $V_H$ chain of the murine mAb termed 5G12, and peptides IVa and Va, based on the CDR1 and CDR3 regions, respectively, of the $V_H$ chain of the murine mAb termed 2C4C2. These peptides have the sequences substantially as denoted by SEQ ID NO:1 to SEQ ID NO: 5 as follows:

```
TGYYMQWVKQSPEKSLEWIG    (Ia)     [SEQ ID NO: 1]

EINPSTGGTTYNQKFKAKAT    (IIa)    [SEQ ID NO: 2]

YYCARFLWEPYAMDYWGQGS    (IIIa)   [SEQ ID NO: 3]

GYNMNWVKQSHGKSLEWIG     (IVa)    [SEQ ID NO: 4]

YYCARSGRYGNYWGQTL       (Va)     [SEQ ID NO: 5]
```

These peptides and, in particular, the peptides Ia and IIIa, herein designated mCDR1 [SEQ ID NO:1] and mCDR3 [SEQ ID NO:3], respectively, were shown by the inventor to be capable, when administered in PBS, of inhibiting T cell priming to either the appropriate mCDR peptide or to the whole anti-DNA 16/6Id mAb of either murine or human origin (Waisman et al., 1997). The peptides mCDR1 and mCDR3 were further shown by the inventor to either prevent or treat an already established SLE that is either induced by the human anti-DNA 16/6Id mAb or that develops spontaneously in the SLE prone mice (NZB×NZW) F1 or MRL/lpr/lpr (Eilat et al., 2000 and 2001).

SUMMARY OF THE INVENTION

It has now been found according to the present invention that peptides based on the CDR of the human monoclonal anti-DNA 16/6Id antibody are capable of immunomodulating SLE-associated responses. Thus, peptides based on the CDR1 and CDR3 of the human 16/6Id were tested and shown to inhibit lymph node cell proliferation of mice immunized with the murine peptides mCDR1 (SEQ ID NO:1) and mCDR3 (SEQ ID NO:3) or with the whole human anti-DNA 16/6Id mAb, to inhibit the proliferative response of peripheral blood lymphocytes (PBL) of SLE patients to the human anti-DNA 16/6Id mAb, and to ameliorate disease manifestations of mice afflicted with spontaneous or experimental SLE.

These findings are completely unexpected because not all CDRs of pathogenic autoantibodies are equally recognized by T cells of patients. As shown previously in the laboratory of the present inventor (Dayan et al., 2000), the CDRs of the anti-DNA autoantibody 2C4C2 are less well recognized by T cells of SLE patients than the peptides based on the CDRs of the anti-DNA antibody 5G12. Furthermore, many of the analogs of the peptides based on the CDRs of the murine autoantibodies described in the above-mentioned WO 96/30057 were shown not to be efficient in their inhibitory effects, and thus the modifications occurring in the sequences of the peptides based on the CDRs of a human monoclonal anti-DNA antibody of the present invention, could not be predicted or suggested to be efficient. In addition, the use of peptides based on a human antibody should be considered as preferable for human use in comparison with peptides based on non-human antibodies.

The present invention thus relates, in one aspect, to a synthetic peptide selected from the group consisting of:

(a) a peptide of at least 12 and at most 30 amino acid residues comprising a sequence consisting of, or found within, a complementarity-determining region (CDR) found in the heavy or light chain of the human monoclonal anti-DNA 16/6Id antibody (hereinafter "hCDR sequence"), or a sequence obtained by: (i) replacement of one or more of the amino acid residues of the hCDR sequence by different amino acid residues; (ii) deletion of one or more amino acid residues from the hCDR sequence; and/or (iii) addition of one or more amino acid residues to the hCDR sequence, or a salt or a chemical derivative of said peptide;

(b) a dual synthetic peptide comprising two different ones of said peptide of (a) covalently linked to one another either directly or through a short linking chain;

(c) a peptide polymer comprising a plurality of sequences of said peptide of (a); and (d) a peptide of (a) or a peptide polymer of (c) attached to a macromolecular carrier.

The human monoclonal anti-DNA 16/6Id antibody, herein referred to as "human 16/6Id mAb", is a pathogenic human monoclonal anti-DNA antibody capable of inducing a SLE-like disease in mice.

A peptide according to the invention comprising a hCDR sequence as defined above is herein referred to as "hCDR peptide".

In one preferred embodiment, the hCDR peptide includes a sequence of a CDR, more preferably of the CDR1 or CDR3, of the heavy chain of the human 16/6Id mAb, such as, but not being limited to, the peptides herein designated hCDR1 and hCDR3, having the sequences substantially as denoted by SEQ ID NO:6 and SEQ ID NO:7, respectively, as follows:

```
GYYWSWIRQPPGKGEEWIG        [SEQ ID NO: 6]

YYCARGLLRGGWNDVDYYGMDV     [SEQ ID NO: 7]
```

In another aspect, the invention provides a pharmaceutical composition comprising at least one synthetic peptide or peptide polymer of the invention, and a pharmaceutically acceptable carrier. The pharmaceutical composition is particularly useful for the treatment of SLE and amelioration of the clinical manifestations of the disease, particularly by modulating SLE-associated responses, e.g. down-regulating the levels of MMP-3 and/or MMP-9, and/or IL-2 and/or IFN-γ activities, or up-regulating the level of TGF-β activity in a patient with SLE.

In a further aspect, the invention relates to a method for the treatment of SLE comprising administering to an SLE patient an effective amount of a peptide or peptide polymer of the invention. The invention further relates to a method of immunomodulating SLE-associated responses, e.g. down-regulating the levels of MMP-3 and/or MMP-9, and/or IL-2 and/or IFN-γ activities, or up-regulating the level of TGF-β activity in a patient with SLE, comprising administering to an SLE patient an effective amount of a peptide or peptide polymer of the invention.

In still a further aspect, the invention relates to a method for assessing the effectiveness of a drug in the treatment of a SLE patient which comprises measuring at different intervals of time the levels of MMP-3 and/or MMP-9 in a blood sample obtained from said patient being treated with said drug, whereby a decreased level of MMP-3 and/or MMP-9 correlates with the effectiveness of the drug.

In still another further aspect, the invention relates to a method for assessing the effectiveness of a drug in the treatment of a SLE patient which comprises measuring at different intervals of time the level of IL-2 and/or IFN-γ in a blood sample obtained from said patient being treated with said drug, whereby a decreased level of IL-2 and/or IFN-γ correlates with the effectiveness of the drug.

In yet still a further aspect, the invention relates to a method for assessing the effectiveness of a drug in the treatment of a SLE patient which comprises measuring at different intervals of time the level of TGF-β in a blood sample obtained from said patient being treated with said drug, whereby an increased level of TGF-β correlates with the effectiveness of the drug.

The drug which effectiveness is to be assessed according to any of the above methods may be, for example, without being limited to, a peptide according to the invention or a murine peptide as described in the above-mentioned WO 96/30057.

BRIEF DESCRIPTION OF THE DRAWINGS

FIG. 3A—IFN-γ pattern; FIG. 3B—TGF-β pattern: FIG. 3C—IL-10 pattern.

FIG. 13A—IFN-γ pattern; FIG. 13B—IL-10 pattern; FIG. 13C—TGF-β pattern.

FIG. 15A—IFN-γ pattern; FIG. 15B—TNF-α; FIG. 15C—IL-10 pattern; FIG. 15D—TGF-β pattern; FIG. 15E—TGF-β pattern, measured in supernatants of 16/6Id-triggered spleen cells.

FIGS. 21A-22B depict levels of MMP-3 and MMP-9 in 16/6Id-immunized BALB/c mice treated with mCDR1. In prevention experiments, mice (8/group) were treated i.v. with mCDR1 (100 μg/mouse). The results shown are of sera taken 4.5 months after the end of the treatment. In treatment experiments, mice (8/group) were treated s.c. with 100 μg/mouse mCDR1. The results are of sera obtained at the end of treatment. Pools of sera of each experimental group were tested for MMP-3 by Western blot analysis (21A) and for MMP-9 activity by gel zymography (21B). UT—untreated. The results are representative of 2 similar experiments.

FIGS. 22A-22B depict immunostaining for MMP-3 and MMP-9 of kidney sections of 16/6Id immunized BALB/c mice that were treated with mCDR1 for prevention (22A) or treatment (22B) of experimental SLE. Mice were sacrificed 8 months following disease induction, and their kidneys were removed. Cryostat sections (5 μm) were prepared and immunostained for MMP-3, MMP-9 and for the presence of immune complex deposits (×200). (W/O)— control staining to the efficiency of blocking, without the first antibody. The results are representative of 2 similar experiments.

DETAILED DESCRIPTION OF THE INVENTION

Figure 1:
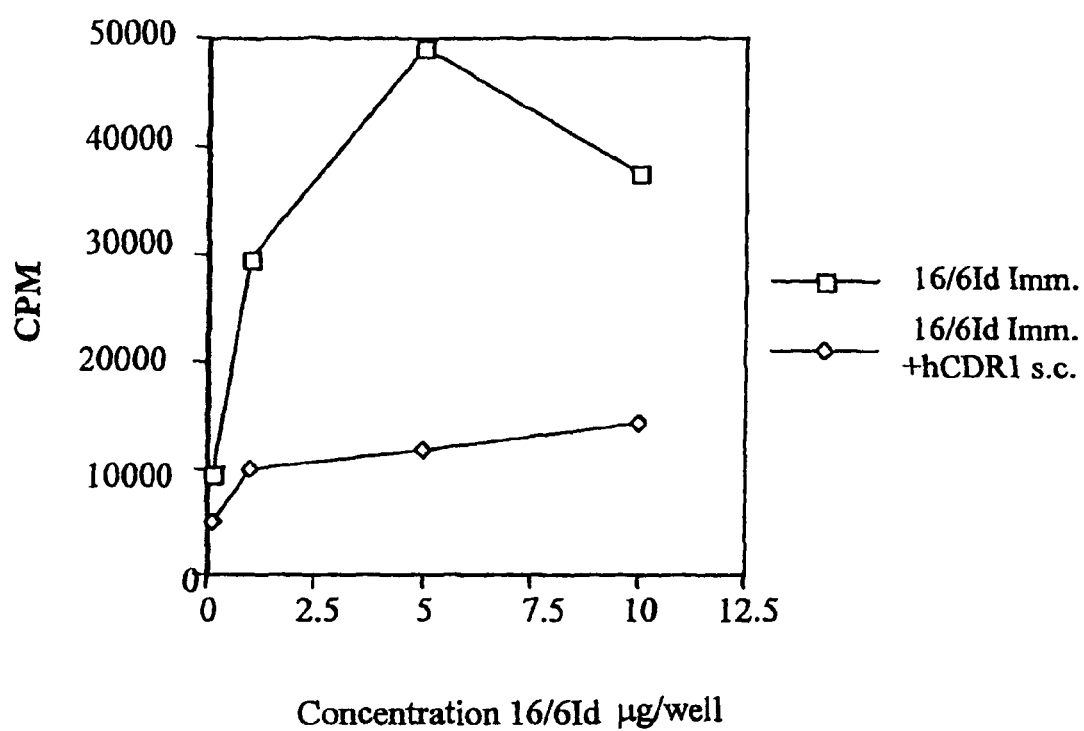
FIG. 1 shows inhibition of the proliferative responses of lymph node cells of mice immunized with human 16/6Id mAb to various concentrations of the 16/6Id mAb (0.1-10 μg/well), by treatment with 300 μg hCDR1.

The present invention relates, in one aspect, to synthetic peptides comprising a sequence consisting of, or found within, a CDR found in the heavy or light chain of the pathogenic human monoclonal anti-DNA 16/6Id antibody (herein identified as "human anti-DNA 16/6Id mAb" or "human 16/6Id mAb"), which antibody induces a SLE-like disease in mice.

The synthetic peptides of the invention derived from a CDR of the human 16/6Id mAb, herein identified as hCDR peptides, are preferably based on a CDR found in the heavy chain of the human 16/6Id mAb.

The CDR regions of the $V_H$ sequences of the human 16/6Id mAb are boxed in FIG. 4A of Waisman et al., 1995. The CDR regions of the heavy chains of the human 16/6Id mAb have the sequences substantially as denoted by SEQ ID NO: 8 to SEQ ID NO:10, as follows:

| CDR1: | FSGYYWS | [SEQ ID NO: 8] |
| CDR2: | EINHSGSTNYKTSLKS | [SEQ ID NO: 9] |
| CDR3: | GLLRGGWNDVDYYYGMDV | [SEQ ID NO: 10] |

The hCDR peptides of the invention contain at least 12 and at most 30 amino acid residues and comprise, preferably, a sequence identical to a sequence selected from the group consisting of SEQ ID NO: 8, 9 and 10, or more preferably a sequence found within said SEQ ID NO: 8, 9 or 10, or a sequence obtained by: (i) replacement of one or more of the amino acid residues of the SEQ ID NO: 8, 9 and 10 sequences by different amino acid residues; (ii) deletion of one or more amino acid residues from the SEQ ID NO: 8, 9 and 10 sequences; or (iii) addition of one or more amino acid residues to the SEQ ID NO: 8, 9 and 10 sequences.

The hCDR peptides of the invention, besides the hCDR sequence, contain further amino acid residues, preferably amino acid residues of the sequences of the human 16/6Id mAb flanking the hCDR sequences or sequences obtained by replacement of one or more of the amino acid residues of the hCDR flanking sequences by different amino acid residues, by deletion of one or more amino acid residues from the hCDR flanking sequences or by addition of one or more amino acid residues to the hCDR flanking sequences.

Thus, in one embodiment, the present invention provides a synthetic peptide based on the CDR1 of the heavy chain of the human 16/6Id mAb, said CDR1 region being of the sequence substantially as denoted by SEQ ID NO:8, said peptide being selected from the group consisting of:

(a) a peptide comprising a sequence consisting of, or found within, the sequence of SEQ ID NO: 8, or a sequence obtained by: (i) replacement of one or more of the amino acid residues of said SEQ ID NO:8 by different amino acid residues; (ii) deletion of one or more amino acid residues from said SEQ ID NO:8; and/or (iii) addition of one or more amino acid residues to said SEQ ID NO:8, or a salt or a chemical derivative of said peptide;

(b) a dual synthetic peptide comprising two different ones of said peptide of (a) covalently linked to one another either directly or through a short linking chain;

(c) a peptide polymer comprising a plurality of sequences of said peptide of (a); and (d) a peptide of (a) or a peptide polymer of (c) attached to a macromolecular carrier.

In one preferred embodiment of the invention, a peptide based on the CDR1 of the heavy chain of the human 16/6Id mAb is a peptide of the sequence substantially as denoted by SEQ ID NO:11:

```
X₁YYWSWIX₂QX₃PX₄X₅GX₆EWIG        [SEQ ID NO: 11]
``` wherein $X_1$ is G or TG; $X_2$ is R or K; $X_3$ is P or S; $X_4$ is G or E; $X_5$ is K or D; and $X_6$ is E, L or S.

In a more preferred embodiment, the peptide of SEQ ID NO:11 is the 19-mer peptide herein designated "hCDR1 peptide" or simply "hCDR1", of the sequence substantially as denoted by SEQ ID NO:6:

```
GYYWSWIRQPPGKGEEWIG              [SEQ ID NO: 6]
```

In hCDR1, the sequence GYYWS comprised within SEQ ID NO:8, is followed by the natural sequence of the CDR1 of the heavy chain of the human 16/6Id mAb, with the exception that the natural leucine (L) residue of the mAb sequence was replaced by a glutamic acid residue (E) (bold) at position 15 of the peptide hCDR1.

In another embodiment, the peptide of SEQ ID NO:11 is an analog of the hCDR1 peptide obtained by replacement and/or addition of amino acid residues to the sequence of the hCDR1 peptide, examples thereof being the peptides of the sequences substantially as denoted by SEQ ID NO:12 to SEQ ID NO:18 (wherein the amino acids replaced or added are represented in bold):

```
GYYWSWIRQPPGKGLEWIG              [SEQ ID NO: 12]

GYYWSWIRQPPGKGSEWIG              [SEQ ID NO: 13]

GYYWSWIRQPPGDGEEWIG              [SEQ ID NO: 14]

GYYWSWIKQPPGKGEEWIG              [SEQ ID NO: 15]

GYYWSWIRQSPGKGEEWIG              [SEQ ID NO: 16]

GYYWSWIRQPPEKGEEWIG              [SEQ ID NO: 17]

TGYYWSWIRQPPGKGEEWIG             [SEQ ID NO: 18]
```

In a further embodiment, the invention provides a synthetic peptide based on the CDR3 of the heavy chain of the human 16/6Id mAb, said CDR3 region being of the sequence substantially as denoted by SEQ ID NO:10, said peptide being selected from the group consisting of:

(a) a peptide comprising a sequence consisting of, or found within, the sequence of SEQ ID NO:10, or a sequence obtained by: (i) replacement of one or more of the amino acid residues of said SEQ ID NO:10 by different amino acid residues; (ii) deletion of one or more amino acid residues from said SEQ ID NO:10; and/or (iii) addition of one or more amino acid residues to said SEQ ID NO:10, or a salt or a chemical derivative of said peptide;

(b) a dual synthetic peptide comprising two different ones of said peptide of (a) covalently linked to one another either directly or through a short linking chain;

(c) a peptide polymer comprising a plurality of sequences of said peptide of (a); and (d) a peptide of (a) or a peptide polymer of (c) attached to a macromolecular carrier.

In one preferred embodiment of the invention, the peptide based on the CDR3 of the heavy chain of the human 16/6Id mAb is a peptide of the sequence substantially as denoted by SEQ ID NO:19:

```
YYCARX₁LLX₂X₃X₄X₅X₆DVDYX₇GX₈DV    [SEQ ID NO: 19]
``` wherein $X_1$ is G or F; $X_2$ is R or A; $X_3$ is G or A; $X_4$ is G or A; $X_5$ is W or A; $X_6$ is N or A; $X_7$ is Y or W; and $X_8$ is M or Q.

In a more preferred embodiment, the peptide of SEQ ID NO:19 is the peptide herein designated "hCDR3 peptide" or simply "hCDR3", of the SEQ ID NO:7:

```
YYCARGLLRGGWNDVDYYGMDV           [SEQ ID NO: 7]
```

In hCDR3, the sequence GLLRGGWNDVDYYYGMDV [SEQ ID NO:10] of the CDR3 region of the heavy chain of the human 16/6Id mAb is modified by deletion of one of the tyrosine (Y) residues and is preceded by the natural sequence of the mAb.

In another embodiment, the peptide of SEQ ID NO:19 is an analog of the hCDR3 peptide obtained by replacement and/or addition of amino acid residues to the sequence of the hCDR3 peptide, examples thereof being the peptides of the sequences SEQ ID NO:20 to SEQ ID NO:27 (wherein the amino acids replaced or added are represented in bold):

```
YYCARGLLRGGWADVDYYGMDV           [SEQ ID NO: 20]

YYCARGLLRGGANDVDYYGMDV           [SEQ ID NO: 21]

YYCARGLLRGAWNDVDYYGMDV           [SEQ ID NO: 22]

YYCARGLLRAGWNDVDYYGMDV           [SEQ ID NO: 23]

YYCARGLLAGGWNDVDYYGMDV           [SEQ ID NO: 24]

YYCARFLLRGGWNDVDYYGMDV           [SEQ ID NO: 25]

YYCARGLLRGGWNDVDYYGQDV           [SEQ ID NO: 26]

YYCARGLLRGGWNDVDYWGMDV           [SEQ ID NO: 27]
```

In still a further embodiment, the invention provides a synthetic peptide based on the CDR2 of the heavy chain of the human 16/6Id mAb, said CDR2 region being of the sequence substantially as denoted by SEQ ID NO:9, said peptide being selected from the group consisting of:

(a) a peptide comprising a sequence consisting of, or found within, the sequence of SEQ ID NO: 9, or a sequence obtained by: (i) replacement of one or more of the amino acid residues of said SEQ ID NO:9 by different amino acid residues; (ii) deletion of one or more amino acid residues from said SEQ ID NO:9; and/or (iii) addition of one or more amino acid residues to said SEQ ID NO:9, or a salt or a chemical derivative of said peptide;

(b) a dual synthetic peptide comprising two different ones of said peptide of (a) covalently linked to one another either directly or through a short linking chain;

(c) a peptide polymer comprising a plurality of sequences of said peptide of (a); and (d) a peptide of (a) or a peptide polymer of (c) attached to a macromolecular carrier.

The synthetic peptides of the present invention have 12-30, preferably 17-23, most preferably 19-22, amino acid residues, and may be manufactured by chemical synthesis or by recombinant technology by methods well known in the art.

When preparing analogs as described above obtained by substitution of amino acid residues, it is important that the substitutions be selected from those which cumulatively do not substantially change the volume, hydrophobic-hydrophilic pattern and charge of the corresponding portion of the unsubstituted parent peptide. Thus, a hydrophobic residue may be substituted with a hydrophilic residue, or vice-versa, as long as the total effect does not substantially change the volume, hydrophobic-hydrophilic pattern and charge of the corresponding unsubstituted parent peptide.

The present invention also includes chemical derivatives of a peptide of the invention. The "chemical derivative" contains additional chemical moieties not normally a part of the peptide and is encompassed by the invention as long as it retains at least a portion of the function of the peptide which permits its utility in preventing or inhibiting T cell proliferative responses and autoimmune disease. For example, a chemical derivative may result from the reaction of an organic derivatizing agent capable of reacting with selected side chains or terminal residues of said peptide, and will preferably retain at least a portion of the function of the peptide to inhibit specifically the proliferative response and cytokine secretion of T lymphocytes of mice that are high responders to SLE-inducing autoantibodies. Among these chemical derivatives, the amides are of particular interest, both amides of carboxyl groups at the C-terminus and amides of free carboxyl groups of aspartic or glutamic acid residues. Many such chemical derivatives and methods for making them are well known in the art.

Also included in the scope of the invention are salts of the peptides and analogs of the invention. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivatives and salts are preferably used to modify the pharmaceutical properties of the peptide insofar as stability, solubility, etc., are concerned.

The hCDR peptides according to the invention may be selected by testing for their potential in inhibiting the proliferative response of T lymphocytes of mice that are high responders to SLE-inducing autoantibodies. Once a peptide in accordance with the present invention is produced, its ability to inhibit the proliferative response of T lymphocytes of mice that are high responders to SLE-inducing autoantibodies may be readily determined by those of ordinary skill in the art without undue experimentation using tests such as those described herein. One test which may be readily conducted is for the ability of the peptides to inhibit in vitro the proliferative responses of certain T cell lines and clones specific to SLE-inducing autoantibodies. The T cell lines and clones may be, for example, the T cell lines and clones specific to the 16/6Id mAb (Fricke et al., 1991) established from immunized lymph node cells of mice by previously described methodology (Axelrod, O. and Mozes, E. *Immunobiology*, 172, 99 (1986)). Cells are exposed to the stimulating antibody presented on irradiated syngeneic spleen cells in the presence of enriched medium every two weeks. The T cell lines are cloned by the standard limiting dilution technique. The proliferative responses of these T cell lines and clones are tested, for example, by the method described in WO 96/30057, in Materials and Methods, section (g).

Another test which can be conducted in order to select analogs having the desired activity is to test for the ability of the synthetic peptides to inhibit the ability of the T cell lines and clones to provide help to peptide-specific B cells in the presence of the parent peptide. The synthetic peptides may also be tested for their ability to bind directly, following biotinylation, to MHC Class II products on antigen-presenting cells of the relevant strains. For this purpose, N-terminal biotinylation of the relevant peptides is performed at 0° C. with an excess of biotin-N-hydroxysuccinimide in aqueous solution (Mozes et al., 1989). Mouse splenic adherent cells or PBL-adherent cells ($1 \times 10^6$/sample) are incubated with biotinylated peptides in PBS containing 0.1% bovine serum albumin (PBS/BSA) at 37° C. for 20 hr, followed by incubation with phycoerythrin-streptavidin for 30 min at 4° C. After each incubation, the cells are washed twice with the above solution. Thereafter, the cells are analyzed by flow cytometry using FACScan. In each analysis, a minimum of 5000 cells are examined (for above procedures, see, for example, Mozes et al., 1989).

A further test which can be conducted is to test for the ability of the peptides to inhibit cytokine secretion by the T cell line or by T lymphocytes or lymph node cells of mice that are high responders to SLE-inducing autoantibodies. The cytokines are detected as follows: IL-1 activity is assessed by ELISA using a pair of capture and detecting antibodies (as described below for IL-4, IL-6, IL-10). IL-2 is directly detected using the IL-2 dependent CTLL line or by ELISA. Levels of IL-4, IL-6, IL-10, INF-γ and TNF-α in the supernatants are determined by ELISA using antibodies to the various cytokines (Pharmingen, San Diego, Calif., USA) according to the manufacturer's instructions. In addition, the ability of the peptides to elevate the level of secretion of the immunosuppressive cytokine TGF-β can be assessed by ELISA as described herein in the Examples.

Peptides which test positive in one or more of these in vitro tests will provide a reasonable expectation of in vivo activity. However, in vivo tests can also be conducted without undue experimentation. Thus, for example, adult mice may be injected with the candidate peptide at either day −3 or day 0. The mice are then immunized with the disease-inducing autoantibody or with the peptide. Ten days later, lymph node cells of the mice are tested for their ability to proliferate to the immunogen in order to find out the inhibitory capacity of the candidate peptide.

Another such in vivo animal test consists of measuring the therapeutic activity directly in the murine model in vivo for the production of SLE as described above. The peptides can be injected into the mice in which experimental SLE is induced by different routes at different dosages and at different time schedules. Furthermore, the treated mice can be tested periodically in order to determine the effect of the peptides on the autoantibody responses and on disease manifestations elicited in the mice by the SLE-inducing autoantibody.

Another in vivo procedure consists of assessing the candidate peptide ability to treat mice that spontaneously develop SLE e.g. (NZB×NZW)F1 mice, as described herein in the Examples.

It can thus be seen that, besides the preferred embodiments which have been shown to be operable in the examples herein, those of ordinary skill in the art will be able to determine additional analogs which will also be operable following the guidelines presented herein without undue experimentation.

In another preferred embodiment, the present invention provides a multi-epitope single peptide such as a dual peptide. In one embodiment, the dual peptide consists of two different peptides based on the same CDR such as two different peptides including the sequence of the CDR1 (SEQ ID NO:8) or of the CDR3 (SEQ ID NO:10) of the heavy chain of the human 16/6Id mAb.

In another and more preferred embodiment, the dual peptide consists of two different peptides each based on a different CDR such as one peptide including the sequence of CDR1 (SEQ ID NO:8) and another including the sequence of the CDR3 (SEQ ID NO:10) of the heavy chain of the human 16/6Id mAb.

The dual peptide according to the invention preferably consists of two different peptides, one being a peptide of SEQ ID NO:11 and the other being a peptide of SEQ ID NO:19, more preferably one peptide selected from the group consisting of SEQ ID NO:6 and NO:12-18 and another peptide selected from the group consisting of SEQ ID NO:7 and NO:20-27, most preferably one peptide being the peptide of SEQ ID NO:6 and the other being the peptide of SEQ ID NO:7, the two different peptides being covalently linked to one another either directly or by a short linking chain such as a stretch of alanine residues or by a putative site for proteolysis by cathepsin. See, for example, U.S. Pat. No. 5,126,249 and European Patent 495049 with respect to such sites.

In yet another preferred embodiment, the present invention provides a multi-epitope single peptide comprising a number of the same or different peptides of the present invention in the form of a peptide polymer, obtained, for example, by polymerization of the peptides with a suitable polymerization agent, such as 0.1% glutaraldehyde (Audibert et al., 1981, Nature 289:593). The polymer will preferably contain from 5 to 20 peptide residues, preferably a peptide of SEQ ID NO: 6, 7 and 11-27. Such peptide polymers may also be formed by crosslinking the peptides or attaching multiple peptides to macromolecular carriers. Suitable macromolecular carriers are, for example, proteins, such as tetanus toxoid, and linear or branched copolymers of amino acids, such as a linear copolymer of L-alanine, L-glutamic acid and L-lysine and a branched copolymer of L-tyrosine, L-glutamic acid, L-alanine and L-lysine (T,G)-A-L-, or multichain poly-DL-alanine (M. Sela et al., 1955, J. Am. Chem. Soc. 77:6175). The conjugates are obtained, for example, by first coupling the peptide with a water-soluble carbodiimide, such as 1-ethyl-3-(3'-dimethylamino-propyl)carbodiimide hydro-chloride, and then performing the conjugation with the macromolecular carrier as described by Muller, G. M. et al. (1982) Proc. Natl. Acad. Sci. USA 79:569. The contents of the coupled peptide in each conjugate are determined by amino acid analysis, in comparison to the composition of the carrier alone.

According to a further embodiment of the present invention, one or more active peptides may be attached to a suitable macromolecular carrier or may be polymerized in the presence of glutaraldehyde.

The peptides, polymers thereof or their conjugates with suitable macromolecular carriers, are administered to patients in a form that insures their bioavailability, making them suitable for treatment. If more than one peptide of the invention is found to have significant inhibitory activity, these peptides may be given to patients in a formulation containing a mixture thereof.

The invention thus further relates to pharmaceutical compositions comprising at least one synthetic peptide or peptide polymer according to the invention, optionally with a pharmaceutically acceptable carrier.

In one preferred embodiment, the pharmaceutical compositions comprises at least one synthetic peptide of the invention, more preferably a peptide selected from the group consisting of peptides hCDR1 [SEQ ID NO:6] and hCDR3 [SEQ ID NO:7] and peptides obtained by substitution and/or addition of amino acid residues in the hCDR1 and hCDR3 sequences, in particular a peptide selected from the group consisting of peptides of SEQ ID NO:12 to SEQ ID NO:18 and of SEQ ID NO:20 to SEQ ID NO:27.

Any suitable route of administration is encompassed by the invention, including oral, intravenous, subcutaneous, intraarticular, intramuscular, inhalation, intranasal, intrathecal, intraperitoneal, intradermal, transdermal or other known routes, including the enteral route. In preferred embodiments, the peptides of the invention are administered by oral, intranasal or subcutaneous routes.

The dose ranges for the administration of the compositions of the present invention should be large enough to produce the desired effect, whereby, for example, an immune response to the SLE-inducing autoantibody, as measured by T cell proliferation in vitro, is substantially prevented or inhibited, and further, where the disease is significantly treated. The doses should not be so large as to cause adverse side effects, such as unwanted cross reactions, generalized immunosuppression, anaphylactic reactions and the like.

Effective doses of the peptides of this invention for use in treating SLE are in the range of about 1 µg to 1 mg and up to 100 mg/kg body weight.

The synthetic human peptides of the invention are aimed at inhibiting or suppressing specific antigen responses of SLE patients, without affecting all other immune responses. This approach is of the utmost importance since most diagnosed patients are young women that have to be treated for many years and the currently accepted treatment for SLE involves administration of immunosuppressive agents, such as corticosteroids and/or cytotoxic drugs, that are both non-specific and have multiple adverse side effects.

The invention further relates to a method for the treatment of systemic lupus erythematosus (SLE) comprising administering to a SLE patient an effective amount of a peptide or peptide polymer of the invention. In one preferred embodiment, the method comprises administering the peptide of the SEQ ID NO: 6. In another preferred embodiment, the method comprises administering the peptide of the SEQ ID NO: 7.

The invention still further relates to method of immunomodulation of SLE-associated responses in a SLE patient which comprises administering to said SLE patient an effective amount of an effective amount of a peptide or peptide polymer of the invention. In one embodiment, the method comprises down-regulating the levels of matrix metalloproteinase (MMP)-3 and/or MMP-9 activities in a SLE patient. In another embodiment, the method comprises immunomodulating the level of a cytokine activity in a SLE patient, particularly down-regulating the level of IL-2 and/or IFN-γ activity and/or up-regulating the level of TGF-β activity, in a SLE patient. In one preferred embodiment, the method comprises administering the peptide of the SEQ ID NO: 6. In another preferred embodiment, the method comprises administering the peptide of the SEQ ID NO: 7.

The invention also provides methods for assessing the effectiveness of a drug in the treatment of a SLE-patient which comprises measuring at different intervals of time the levels of MMP-3, MMP-9, IL-2, IFN-γ and/or TGF-β in a blood sample obtained from said patient being treated with said drug, whereby a decreased level of MMP-3, MMP-9, IL-2 and/or IFN-γ or an increased level of TGF-β, correlates with the effectiveness of the drug.

The invention still further relates to the use of a peptide of or peptide polymer of the invention for the preparation of a pharmaceutical composition, in particular for treatment of SLE, more particularly for immunomodulation of SLE-associated responses in a SLE patient such as down-regulation of MMP-3 and/or MMP-9 and/or IL-2 and/or IFN-γ or up-regulation of TGF-β levels in a SLE-patient.

The present invention will now be described in more detail in the following non-limiting Examples and the accompanying figures.

EXAMPLES

Materials and Methods

Mice. Female (NZB×NZW)F1 mice were obtained from the Jackson Laboratory (Bar Harbor, Me.). Female mice of the BALB/c inbred strain at the age of 6-8 weeks were obtained from the Experimental Animal Unit, The Weizmann Institute of Science, Rehovot, Israel.

Anti-DNA monoclonal antibody. The human anti-DNA mAb that bears the 16/6Id (IgG1/k) was previously characterized (Shoenfeld et al., 1982; Waisman et al., 1995). The mAb was secreted by hybridoma cells that were grown in culture and were purified by using a protein G-Sepharose column (Pharmacia, Fine Chemicals, Uppsala, Sweden).

Synthetic peptides. The synthetic murine peptides mCDR1 (SEQ ID NO:1) and mCDR3 (SEQ ID NO:3) as well as the reversed peptides that were synthesized in the reversed order of mCDR1 and mCDR3 and in the reversed order of the human peptide hCDR1, identified herein as revmCDR1 [SEQ ID NO: 28], revmCDR3 [SEQ ID NO: 29], and revhCDR1 [SEQ ID NO:30], respectively, used as control, were prepared as previously described (WO 96/30057 or using an automated synthesizer (Applied Biosystems model 430A, Germany) by using the company's protocols for t-butyloxycarbonyl (t-Boc) technique.

The reversed peptides have the sequences:

```
GIWELSKEPSQKVWQMYYGT    revmCDR1   [SEQ ID NO: 28]

SGQGWYDMAYPEWLFRACYY    revmCDR3   [SEQ ID NO: 29]

GIWEEGKGPPQRIWSWYYG     revhCDR1   [SEQ ID NO: 30]
```

Induction and treatment of experimental SLE. In order to induce experimental SLE, BALB/c mice were immunized with 1-2 μg of the human mAb 16/6Id and boosted 3 weeks later. For the prevention of experimental SLE, mice were given hCDR1 or hCDR3 (mCDR1 or revmCDR1 as control peptide in Example 12) intravenously (i.v.) or s.c. concomitant with the immunization, and were injected weekly thereafter for 5 weeks. Treatment of an established disease started three and a half months following disease induction with the 16/6Id, when clinical manifestations were already observed. In Example 12, mice received 10 weekly injections (i.v. or s.c.) of mCDR1 or revmCDR1 at a dose of 100 μg/mouse.

Prevention and treatment of SLE-like disease in (NZB× NZW)F1 mice with the hCDR1 or mCDR1 peptide. For prevention of SLE, mice at the age of 2 months, before disease manifestations are observed, were injected s.c. with hCDR1 (or mCDR1 in Example 12, 250 μg/mouse) once a week for 10 weeks. To treat an established disease, mice at the age of 5-7 months were injected with hCDR1 (in Example 12, mCDR1 s.c., 250 μg/mouse) once a week for 10 weeks.

Proliferative Responses. PBL were isolated from heparinized venous blood by Ficoll-Hypaque (Pharmacia) density-gradient centrifugation. All assays were performed, in triplicate, in flat-bottomed microtiter plates (Falcon, Becton Dickinson, Oxmard, Calif., USA) in which $2 \times 10^5$ PBL were cultured in enriched RPMI-1640 as described (Dayan et al., 2000). The PBL were exposed to various concentrations (0.1-40 μg/well) of the human anti-DNA 16/6Id mAb with and without the addition of the various CDR-based peptides at a concentration of at least 10-fold excess over that of the 16/6Id. Phytohemagglutinin (PHA; 2 μg/well) was used as a control for culture conditions at each experiment. The cultures were incubated in 7.5% $CO_2$ at 37° C. for 6 days. Eighteen hours before the cells were harvested, [$^3$H]-thymidine (0.5μ Ci of 5 Ci/mmol) (Nuclear Research Center, Negev, Israel) was added to all cultures. Results are expressed as the mean thymidine incorporation in counts per minute (CPM) of triplicate culture±SD, or as stimulation index (S.I.; the ratio of mean CPM at the optimal concentration of the human 16/6Id to the mean CPM in the presence of medium alone). A S.I.≧2 was considered a positive response (Dayan et al., 2000). Inhibition (the ratio of mean CPM in the presence of the 16/6Id and various CDR-based peptides to the mean CPM with the 16/6Id without the CDR-based peptide) above 50% was considered positive.

Induction of Cytokine Production. Mice that were immunized with the human 16/6Id mAb and either treated or not with the CDR-based peptide, were killed at different periods during or after treatment with the peptide. Splenocytes and lymph node cells (LNC) were harvested and incubated ($5 \times 10^6$/ml) in the presence of the 16/6Id. Supernatants were collected after 48 and 72 h.

Assessment of Cytokines in the Supernatants. Supernatants were collected 48 hours following the initiation of the cultures and stored at −70° C. Measurements of IL-2, IL-10, IFN-γ, and TNF-α were performed by ELISA by using the relevant standards, capture and detecting Abs (Pharmingen) according to the manufacturer's instructions. TGF-β was determined by an ELISA. Briefly, plates were coated with the recombinant human TGF-β1 sRIII/Fc chimera (R & D Systems Inc., Minneapolis, Minn., USA), and the second Ab used was the biotinylated anti-human TGF-β1 antibody (R & D Systems Inc.). The substrate solution used was TMB color Reagent (Helix Diagnostics, West Sacramento, Calif.), and enzyme activity was evaluated by using 570- and 630-nm filters.

Detection of SLE-Associated Clinical and Pathological Manifestations. Proteinuria was measured semiquantitatively by using Combistix kit (Ames Division, Bayer Diagnostics, Newbury, U.K.). White blood cells (WBC, for leukopenia) were counted after a 10-fold dilution of heparinized blood in distilled water containing 1% acetic acid (vol/vol). For immunohistology analysis, frozen kidney sections (6 μm) were fixed and stained with FITC-conjugated goat Abs to mouse IgG (γ-chain specific; Sigma).

ELISA. For measuring anti-DNA Abs, 96-well Maxisorb microtiter plates (Nunc) were coated with either methylated BSA or polyL-lysine (Sigma). The plates were then washed and coated with either 10 μg/ml of denatured calf thymus DNA (Sigma) or λ-phage double-stranded DNA (Boehringer Mannheim, 5 μg/ml). After incubation with different dilutions of sera, goat anti-mouse IgG (γ-chain specific) conjugated to horseradish peroxidase (Jackson ImmunoResearch) was added to the plates, followed by the addition of the substrate, 2,2'-azino-bis(3-ethylbenzthiazoline-6-sulfonic acid) (Sigma). Results were read by using an ELISA reader.

Measurement of activities of MMP-2 and MMP-9. MMP activity was tested by gelatin zymography. Pooled sera of individual mice of the different experimental groups were separated by an 8% SDS-PAGE polymerized with 1 mg/ml gelatin. Following electrophoresis, gels were washed once for 30 min in 2.5% Triton X-100 to remove the SDS, and once for 30 min in the reaction buffer containing 50 mM Tris-HCl, 200 mM NaCl, 10 mM $CaCl_2$ and 0.02% (w/v) Brij 35 (pH 7.5). The reaction buffer was changed to a fresh one, and the gels were incubated at 37° C. for 24 h. Gelatinolytic activity was visualized by staining the gels with 0.5% Coomassie brilliant blue.

Western blot analysis of MMP-3 in sera. Samples of 5 μl of each serum were loaded on 12% SDS/PAGE, separated under reducing conditions, and transferred to nitrocellulose. The blots were probed (0.5 μg/ml, 1 hr, room temperature) with anti-MMP-3 antibodies (Oncogene Research Products, Mass., USA) and developed using chemiluminescence.

Immunostaining of kidney sections for MMP-3 or MMP-9. For immunostaining of MMP-3 or MMP-9, kidney sections (5 μm) were fixed with cold acetone (5 min at room temperature), washed twice in PBS, permeabilized (1 min at room temperature) in 0.05% Triton X-100 (diluted in PBS), and washed twice in PBS. In order to get a specific anti-MMP staining and to avoid the staining of immune complex deposits by the FITC-labeled goat anti-mouse, kidney sections were blocked (1 hr at room temperature) with unlabeled goat anti-mouse IgG+IgM (diluted 1:1 in 1% BSA/PBS; (Jackson ImmunoResearch Laboratories) and washed 3 times with PBS containing 0.05% Tween. Monoclonal anti-MMP-9 (1:100; Chemicon International, Inc.) or anti-MMP-3 (1:50; Oncogene Research Products) antibody diluted in 1% BSA/PBS were added for 30 min, at room temperature. For all immunostaining procedures, FITC-labeled goat anti-mouse IgG+IgM (Jackson ImmunoResearch Laboratories), diluted 1:30 in 1% BSA/PBS (30 min at room temperature), was used.

Statistical analysis. Results are presented as mean±SD. Chi-square, Wilcoxon, Mann-Whitney and t-tests were employed for statistical analysis. $P \leq 0.05$ was considered significant.

Example 1

Synthesis of the Human Peptides hCDR1 and hCDR3

The human hCDR1 (SEQ ID NO:6) and hCDR3 (SEQ ID NO:7) peptides were prepared by methods well-known in the art, for example, by chemical solid phase or solution phase synthesis using an automated synthesizer by using the manufacturer's protocols for t-butyloxycarbonyl (t-Boc), fluorenylmethoxycarbonyl (Fmoc) or other alpha-amino acid protecting group procedure essentially as described (see, for example, Peptides: Synthesis, Structure and Applications, ed. by B. Gutte, Academic Press, 1995; Peptide Synthesis Protocols, ed. by M. Pennington and B. Dunn, Humana Press, 1994; Schnolzer M. et al., In situ neutralization in Boc-chemistry solid phase peptide synthesis. Rapid, high yield assembly of difficult sequences. Int. J. Pept. Protein Res. 40: 180-193, 1992).

Example 2

In Vivo Inhibition of Lymph Node Cell (LNC) Proliferation of Mice Immunized with mCDR1 and mCDR3 and Treated with hCDR1 and hCDR3

In order to determine the inhibitory efficacy of the human peptides hCDR1 and hCDR3, we first tested their ability to inhibit the in vivo priming of mice with the murine peptides mCDR1 and mCDR3.

To this end, BALB/c and SJL mice were immunized with mCDR1 and mCDR3, respectively. The immunizing murine peptides were injected (10 μg/mouse) in CFA intradermally in the hind footpads. Concomitant with the immunization, groups of BALB/c mice were injected subcutaneously (s.c.) with 200 μg in PBS of hCDR1 and groups of SJL mice were similarly injected with hCDR3. Ten days after the immunization, mice were sacrificed and their lymph nodes were harvested and the cells were tested for their ability to proliferate following triggering with the immunizing peptides. Briefly, LNCs of immunized mice ($0.5 \times 10^6$/well) were cultured (in triplicates) in the presence of different concentrations (1-20 μg/well) of the murine immunizing peptides in enriched RPMI-1640 medium supplemented with 1% normal mouse serum. Following four days of incubation, $^3$H-thymidine was added for additional 16 hours. Cells were then harvested and radioactivity was counted using a β-counter.

The results in Tables 1A and 1B represent the maximum % inhibition of proliferation of LNCs of mice immunized with mCDR1 and mCDR3 and treated with hCDR1 and hCDR3, respectively. The inhibition was calculated based on the proliferation of LNCs of mice that were not treated with the inhibitory peptides hCDR1 and hCDR3. It can be seen that hCDR1 and hCDR3 were capable of inhibiting the proliferative responses to the immunizing murine CDR peptides.

TABLE 1A

Inhibition by hCDR1 of the proliferation of BALB/c-derived LNCs to mCDR1

| Inhibitor | % Inhibition |
|---|---|
| hCDR1 | 55% |

TABLE 1B

Inhibition by hCDR3 of the proliferation of SJL-derived LNCs to mCDR3

| Inhibitor | % Inhibition |
|---|---|
| hCDR3 | 55% |

Example 3

In Vivo Inhibition of LNC Proliferation of Mice Immunized with the Human Anti-DNA 16/6Id mAB and Treated with hCDR1 and hCDR3

Because our aim was to test the inhibitory capacity of the peptides based on the CDR of the human 16/6Id autoantibody, it was of importance to find out whether peptides hCDR1 and hCDR3 are capable of inhibiting the priming to the whole molecule of the human 16/6Id mAb. To this end, BALB/c and SJL mice were primed with the human 16/6Id mAb (2 μg/mouse) in CFA intradermally in the hind footpads. The priming was done concomitant with the s.c. administration in PBS of 200 μg/mouse of hCDR1 to groups of BALB/c mice and of hCDR3 to SJL mice. Ten days following immunization, the mice were sacrificed and their LNCs were tested in vitro for their ability to proliferate to different concentrations (0.1-10 μg/well) of the human anti-DNA 16/6Id mAb.

Representative results of these experiments are shown in Tables 2A and 2B. The results are presented as maximum % inhibition of the proliferation to the immunizing human 16/6Id mAb of lymph node cells of mice immunized and treated with the peptides hCDR1 and hCDR3 as compared with mice that were immunized with the 16/6Id mAb but were not treated with the peptides. As can be seen, both peptides hCDR1 and hCDR3 were capable of inhibiting efficiently the priming to the human 16/6Id mAb.

TABLE 2A

Inhibition by hCDR1 of the proliferation of BALB/c-derived LNC to the human 16/6Id mAb.

| Inhibitor | % Inhibition |
|---|---|
| hCDR1 | 88% |

TABLE 2B

Inhibition by hCDR3 of the proliferation of SJL-derived LNC to the human 16/6Id mAb.

| Inhibitor | % Inhibition |
|---|---|
| hCDR3 | 68% |

Further experiments demonstrated that a nasal administration of as low as 10 or even 2 μg/mouse of the peptide hCDR1 or hCDR3, concomitant with the immunization with the human 16/6Id mAb, inhibited by up to 100% the proliferative responses of lymph node cells to the immunizing antibody.

In another experiment, BALB/c mice were immunized with 1 μg human 16/6Id in CFA, intradermally in the hind footpads, and either were injected with hCDR1 s.c., 300 μg/mouse in PBS, or were not further treated. Ten days later the mice were sacrificed and their LNC were tested for their ability to proliferate in vitro to the human 16/6Id. Thus, popliteal LNCs ($0.5 \times 10^6$) were incubated in the presence of various concentrations (0.1-10 μg/well) of the human anti-DNA 16/6Id mAb. At the end of 4 days incubation, $^3$H-thymidine was added to the cultures for the last 18 hours of incubation. Cells were then harvested and radioactivity counted.

FIG. 1 shows the results of such experiments and demonstrates that hCDR1 inhibited efficiently the proliferative responses of lymph node cells of the treated mice. The % inhibition of proliferation at the various concentrations of 16/6Id mAb was as follows: 0.1 μg/well—47%; 1 μg/well—66%; 5 μg/well—76%; and 10 μg/well—62%.

Figure 2:
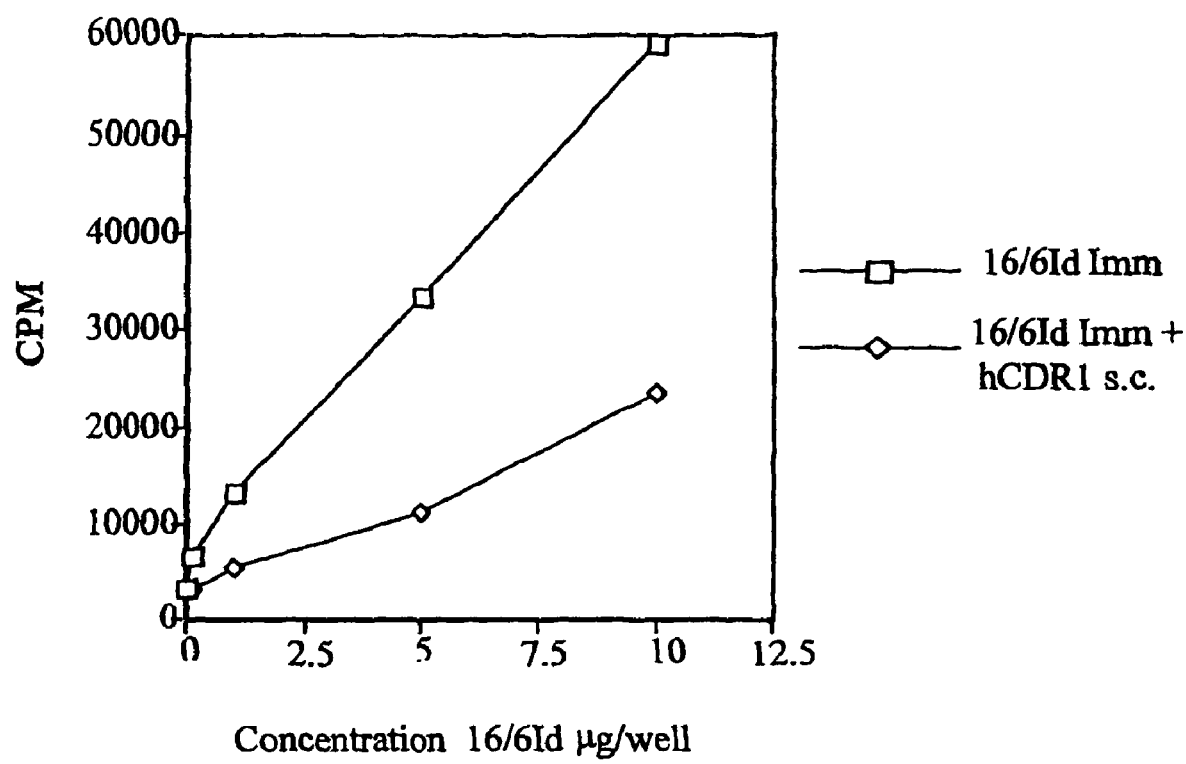
FIG. 2 shows inhibition of the proliferative responses of lymph node cells of mice immunized with human 16/6Id mAb to various concentrations of the 16/6Id mAb (0.1-10 μg/well), by treatment with 50 μg hCDR1.

The same experiment above was repeated with 50 μg hCDR1/mouse in PBS. FIG. 2 shows that hCDR1 is very effective in inhibiting the in vivo priming of mice with the whole anti-DNA 16/6Id macromolecule and even a s.c. injection with as little as 50 μg of hCDR1 inhibited significantly the ability of lymph node cells to proliferate to the 16/6Id autoantibody. The % inhibition of proliferation at the various concentrations of 16/6Id mAb was as follows: 0.1 μg/well—98%; 1 μg/well—76%; 5 μg/well—73%; and 10 μg/well—64%.

Example 4

Peptide hCDR1 Immunomodulates Cytokine Production

The lymph node cells of the BALB/c mice treated with 50 μg of hCDR1 of Example 3 were also stimulated with the human 16/6Id mAb for cytokine production and the supernatants were tested for cytokine (INF-γ TGF-β and IL-10) secretion, by ELISA.

Figure 3A:
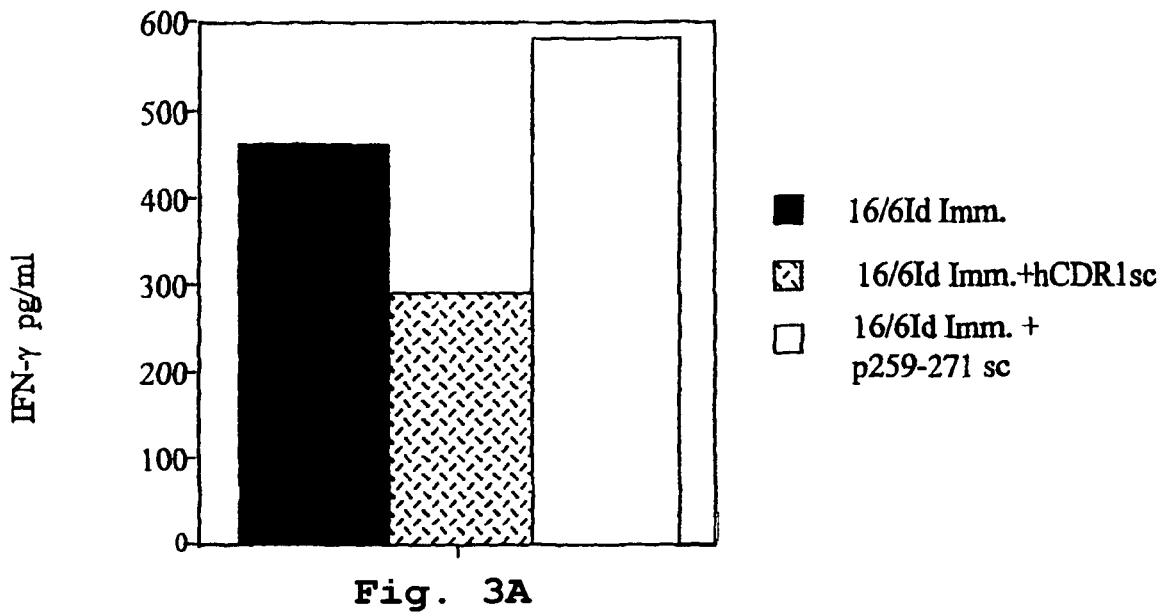
FIGS. 3A-C show the cytokine pattern in BALB/c mice immunized with human 16/6Id mAb and treated with hCDR1 or with an irrelevant peptide p259-271.
Figure 3B:
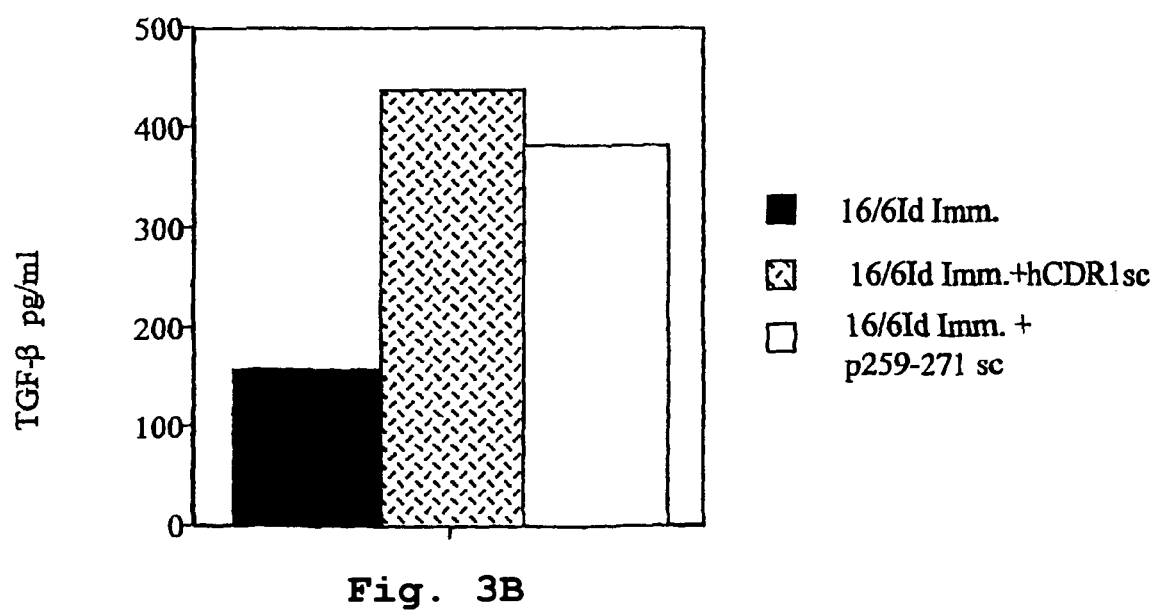
Figure 3:
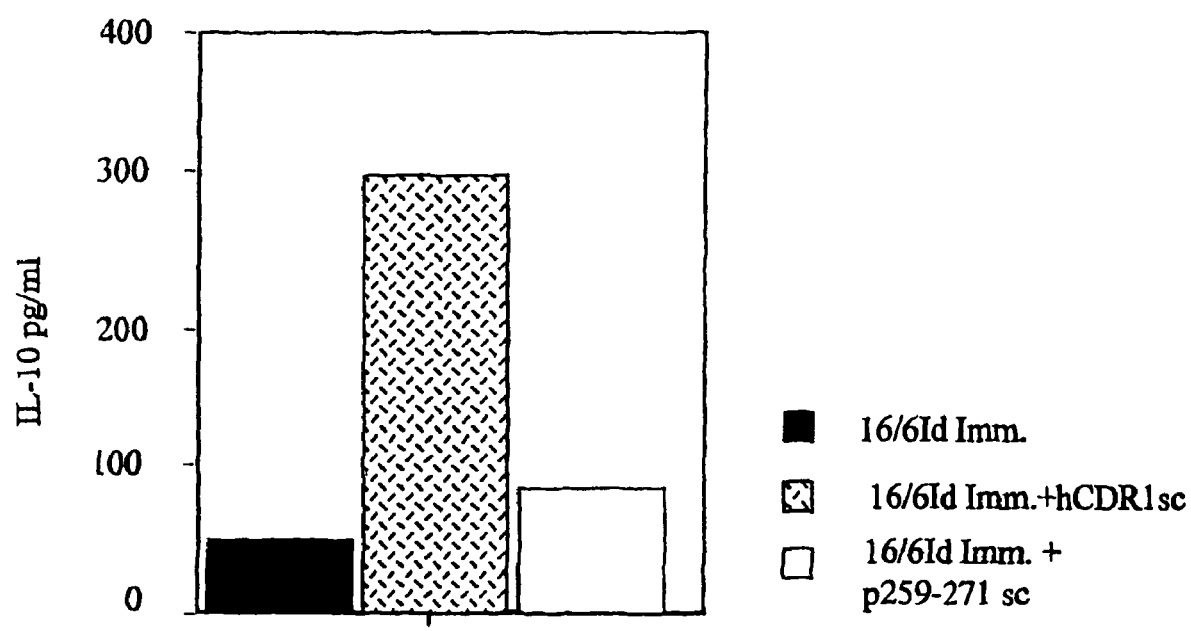

FIG. 3 shows results of a representative experiment. It can be seen that hCDR1 down-regulated the production of INF-γ (FIG. 3A) and up-regulated the secretion of TGF-β (FIG. 3B) and IL-10 (FIG. 3C). It should be noted that a peptide used as control (p259-271, that was shown to be a myasthenogenic peptide) did not affect significantly INF-γ and IL-10 production and was less effective in up-regulating TGF-β.

Example 5

Peptides hCDR1 and hCDR3 Inhibit the Proliferative Response of PBL of SLE Patients to the Human 16/6Id mAb Sixty-two patients, 9 males (14.5%) and 53 females (85.5%) with SLE participated in our study. The mean age at diagnosis was 32.95±12.92 (range 12-61) years and the mean follow-up period was 10.98±10.76 (range 1-32) years. All patients fulfilled at least 4 of the American College of Rheumatology (ACR) revised diagnostic criteria for SLE (Tan et al., 1982). Patients were recruited from three Israeli Medical Centers (Kaplan, Rehovot; Ichilov, Tel Aviv; Asaf-Harofeh, Rishon Lezion). Disease activity was determined according to the SLEDAI lupus activity index (Bombardier et al., 1992). A control group of 36 sex- and age-matched healthy control volunteers was studied concomitantly with the SLE patients. The study was approved by the Ethical Committee of the Medical Center.

It was of interest to investigate whether the peptides hCDR1 and hCDR3, which are based on the CDR1 and CDR3 of the human 16/6Id mAb, are capable of inhibiting the specific proliferative responses of PBL of SLE patients to the human 16/6Id mAb. To this end, we first had to identify the patients whose PBL could be stimulated to proliferate by the human 16/6Id mAb (responders).

Figure 4:
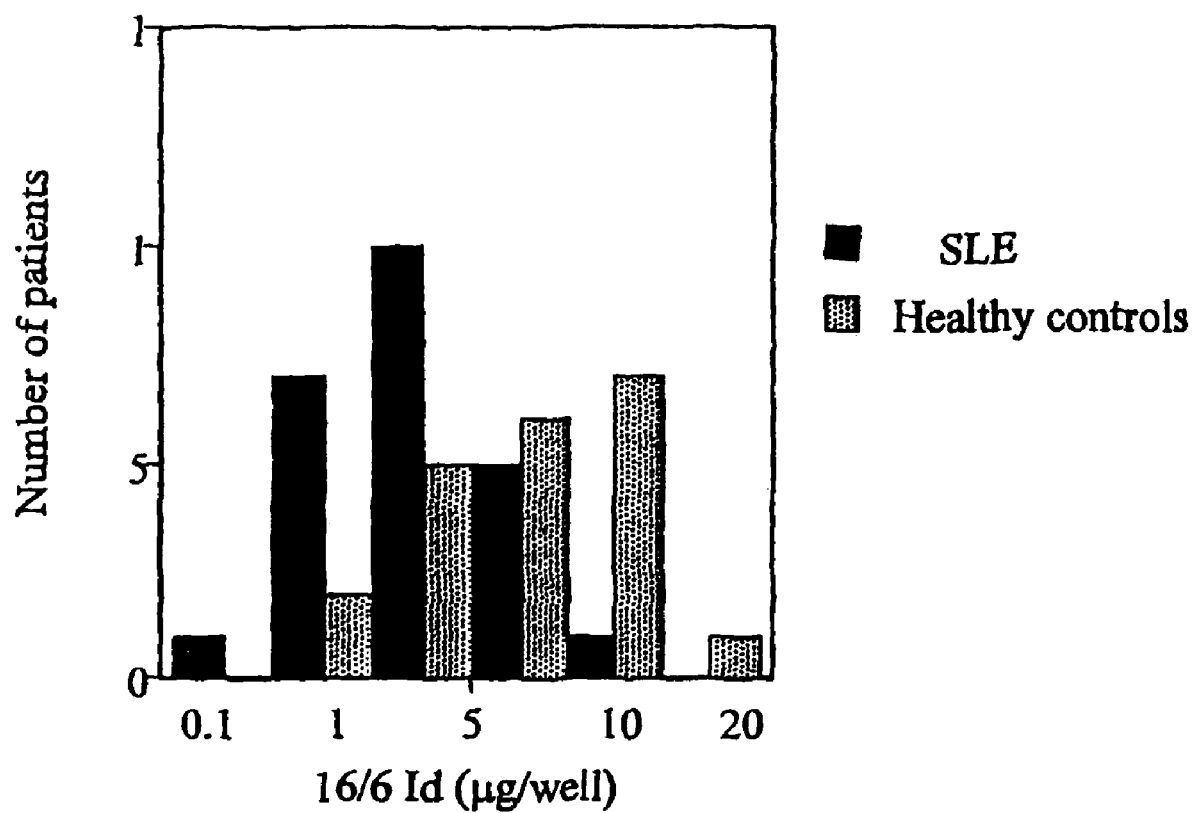
FIG. 4 shows the concentrations of the human anti-DNA 16/6Id mAb required for optimal stimulation of PBL of SLE patients and of healthy controls. PBL were stimulated with various concentrations (0.1-40 μg/well) of the 16/6Id mAb. The concentration yielding the highest stimulation index was defined as optimal for triggering a proliferative response.

Therefore, PBL of 62 consecutive SLE patients were cultured in the presence of the human 16/6Id and their proliferative responses and ability to secrete IL-2 were determined. PBL of 24 out of the total of 62 (39%) and of 23 out of 55 (42%) SLE patients tested responded (SI≧2, range 2-5.6) by proliferation and by IL-2 secretion (SI≧2, range 2-60), respectively. The frequency of responders in the group of SLE patients was lower than that observed in the group of healthy donors that was tested as control. Thus, PBL of 21 out of a total of 36 (58%) healthy donors responded by proliferation to the 16/6Id. The extent of proliferation (SI levels) was similar for the SLE patients and for the healthy controls who responded to the 16/6Id. However, as shown in FIG. 4, the optimal response to the 16/6Id of PBL of the control donors was observed at higher concentrations of 16/6Id as compared to the SLE patients.

No differences could be demonstrated between gender and age of SLE patients that responded to the 16/6Id and of the non-responder group of patients. However, the patients whose PBL proliferated in response to the 16/6Id were sick for a shorter period of time (a mean of 9.78±8.36 vs. 11.73±12.06 years for responders and non-responders, respectively; P≦0.036). Table 3 summarizes the clinical characterization of the 16/6Id responder and non-responder groups of SLE patients. As can be seen in the Table, both groups were similar in most SLE related clinical manifestations. The SLE disease activity score (SLEDAI) and the number of SLE diagnostic criteria were also similar in the two groups. Nevertheless, a higher frequency of neurological (both seizures and psychosis) and hematological involvement and a lower rate of renal involvement were noted in the responder group of patients in comparison to the group of non-responders. However, probably because of low number of patients in the relevant subgroups, the above differences did not reach statistical significance. Moreover, relatively less responder patients were determined between those treated with either steroids or cytotoxic agents at the time of the study. It is noteworthy that significantly more patients who never received steroids responded to the 16/6Id in comparison to the non-responder group (54% vs 21%; P=0.023).

It is noteworthy that the efficacy of the CDR-based peptides to inhibit the proliferative responses of PBL of healthy donors to the 16/6Id was much lower than that observed for PBL of SLE patients (not shown).

TABLE 3

Clinical and laboratory characterization of SLE patients.

|  | All Patients | Responders | Non-responders |
|---|---|---|---|
| A: Diagnostic Criteria* | | | |
| Number of Patients (%) | 62 (100) | 24 (39) | 38 (61) |
| Malar rash | 19/62 (30.1) | 8/24 (33.3) | 11/38 (29) |
| Discoid rash | 9/62 (15) | 3/24 (12.5) | 6/38 (16) |
| Photosensitivity | 21/62 (34) | 9/24 (37.5) | 12/38 (32) |
| Mucosal ulcers | 17/62 (27.4) | 8/24 (33.3) | 9/38 (23.7) |
| Arthritis | 46/62 (74.2) | 19/24 (79.2) | 27/38 (71) |
| Serositis | 14/62 (22.6) | 5/24 (20.8) | 9/38 (23.7) |
| Neurologic disorders‡ | 5/62 (8.1) | 4/24 (16.7) | 1/38 (2.7) |
| Renal disorder‡ | 24/62 (38.8) | 7/24 (29.2) | 17/38 (44.8) |
| Hematological Disorders‡ | 44/62 (71) | 19/24 (79.2) | 25/38 (65.8) |
| ANA | 61/62 (98.4) | 24/24 (100) | 37/38 (92.1) |
| α-dsDNA | 54/62 (87.1) | 19/24 (79.2) | 35/38 (92.1) |
| APLA | 35/62 (56.5) | 12/24 (50.0) | 23/38 (60.53) |
| B: Disease Activity | | | |
| SLEDAI Score | 6.65 ± 5.12 | 7.29 ± 1.06 | 6.24 ± 0.84 |
| Number of ACR diagnostic criteria | 5.44 ± 1.39 | 5.54 ± 0.33 | 5.34 ± 0.2 |
| C: Current treatment† | | | |
| NSAIDS | 17/62 (27.4) | 6/24 (25) | 11/38 (29) |
| Anti-Malarial | 37/62 (59.7) | 15/24 (62.5) | 22/38 (57.9) |
| Steroids‡ | 33/62 (53.2) | 11/24 (45.8) | 22/38 (57.9) |
| Cytotoxic‡ | 10/62 (16.1) | 2/24 (8.3) | 8/38 (21) |

*Clinical involvement was defined according to the ACR revised criteria. Anti-nuclear antibodies (ANA) and anti-dsDNA antibodies were determined by Hep2 cells and *Crithidia luciliae*, respectively. Anti-phospholipid antibodies (APLA) were defined as reactivity in one or more of the following assays: false positive VDRL, lupus anti-coagulant (LAC) or ELISA for anticardiolipin antibodies.
†The anti-malarial agent, hydroxychloroquine, was used at a dose of 200-400 mg/day; Steroid treatment was defined as a daily dose ≧5 mg of prednisone; cytotoxic agents used were cyclophosphamide (0.75-1.0 g/m²; monthly) or azathioprine (100-150 mg/day).
‡Parameters for which tendency was observed towards differences between the two groups of responder and non-responder SLE patients.

To test the ability of the peptides hCDR1 and hCDR3 to inhibit the proliferative response of PBL of SLE patients to the human 16/6Id mAb, PBL (2×10⁵/well) of SLE patients were stimulated in vitro in triplicates with different concentrations (0.1-20 μg/well) of the human 16/6Id mAb in the absence or presence of the peptides hCDR1 and hCDR3 (either 50 or 100 μg/well). Following 6 days of incubation, ³H-thymidine (0.5 μCi of 5 Ci/mmol) was added to each well for additional 18 hours of incubation. Cells were then harvested and radioactivity was counted using a β-counter. Results were expressed as mean counts per minute (cpm) of triplicate cultures. Stimulation indices (the ratio of mean cpm at the optimal concentration of 16/6Id to mean cpm without 16/6Id) were then calculated. A stimulation index (SI)≧2 was considered positive.

PBL of 24 out of the total of 62 (39%) SLE patients were found to proliferate to the 16/6Id mAb. The ability of the peptides hCDR1 and hCDR3 to inhibit the proliferative responses to the whole molecule of the 16/6Id autoantibody was tested on PBL of 19 responders SLE patients.

Table 4 shows the results of these experiments. Inhibition of above 50% of the proliferative capacity was considered positive. The Table represents the highest positive inhibition capacity for each peptide. It can be seen that the human hCDR1 and hCDR3 inhibited the proliferation of PBL of 16/19 (84.2%) and 15/19 (78.9%), respectively, of the 19 responders tested. Both peptides inhibited the proliferation of PBL of 18/19 (95%) of responders tested. It can also be seen in the Table that the magnitudes of inhibitions were similar for both peptides. Thus, it can be concluded that peptides based on CDR1 and CDR3 of the human 16/6Id mAb are efficient inhibitors of the proliferation of PBL of SLE patients to the human 16/6Id mAb.

TABLE 4

Inhibition of proliferation of PBL of SLE patients by peptides hCDR1 and hCDR3.

| | | Percent Inhibition | |
|---|---|---|---|
| Number | Initials | hCDR1 | hCDR3 |
| 1. | B. L. | 62 | <50 |
| 2. | M. D. | 70 | 75 |
| 3. | T. L. | 69 | <50 |
| 4. | Z. D. | <50 | <50 |
| 5. | N. N. | 88.5 | 87.5 |
| 6. | S. S. | 80 | 80 |
| 7. | S. H. | 76 | 70.4 |
| 8. | S. D. | 58 | 56 |
| 9. | A. N. | 69.5 | 65 |
| 10. | I. J. | 68.2 | 71.8 |
| 11. | L. J. | <50 | 72 |
| 12. | V. L. | 82 | 86 |
| 13. | M. S. | 63 | 64 |
| 14. | D. S. | 56 | 74 |
| 15. | Z. A. | 63 | 69 |
| 16. | B. M. | <50 | 68 |
| 17. | S. N. | 70.5 | 77.8 |
| 18. | G. M. | 51.5 | <50 |
| 19. | N. J. | 63 | 60.8 |
| Mean ± SD | | 68.12 ± 9.57 | 71.82 ± 8.44 |

Example 6

Specificity of the Inhibitory Capacity of hCDR1 and hCDR3

Figure 5:
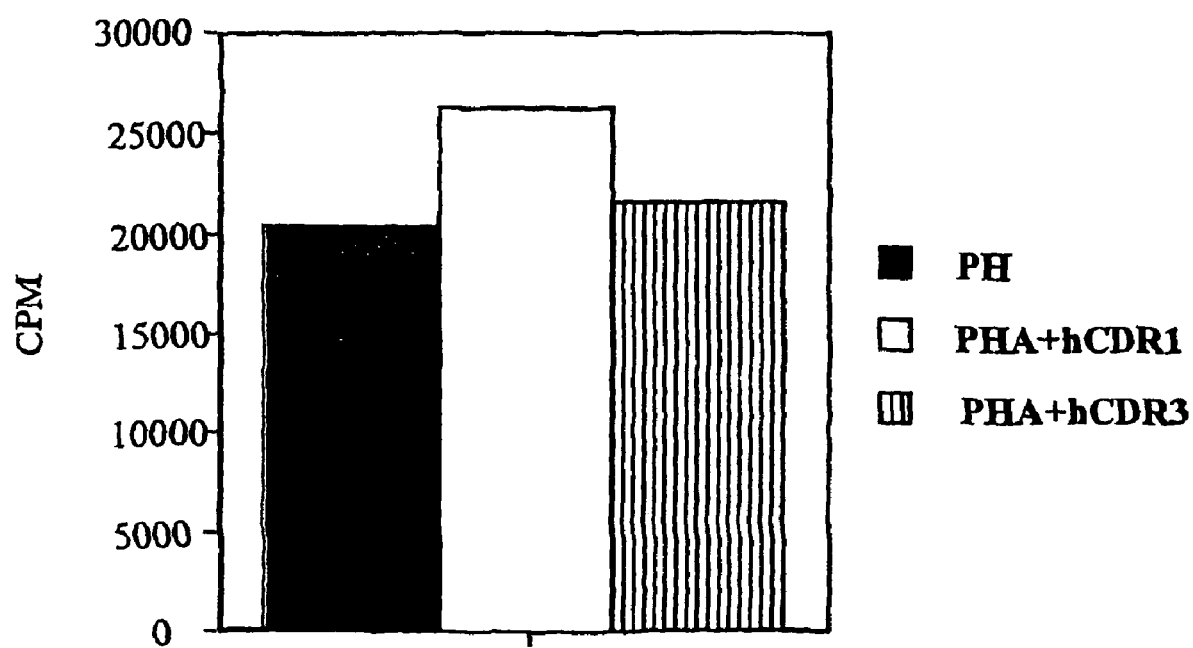
FIG. 5 shows proliferation of PBL from one SLE patient stimulated with the mitogen phytohemagglutinin (PHA) in the absence or presence of hCDR1 or hCDR3.

It is important to demonstrate that the inhibitory effects of the hCDR-based peptides are specific to SLE-associated responses. To this end the peptides hCDR1 or hCDR3 were added to cultures of PBL of SLE patients that were stimulated with the mitogen phytohemagglutinin (PHA, 2 μg/ml). The results of such an experiment performed with PBL of one SLE patient is shown in FIG. 5. The peptides hCDR1 and hCDR3 could not inhibit the proliferative responses (expressed in cpm) of the PBL to the mitogen PHA and the proliferative responses were similarly high in the absence (black column) or presence of either hCDR1 or hCDR3.

Figure 6:
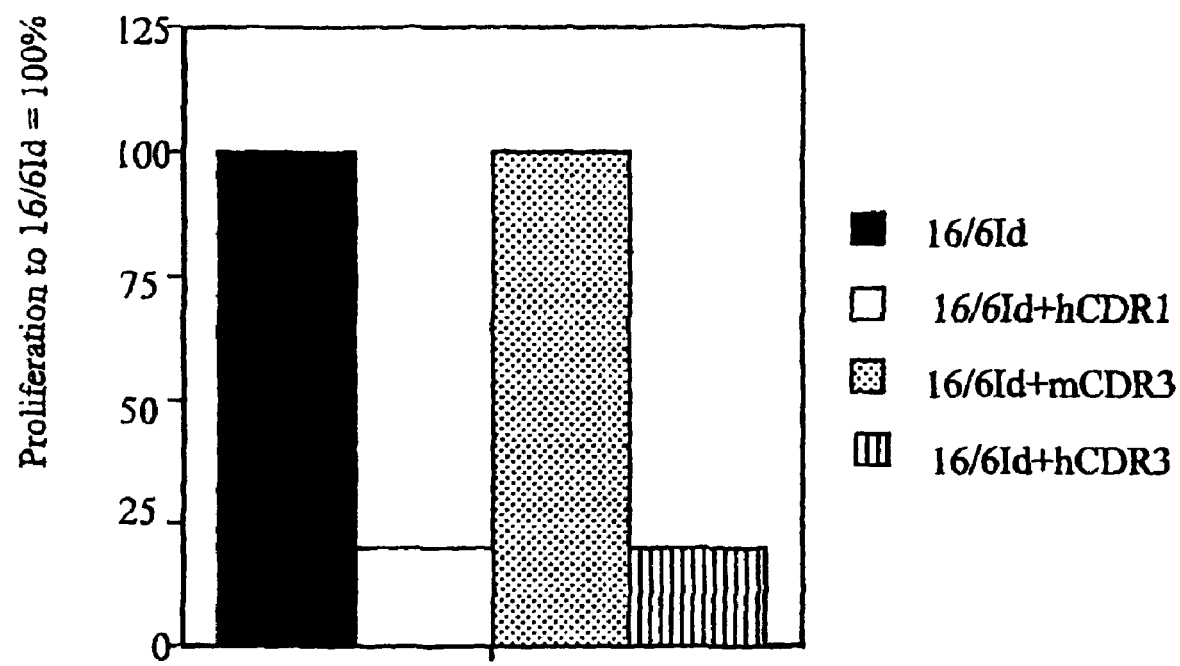
FIG. 6 shows proliferation of PBL from one SLE patient stimulated with human 16/6Id mAb in the absence or presence of the human peptides hCDR1 or hCDR3 or the murine peptide mCDR3.

In another experiment, cultures of PBL of SLE patients were stimulated with the human 16/6Id mAb and then incubated with the human peptides hCDR1 or hCDR3 or with the murine peptide mCDR3 as a control. The results of such an experiment performed with PBL of one SLE patient are shown in FIG. 6. As shown in FIG. 6, whereas both peptides hCDR1 and hCDR3 based on the human autoantibody inhibited efficiently the proliferative responses of PBL to the human 16/6Id mAb, the peptide mCDR3 based on the CDR3 of the murine antibody did not inhibit the proliferation.

Figure 7:
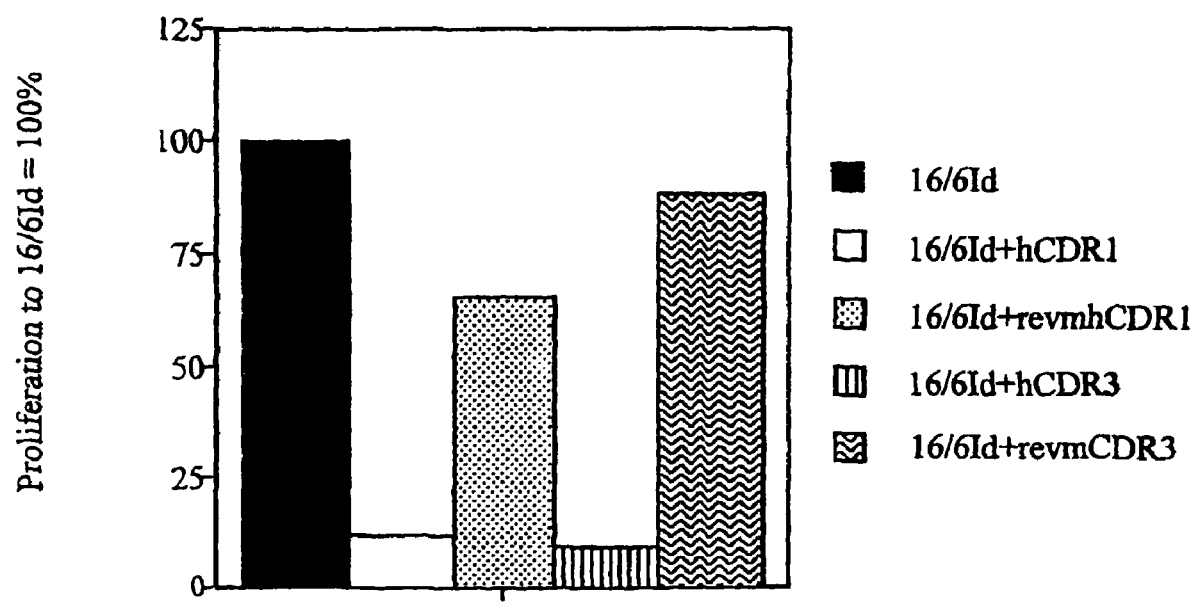
FIG. 7 shows proliferation of PBL from one SLE patient stimulated with human 16/6Id mAb in the absence or presence of the human peptides hCDR1 or hCDR3 or the murine reversed peptides revmCDR1 and revmCDR3.

Two additional control peptides were used in these experiments, namely peptides synthesized at the reversed order of the murine mCDR1 and mCDR3 peptides (revmCDR1 and revmCDR3), and the results are shown in FIG. 7. It can be seen that the two reversed peptides failed to inhibit significantly the proliferative responses of the PBL of the SLE patient to human 16/6Id mAb while peptides hCDR1 and hCDR3 did inhibit efficiently the proliferation, demonstrating that the inhibition of proliferation by the human hCDR-based peptides is specific to the peptides and to the SLE-associated T cell responses.

Example 7

Down-Regulation of the Secretion of IL-2 by PBL of SLE Patients in the Presence of the Peptides hCDR1 and hCDR3

It was of interest to find out whether the hCDR peptides are capable of inhibiting IL-2 secretion by PBL of SLE patients following stimulation with the human 16/6Id mAb. Such inhibition might also suggest that the human CDR-based peptides inhibit the proliferative responses to the 16/6Id mAb at least partially by down-regulating IL-2 secretion. To this end, PBL of SLE patients were incubated with the human 16/6Id mAb in the absence or presence of the peptides hCDR1 or hCDR3. Supernatants of the cultures were collected following 48 hours of incubation. Assays to determine levels of IL-2 in the supernatants were performed using the CTLL IL-2 dependent line. Briefly, cells of the CTLL line ($2 \times 10^4$/well) were incubated in the presence of the different supernatants for 24 hours, followed by the addition of $^3$H-thymidine for an additional 18-hour incubation period. Cells were then harvested and radioactivity counted using a β-counter. Results were calculated based on recombinant human IL-2 used as a standard. The ability of the peptides to inhibit the IL-2 secretion of PBL of 23 responders stimulated by the human 16/6Id was tested. The results, summarized in Table 5, show that hCDR1 and hCDR3 inhibited the secretion of IL-2 by PBL of 21/23 and 19/23 patients, respectively. Inhibition of proliferative responses of PBL directly correlated with IL-2 inhibition by the CDR-based peptides. Thus, inhibition of IL-2 secretion was observed in all cases where inhibition of proliferation were determined.

Figure 8:
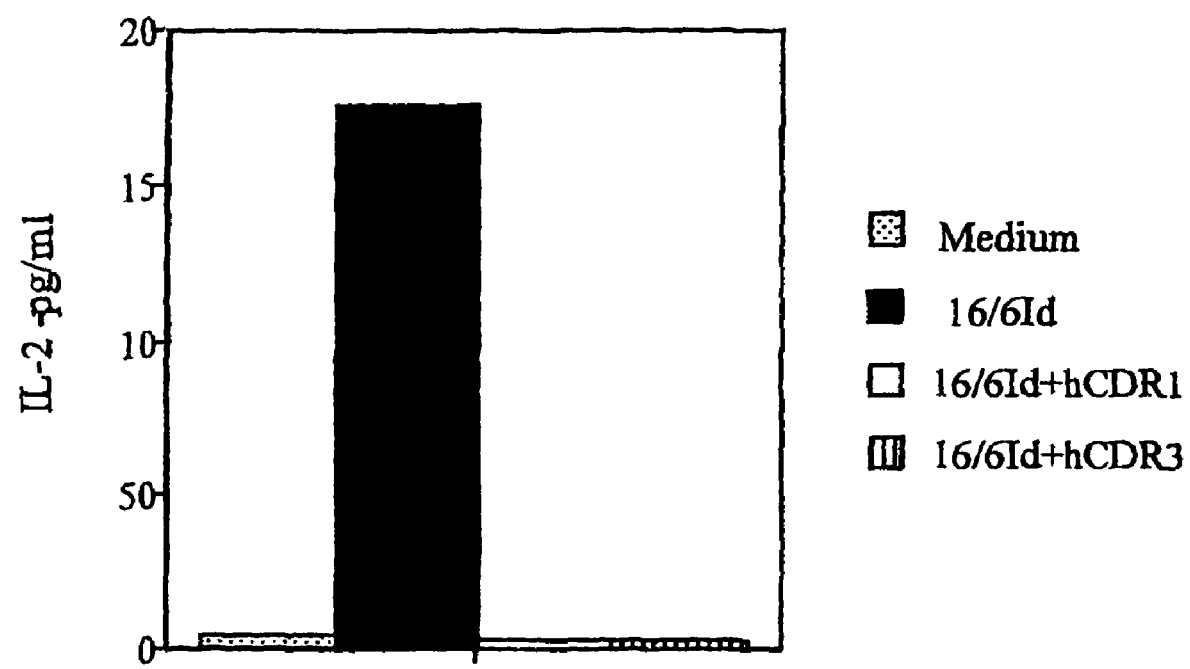
FIG. 8 shows inhibition of IL-2 secretion in PBL of SLE patients triggered by the human 16/6Id mAb in the absence or presence of hCDR1 or hCDR3.

The results obtained with PBL of one SLE patient represented in FIG. 8 (secretion of IL-2 is expressed in pg/ml) show that both hCDR1 and hCDR3 inhibited 100% of the IL-2 secretion by PBL of a SLE patient triggered by the human 16/6Id mAb.

TABLE 5

Inhibition of IL-2 secretion by hCDR1 and hCDR3

| Peptide | Inhibitory Activity* % | Maximum inhibition % |
|---|---|---|
| hCDR1 | 91 (21/23) | 84 ± 31 |
| hCDR3 | 83 (19/23) | 78 ± 34 |

*IL-2 secretion in the presence of 16/6 Id alone was considered as 100%. Inhibition of 50% or more was considered significant.

Example 8

Up-Regulation of the Secretion of the Immunosuppressive Cytokine TGF-β by CDR-Based Peptides In attempts to shed light on the mechanisms by which the human CDR-based peptides inhibit the proliferative responses to the human monoclonal anti-DNA 16/6Id antibody, the levels of the immunosuppressive cytokine TGF-β in the supernatants of the cell cultures were determined. The rationale behind these experiments is based on our previous findings of elevated levels of TGF-β in cultures of splenocytes of mice with SLE either induced with the human anti-DNA 16/6Id mAb or spontaneous {(NZBxNZW) F1 mice} following treatment with the peptides based on mouse CDR (Eilat et al., 2001). The elevation in the levels of TGF-β correlated with amelioration of disease manifestations in the treated mice.

For this purpose, supernatants were removed from cultures of PBL of various SLE patients following 48 hours incubation with the human 16/6Id mAb in the absence or presence of the peptides hCDR1 or hCDR3. TGF-β was determined by ELISA according to the manufacturer's instructions. Briefly, Maxisorb plates (Nunc) were coated with recombinant human TGFβsRII/Fc chimera (R&D Systems) diluted in PBS (100 ng/ml). After blocking, cell supernatants were added. After 18 hours incubation the detecting biotinylated anti-human TGF-β antibody (R&D Systems) was added. The substrate solution used was the TMB Colour Reagent (Helix Diagnostics) and enzyme activity was evaluated by the MRX ELISA reader using the 570 nm and 630 nm filters. The results are summarized in Table 6.

Figure 9:
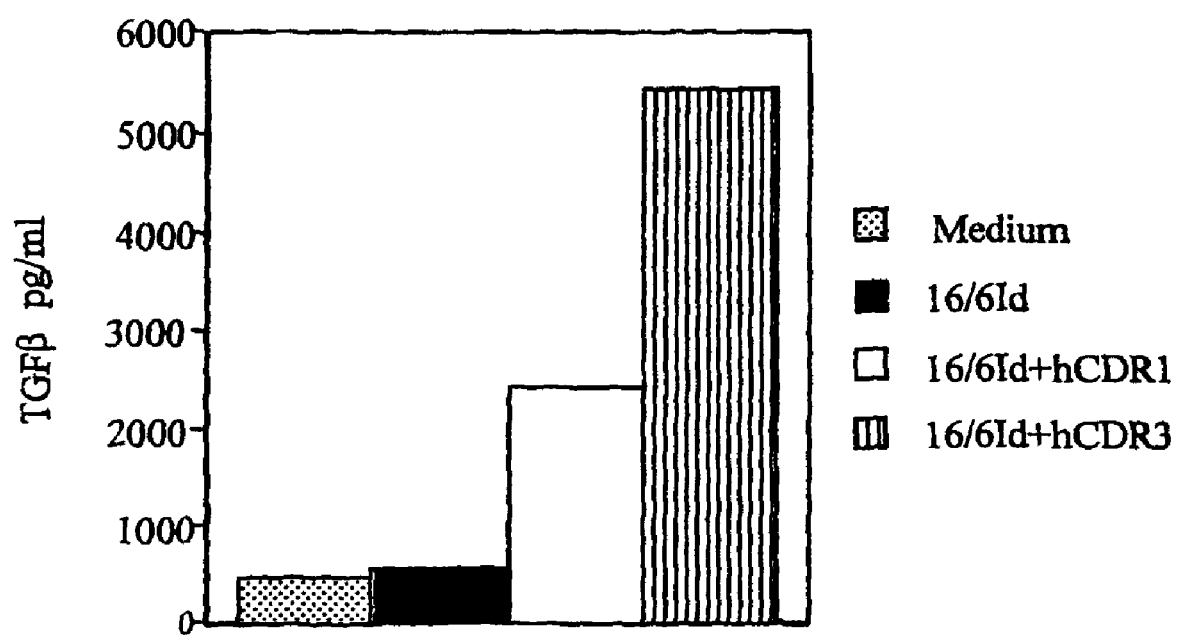
FIG. 9 shows up-regulation of TGF-β, secretion in the PBL of one representative SLE patient stimulated with the human 16/6Id mAb in the absence or presence of hCDR1 or hCDR3.

The results in FIG. 9 demonstrate that peptides hCDR1 and hCDR3 triggered a significant up-regulation in the secretion of TGF-β (expressed in pg/ml) by the PBL of one representative SLE patient that were stimulated with the pathogenic human 16/6Id mAb.

TABLE 6

Up-regulation of TGF-β secretion of 16/6 Id-induced stimulation of PBL of SLE patients with hCDR1 and hCDR3 peptides.

| Peptide | Up-regulation of TGF-β % | Maximum Up-regulation % |
|---|---|---|
| hCDR1 | 100 (19/19) | 305 ± 221 |
| hCDR3 | 100 (19/19) | 338 ± 242 |

Secretion of TGF-β in the presence of 16/6 Id alone (mean 636 ± 25 pg/ml) was considered as 100%. Results are expressed as percent secretion above that in the presence of 16/6Id alone.

Example 9

Immunomodulation of SLE Manifestations in Mice by hCDR1: Amelioration of Disease Manifestations Following Treatment of (NZBxNZW)F1 Mice with hCDR1

As shown above, the peptides based on the CDR of the human anti-DNA 16/6Id mAb were capable of inhibiting the priming of lymph node cells to the 16/6Id mAb and the proliferative responses of PBL of SLE patients to the 16/6Id mAb with similar efficiency. It was thus of interest to find out if these peptides can immunomodulate an SLE-like disease in animal models.

The experiments aimed at addressing the ability of the human peptides to treat an established SLE disease were performed first with the hCDR1 peptide. To this end, a few experiments were designed in which SLE-prone (NZB× NZW)F1 mice were treated with the hCDR1 peptide at the age of 5 and a half months, when manifestations of the SLE-like disease (anti-dsDNA, proteinuria, etc) are already observed. The hCDR1 peptide was administered in PBS s.c. weekly, for 10 weeks. The efficacy of different doses (50, 100 and 200 μg/mouse) of the hCDR1 peptide was tested. Control groups were injected with the vehicle PBS. The treatment led to a moderate reduction in the anti-dsDNA autoantibody titers. Thus, at a 1:1250 sera dilutions, O.D. values of 0.586±0.1, 0.27±0.1, 0.37±0.1 and 0.29±0.1 were measured at the end of the treatment for sera of PBS-treated mice, mice treated with 50 μg/mouse, 100 μg/mouse and 200 μg/mouse hCDR1, respectively.

We performed another experiment in which 7-month old (NZB×NZW)F1 mice were treated weekly for 10 weeks with 300 μg of hCDR1 injected s.c. in PBS. A mild reduction in the anti-DNA antibody titers could be observed in sera of hCDR1-treated mice. Nevertheless, Table 7 shows that treatment with hCDR1 resulted in a reduction in proteinuria and in a significant decrease in the immune complex deposits (ICDs) in the kidneys of the treated mice. The results in the Table express the intensity of ICDs where 0=no ICD; 1=moderate ICD; 2=severe ICD and 3=severe and extremely intense ICD.

TABLE 7

Clinical manifestations of (NZB × NZW)F1 mice treated with hCDR1 at the age of 7 months

| Treatment | Proteinuria g/L ± SEM | Immune Complex Deposits ± SEM |
|---|---|---|
| Untreated | 4.80 ± 2.56 | 2.57 ± 0.29 |
| hCDR1 300 μg/mouse | 1.08 ± 0.38 | 1.44 ± 0.41 p = 0.035 | p was calculated in comparison to untreated group of mice.

We then performed an additional experiment using 400 μg/mouse of hCDR1 to find out if more beneficial effects can be achieved by increasing the dose of the peptide. Treatment with 400 μg/mouse of hCDR1 had no greater effect on the anti-DNA antibody titers and, as can be seen in Table 8, the effect on the kidney disease was similar to that observed following treatment with the 300 μg dose.

TABLE 8

Clinical manifestations of (NZB × NZW)F1 mice treated with hCDR1 at the age of 6 months

| Treatment | Proteinuria g/L ± SEM | Immune Complex Deposits ± SEM |
|---|---|---|
| Untreated | 4.99 ± 2.53 | 2 ± 0.29 |
| hCDR1 400 μg/mouse | 0.77 ± 0.32 | 1.42 ± 0.19 p = 0.05 | p was calculated in comparison to untreated group of mice.

Figure 10:
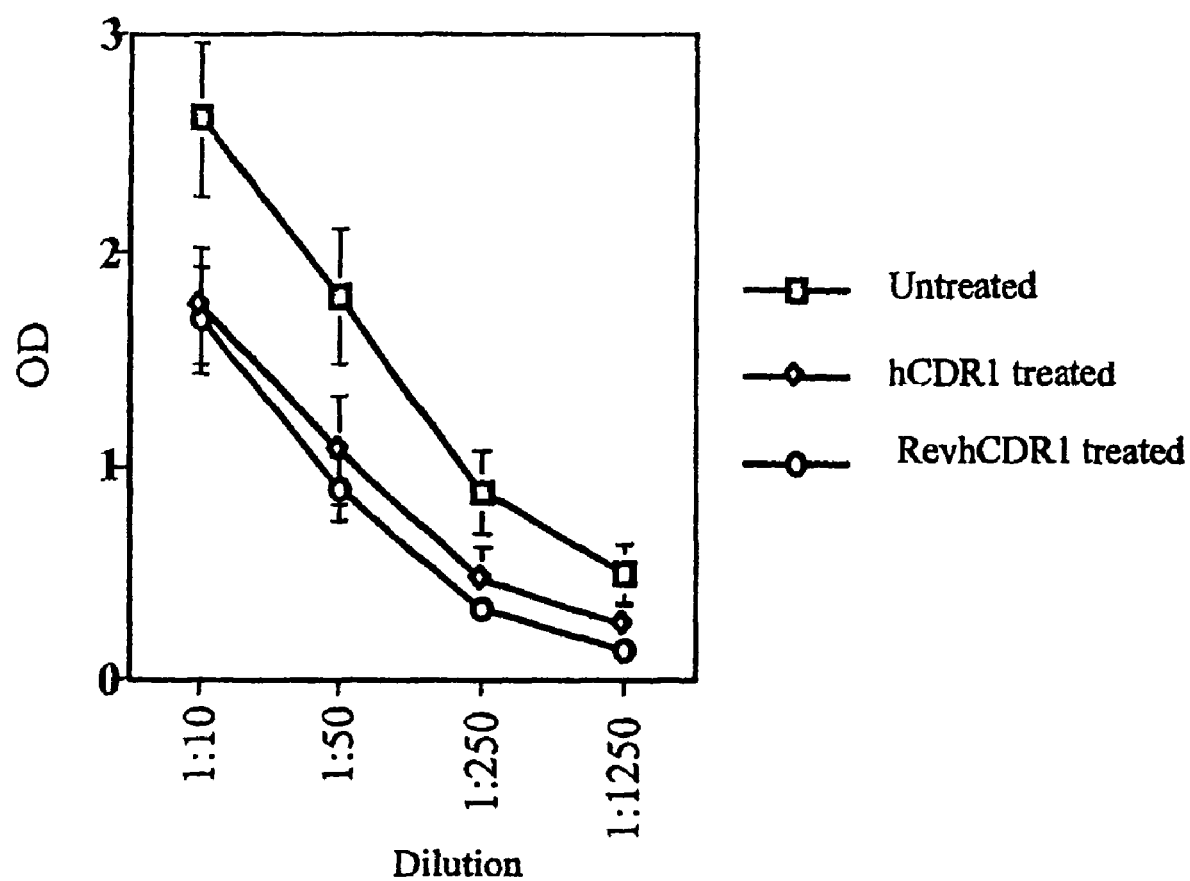
FIG. 10 shows anti-DNA autoantibody levels in (NZB×NZW)F1 mice untreated or treated with 300 μg hCDR1 or with the reversed peptide revhCDR1 (used as control).

We have therefore performed an additional experiment in which mice were treated with 300 μg of hCDR1 at the age of 7 months and used a control peptide, namely, the reversed hCDR1. The aim of the experiment was to find out if, in addition to the amelioration in the clinical manifestations, treatment with hCDR1 immunomodulates cytokine production, FIG. 10 demonstrates the mild reduction in anti-DNA autoantibody levels. Table 9 shows the proteinuria measured at different time points.

TABLE 9

Clinical manifestations of (NZB × NZW)F1 mice treated with hCDR1 at the age of 7 months

| | Proteinuria g/L ± SEM Following treatment No: | | |
|---|---|---|---|
| Treatment | 5 | 7 | 9 |
| Untreated | 2.65 ± 1.76 | 3.89 ± 2.73 | 7.55 ± 3.95 |
| hCDR1 300 μg/mouse | 0.61 ± 0.23 | 0.65 ± 0.32 | 1.02 ± 0.39 p = 0.05 |
| revhCDR1 300 μg/mouse | 6.94 ± 2.53 | 6.76 ± 2.91 | 5.99 ± 3.08 |

The effect of the treatment with hCDR1 can be seen at all measurements. Kidney damage is one of the main manifestations of the SLE-like disease in the (NZB×NZW)F1 mice. Ten-week treatment with the hCDR1 peptide reduced significantly the kidney disease. The 50 μg dose was less efficient than the 100 and 200 μg doses in treating the kidney disease. The latter two doses were similarly efficient.

Figure 11A:
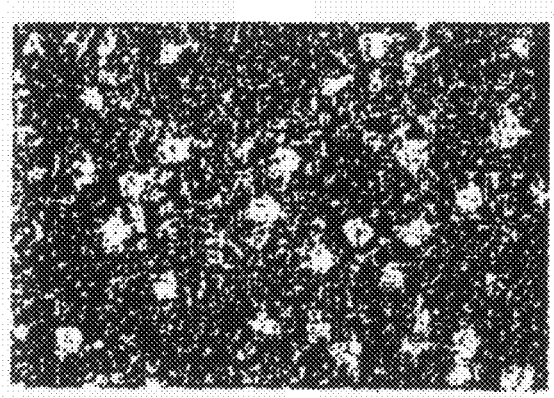
FIGS. 11A-11D are photos showing representative kidney sections of SLE-prone (NZB×NZW)F1 mice that were treated starting at the age of 5 and half months with PBS (11A, 11B) or with 100 μg hCDR1 (11C, 11D). The sections are of mice sacrificed at the age of 9 months. For the detection of Ig deposits, sections were incubated with FITC-conjugated goat anti-mouse IgG (γ chain specific) (11A, 11C×100; 11B, 11D×400).
Figure 11B:
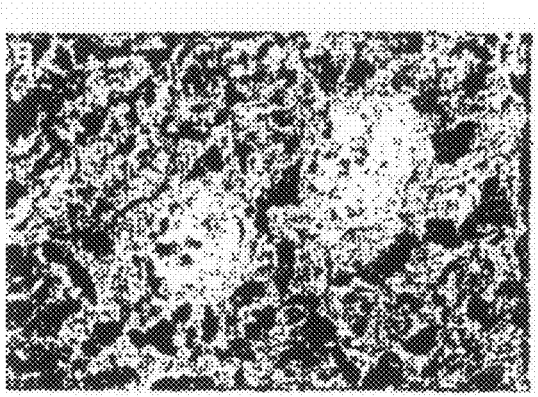
Figure 11C:
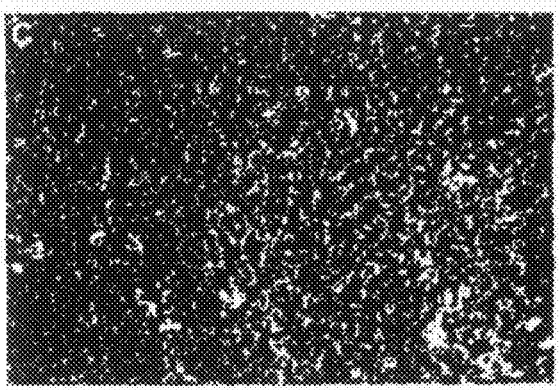
Figure 11D:
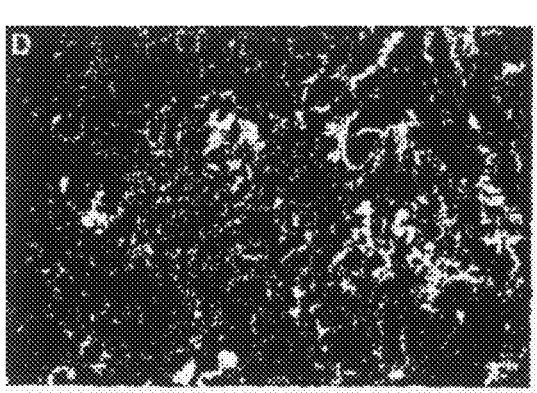
Figure 12A:
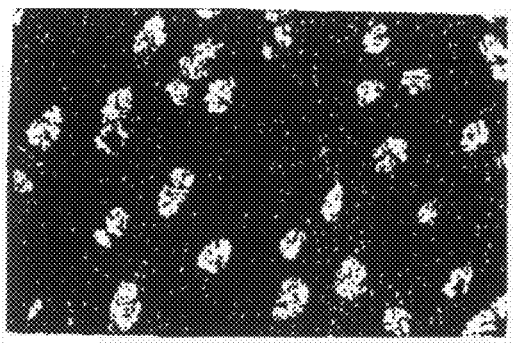
FIGS. 12A-12F are photos showing representative kidney sections of SLE-prone (NZB×NZW)F1 mice that were treated with PBS (12A, 12B) or with 300 μg hCDR1 (12C, 12D), or with the reversed peptide revhCDR1 (12E, 12F). The sections are of mice sacrificed at the age of 9 months. For the detection of immune complex Ig deposits, sections were incubated with FITC-conjugated goat anti-mouse IgG (γ chain specific) (12A, 12C, 12E×100; 12B, 12D, 12F×400).
Figure 12B:
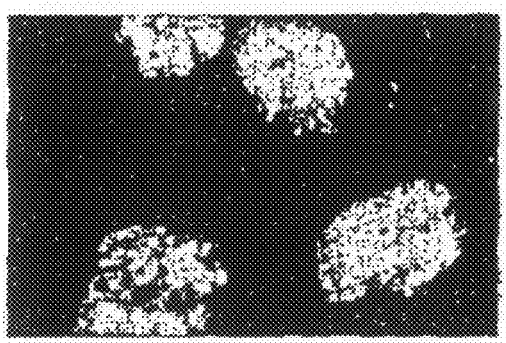
Figure 12C:
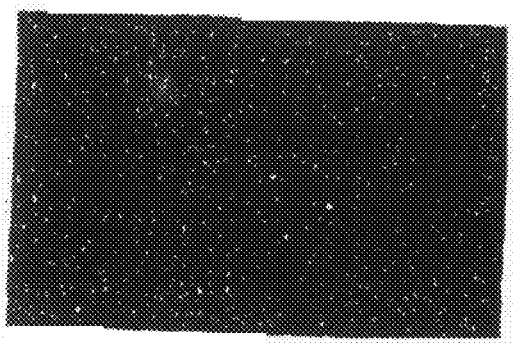
Figure 12D:
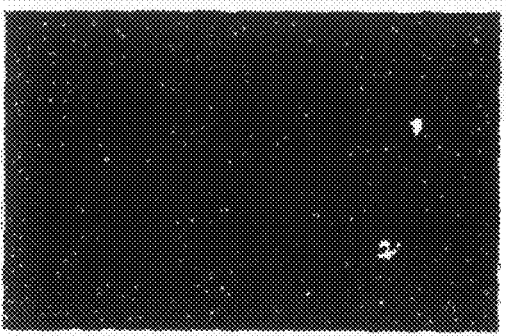
Figure 12E:
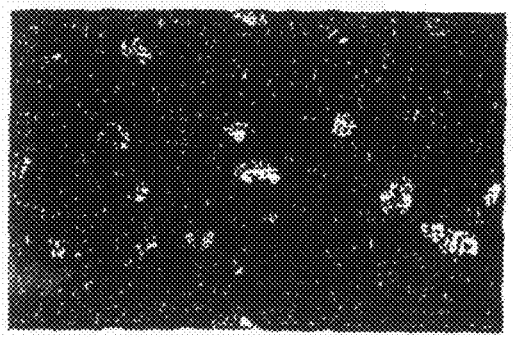
Figure 12F:
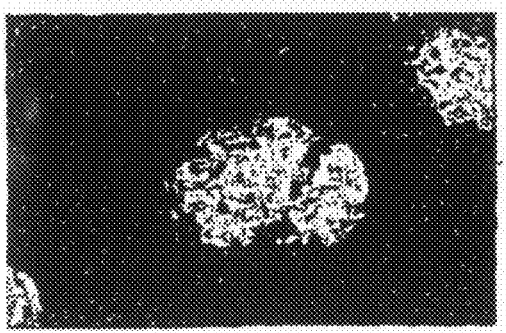

FIGS. 11A-11D are photos showing representative kidney sections of mice treated with the 100 μg dose of hCDR1. Thus, mice at the age of 9 months were sacrificed and their kidneys were removed and frozen immediately in liquid nitrogen. Frozen cryostat sections of 5 μm were air dried and fixed in acetone. For the detection of Ig deposits, sections were incubated with FITC-conjugated goat anti-mouse IgG (γ-chain specific). FIGS. 11A and 11B show kidney sections of a mouse of the PBS-treated group (control) whereas FIGS. 11C and 11D show kidney sections of a mouse treated with 100 μg of hCDR1. It can be seen in the figures that the treatment reduced the number of immune complexes as well as their intensity (11A, 11C×100; 11B, 11D×400).

Similar results were obtained when groups of (NZB× NZW)F1 mice were treated with hCDR1 at the age of 7 months when their full blown disease is already observed. The mice were treated for 10 weeks with either 100 μg/mouse or 300 μg/mouse. Treatment with both doses led to a moderate reduction in the anti-DNA autoantibody titers, similar to the above described results. A reduction in proteinuria in comparison to the PBS-treated group was measured as well. The kidney disease was ameliorated following treatment with both doses; nevertheless, a more significant effect was determined in the group of mice treated with the 300 μg dose. FIGS. 12A-12F are representative mouse kidney sections of each group where A, B represent an untreated mouse; C, D represent a kidney of a hCDR1-treated mouse and E, F represent a kidney section of a mouse treated with the reversed hCDR1. A, C, E×100 and B, D, F×400.

Figure 13:
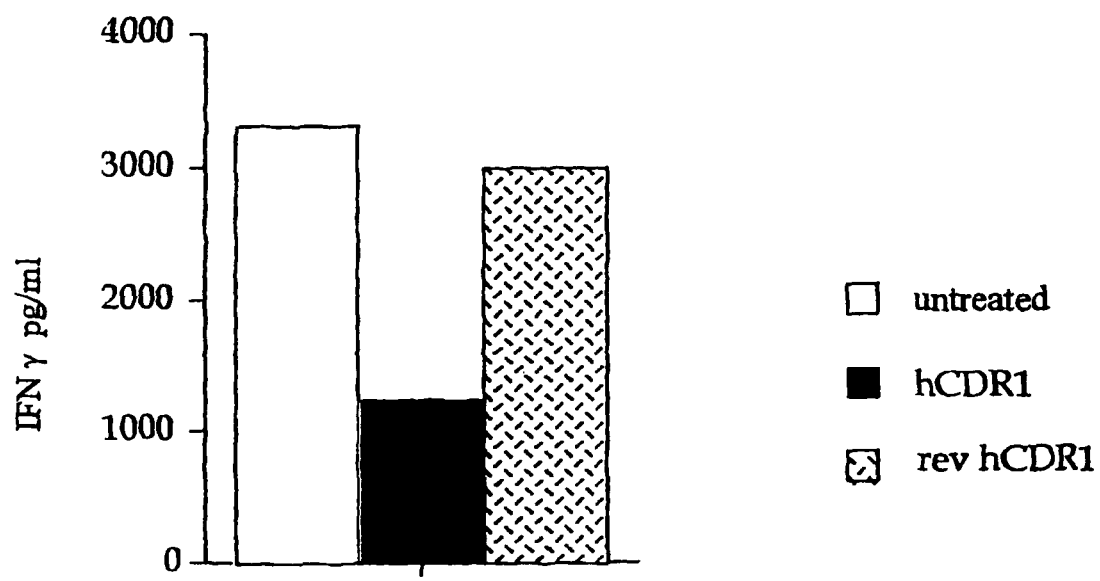
FIGS. 13A-13C show the cytokine pattern as measured by ELISA in supernatants of Con A-stimulated cultures of splenocytes of SLE-prone (NZB×NZW)F1 mice that were untreated or treated with hCDR1 or with the reversed peptide revhCDR1.
Figure 13:
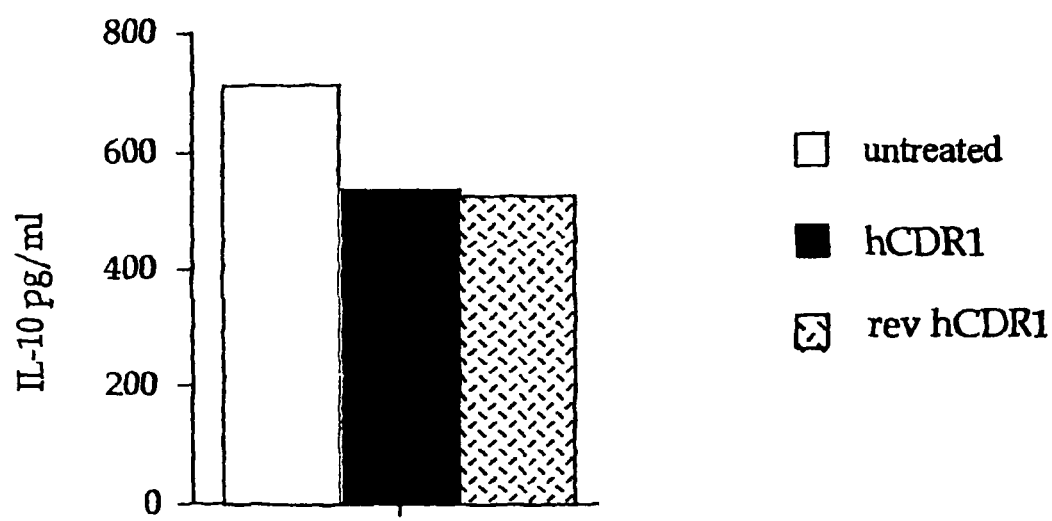
Figure 13:
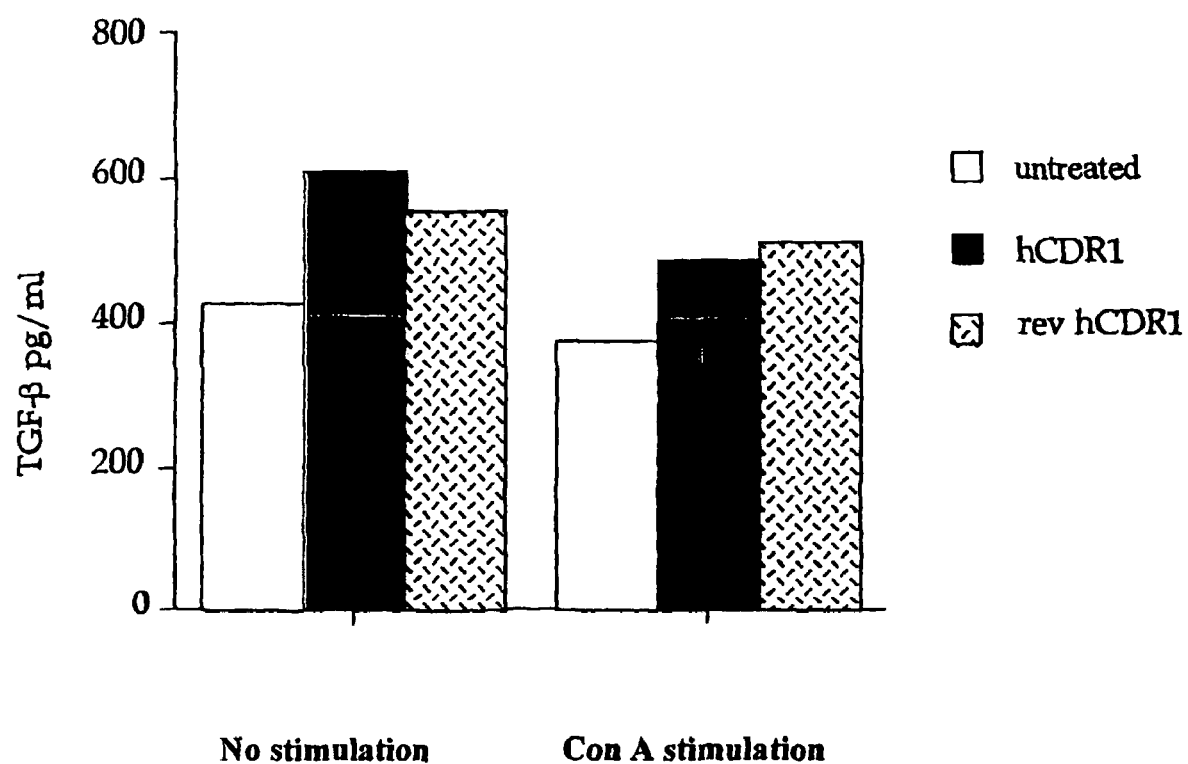
Figure 14A:
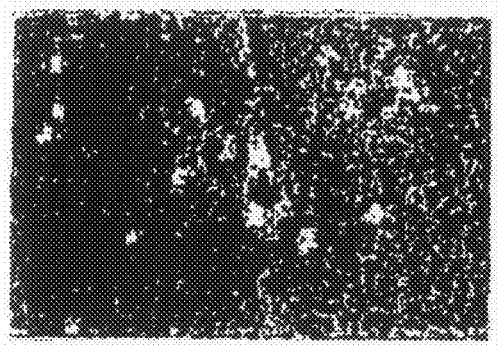
FIGS. 14A-14F are photos showing representative kidney sections of BALB/c mice with 16/6Id-induced experimental SLE treated with PBS (14A, 14B) or with 200 μg hCDR1 (14C, 14D), or with the reversed peptide revhCDR1 (14E, 14F). The sections are of mice sacrificed at the age of 9 months. For the detection of immune complex Ig deposits, sections were incubated with FITC-conjugated goat anti-mouse IgG (γ chain specific) (14A, 14C, 14E×100; 14B, 14D, 14F×400).
Figure 14B:
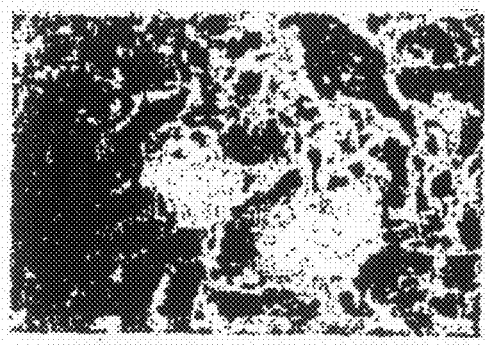
Figure 14C:
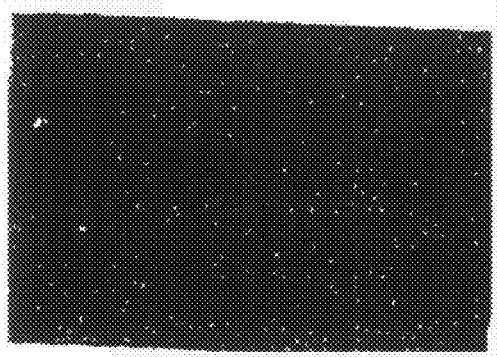
Figure 14D:
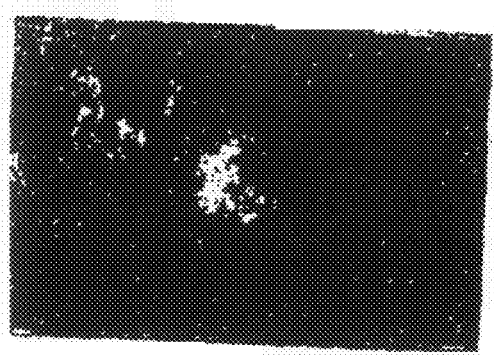
Figure 14E:
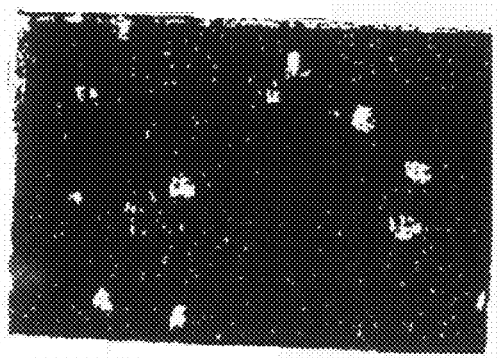
Figure 14F:
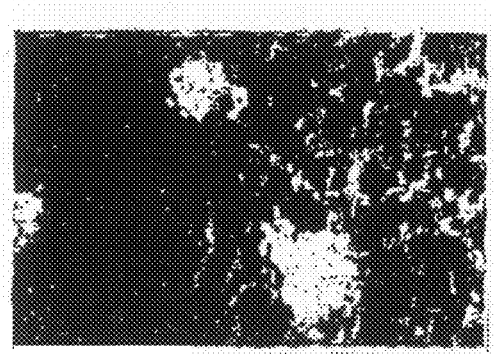

FIGS. 13A-13C show the cytokine (INF-γ, IL-10 and TGF-β) pattern as measured by ELISA in supernatants of Con A-stimulated cultures of splenocytes of mice of the 3 groups taken at the end of treatment (10 weekly s.c. injections). It can be seen that INF-γ (FIG. 13A) and IL-10 (FIG. 13B, to a lesser extent) were down-regulated in the treated mice. An increased secretion of TGF-β could be seen in the supernatants of non-stimulated cells (FIG. 13C, left). Con A did not trigger the cells to secrete more TGF-β (FIG. 13C, right).

The results summarized above indicate that long term treatment with hCDR1 ameliorates disease manifestations and immunomodulates cytokine secretion.

Example 10

Treatment of BALB/c Mice with the Human hCDR1 Peptide Following Induction of Experimental SLE It was of interest to find out whether the hCDR1 peptide is capable of treating experimental SLE induced in mice with the human anti-DNA 16/6Id mAb. Therefore, BALB/c mice were immunized and boosted with the 16/6Id pathogenic autoantibody. Three and a half months following the booster injection, when the mice developed already disease manifestations, they were divided into three groups. One group was not treated, the second group was treated with 100 μg/mouse of the hCDR1 and the third group was treated for 10 weeks with 300 μg/mouse of the hCDR1 peptide. The mice were followed for disease manifestations.

Table 10 presents the results obtained in testing individual mice at the end of treatment. An amelioration was observed for all measured clinical manifestations with both doses used for the treatment [anti-dsDNA antoantibodies, white blood cells counts (WBC) and urine protein]. Analysis of kidneys of mice sacrificed at the end of the experiment (7 months after booster injections) demonstrated immune complex deposits in kidneys of 9/10 mice that were immunized with the 16/6Id mAb and were not treated. In contrast, immune complex deposits were observed in kidneys of only 3/10 and 2/9 mice that were immunized with the 16/6Id mAb and treated with 100 μg/mouse and 300 μg/mouse hCDR1, respectively. Thus, it is shown that the human peptide hCDR1 is capable of treating an established experimental SLE.

TABLE 10

The effect of treatment of BALB/c mice afflicted with experimental SLE with 100 μg or 300 μg hCDR1 peptide.

|  | Control, healthy mice Mean ± SD | 16/6Id injected Mean ± SD | 16/6Id injected + hCDR1 100 μg Mean ± SD | 16/6Id injected + hCDR1 300 μg Mean ± SD |
|---|---|---|---|---|
| Proteinuria g/l | 0.12 ± 0.16 | 0.65 ± 0.36 | 0.3 ± 0.02 | 0.34 ± 0.25 |
| WBC/mm³ | 7440 ± 960 | 3260 ± 920 | 6090 ± 2160* | 5890 ± 2660* |
| Anti-dsDNA O.D. (1:50) | 0.1 ± 0.05 | 1.1 ± 0.6 | 0.3 ± 0.2* | 0.55 ± 0.3* |

*= significantly different (p < 0.05) from 16/6Id injected group.

In another experiment, BALB/c mice were immunized and boosted with the human 16/6Id for induction of experimental SLE. Two months after the boost, mice were divided into groups (8 mice per group). The mice were treated with 200, 300 or 400 μg/mouse for 10 weeks. The mice were followed for antibody production, leukopenia, proteinuria and, when sacrificed, two months after the end of treatment, their kidneys were analyzed for immune complex deposits. The results, summarized in Table 11, show no effect of treatment on the 16/6Id specific antibody response.

TABLE 11

Effect of treatment of BALB/c mice afflicted with experimental SLE with 200 μg, 300 μg or 400 μg hCDR1 peptide.

|  | 16/6Id Mean ± SD | 16/6Id + hCDR1 200 μg/mouse Mean ± SD | 16/6Id + hCDR1 300 μg/mouse Mean ± SD | 16/6Id + hCDR1 400 μg/mouse Mean ± SD | Control Mean ± SD |
|---|---|---|---|---|---|
| Proteinuria g/l | 0.5 ± 0.34 | 0.13 ± 0.16 p = 0.0131 | 0.16 ± 0.16 p = 0.0209 | 0.11 ± 0.15 p = 0.0070 | 0.03 ± 0.09 p = 0.0002 |
| WBC/mm³ | 2871 ± 1205 | 5625 ± 1659 p = 0.0047 | 4677 ± 1508 p = 0.0209 | 4012 ± 1421 p = 0.0760 | 7280 ± 352 p = 0.0001 |
| Intensity of ICD In kidneys | 1.86 ± 0.38 | 0.57 ± 0.97 p = 0.0189 | 0.75 ± 0.71 p = 0.0047 | 0.71 ± 0.76 p = 0.0055 | 0 |
| Anti-dsDNA antibodies at a dilution of: 1:250 | 1.16 ± 0.37 | 0.69 ± 0.39 p = 0.0189 | 0.45 ± 0.24 p = 0.0003 | 0.8 ± 0.39 p = 0.0603 | 0.029 ± 0.025 p = 0.0001 |
| Anti-16/6 Id antibodies at a dilution of 1:1000 | 2.55 ± 0.09 | 2.7 ± 0.12 | 2.8 ± 0.11 | 2.75 ± 0.1 | 0 |

However, treatment affected anti-DNA antibody titers, leukopenia, levels of proteinuria and, more importantly, immune complex deposits in the kidneys. The control group of the experiment is of BALB/c mice of the same age that were not immunized or treated at all. This experiment suggested that hCDR1 is effective in treating experimental SLE and no advantage of the 400 µg dose could be seen.

Figure 15:
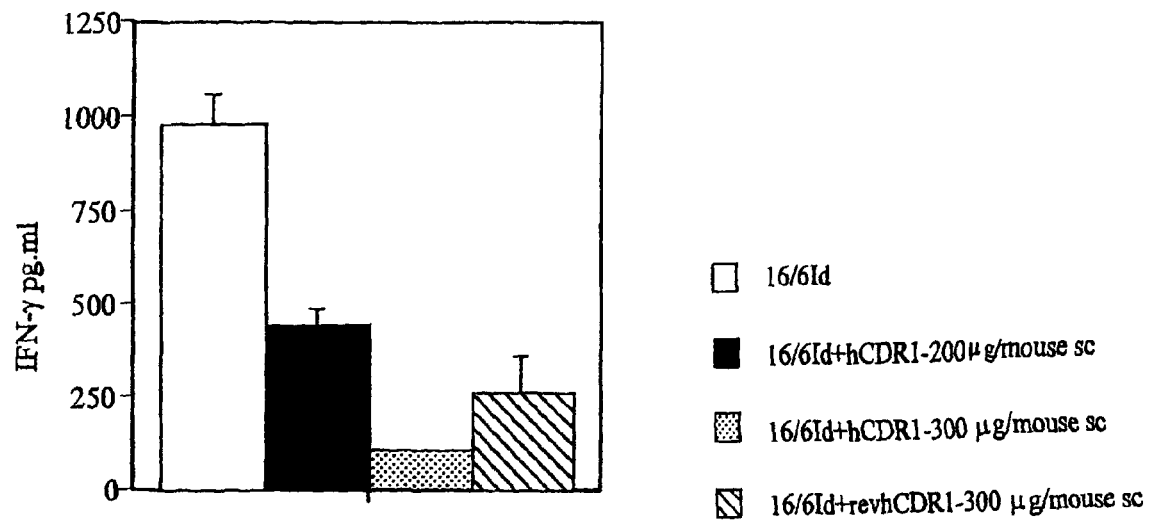
FIGS. 15A-15E show the cytokine pattern as measured by ELISA in supernatants of 16/6Id-stimulated lymph node cultures of BALB/c mice with 16/6Id induced experimental SLE that were untreated or treated with hCDR1 (200 or 300 μg) or with the reversed peptide revhCDR1.
Figure 15:
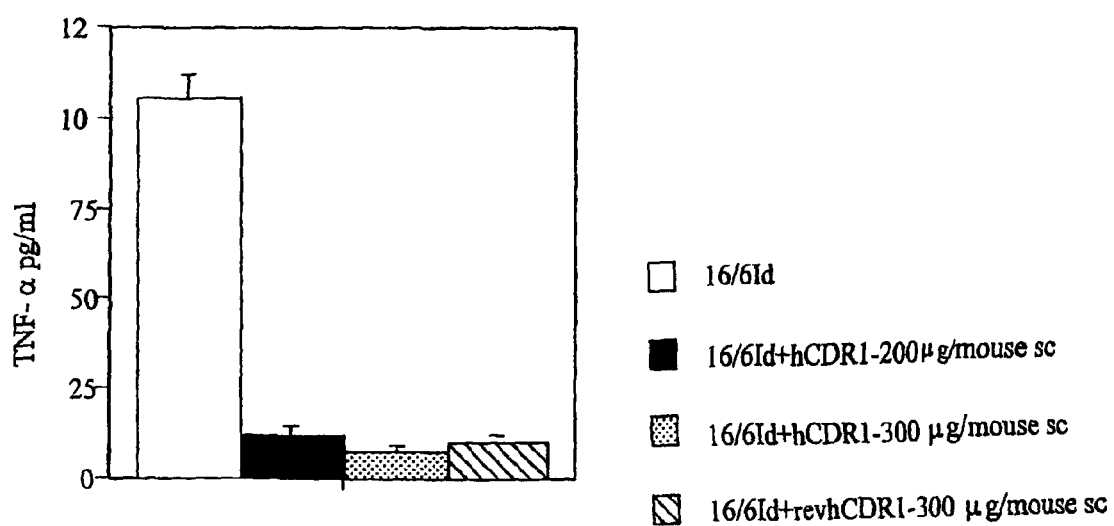
Figure 15:
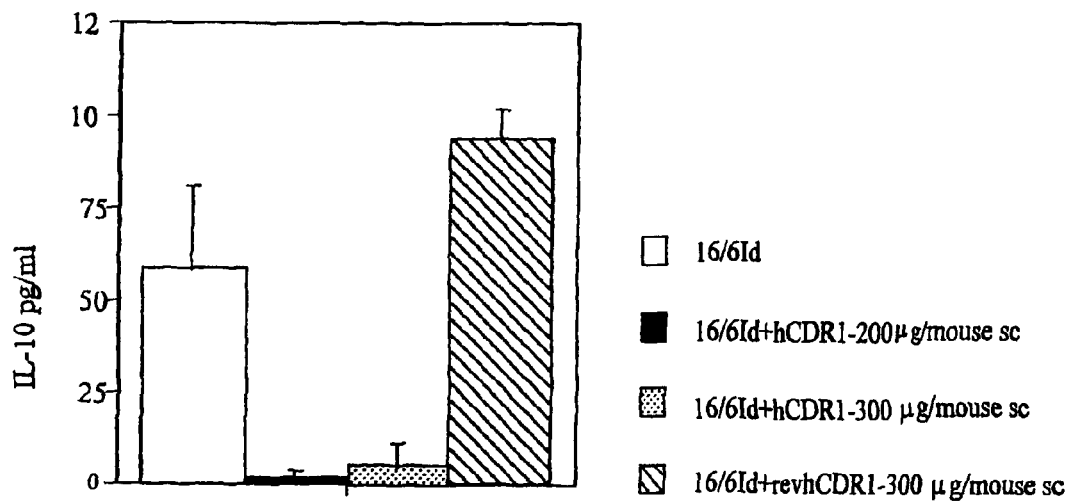
Figure 15:
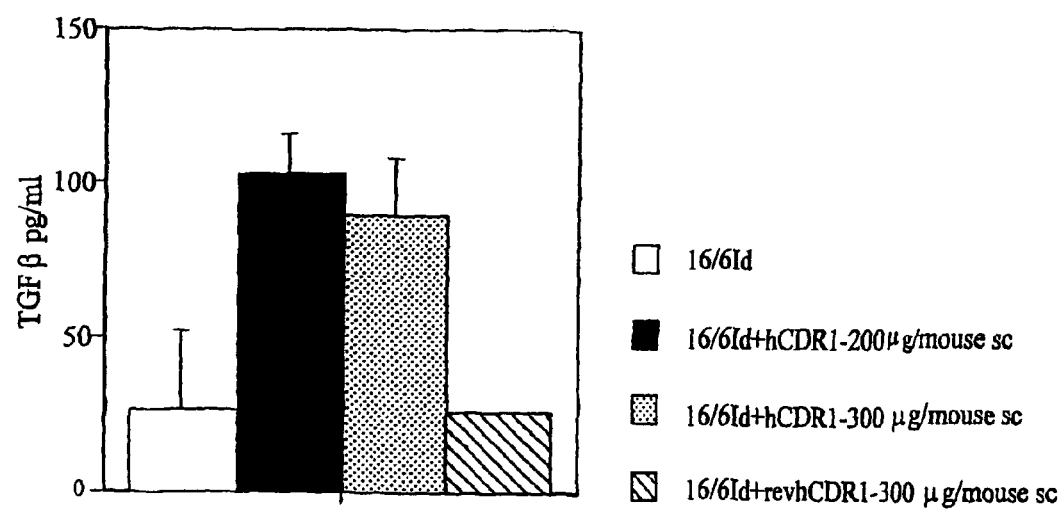
Figure 15:
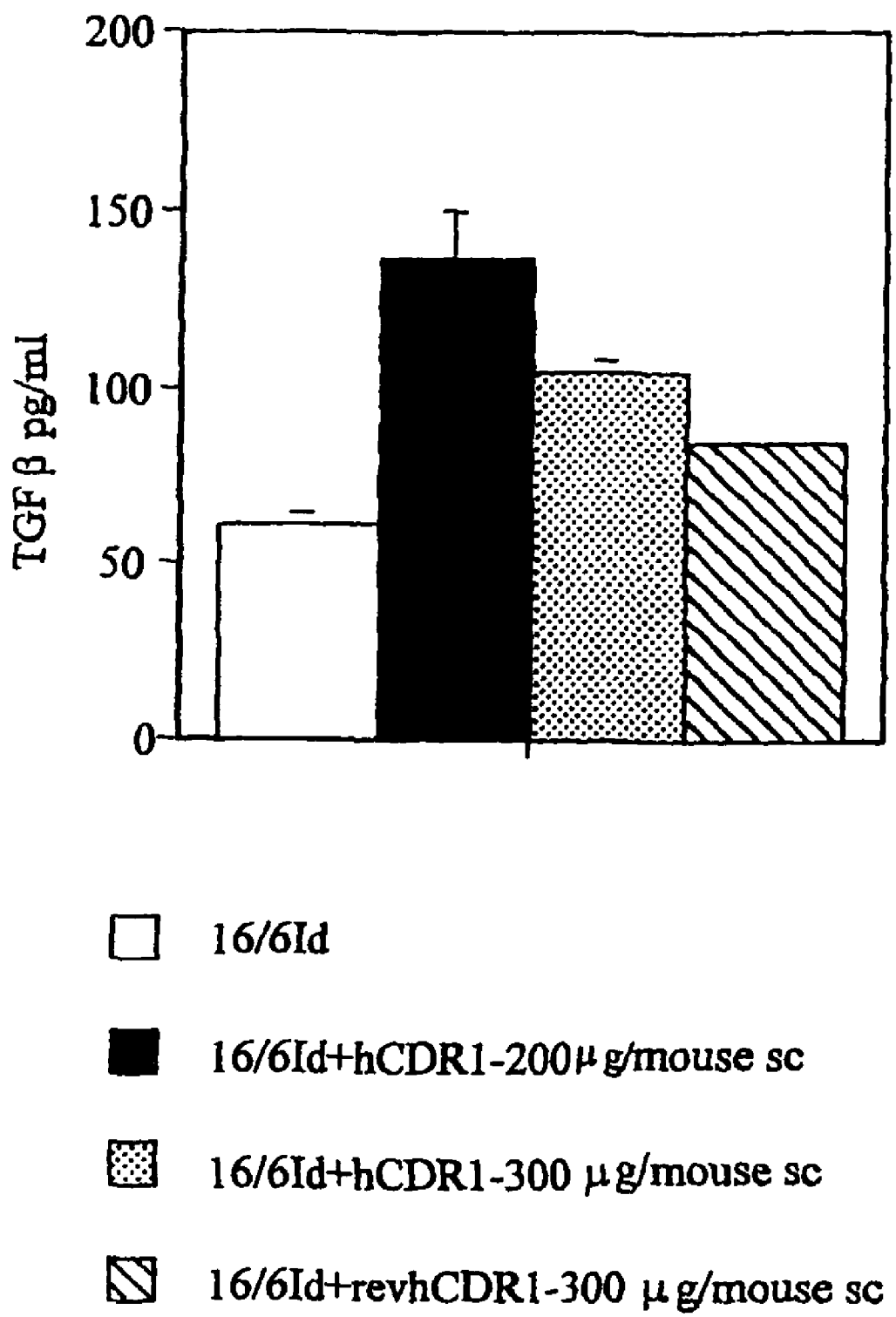
Figure 16A:
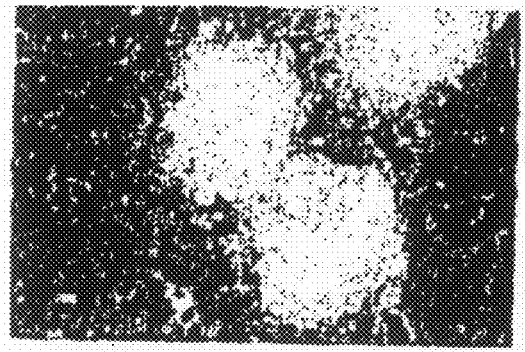
FIGS. 16A-16F are photos showing representative kidney sections of SLE-prone (NZB×NZW)F1 mice untreated (16A, 16B) or mice recipients of splenocytes of mice treated either with 300 μg hCDR1 (16C, 16D) or with the reverse peptide revhCDR1 (16E, 16F). For the detection of immune complex Ig deposits, sections were incubated with FITC-conjugated goat anti-mouse IgG (γ chain specific) (16A, 16C, 16E×400; 16B, 16D, 16F×100).
Figure 16B:
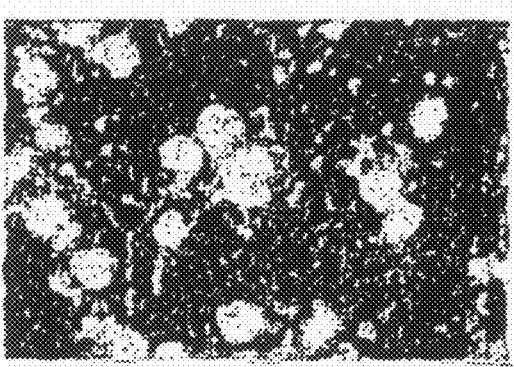
Figure 16C:
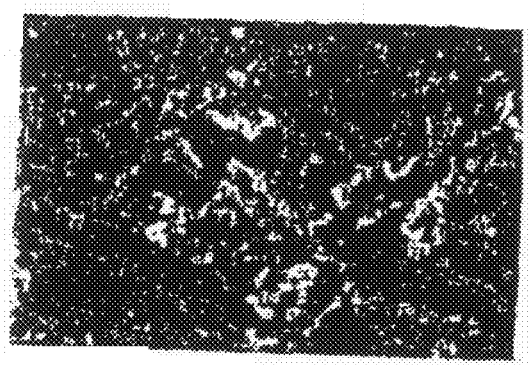
Figure 16D:
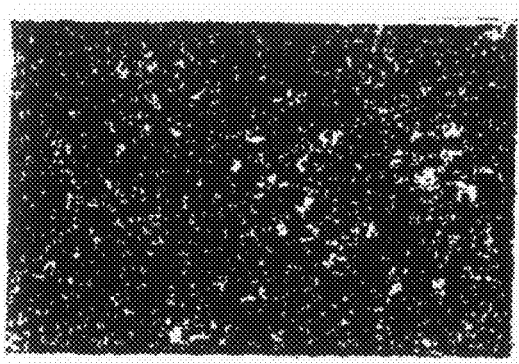
Figure 16E:
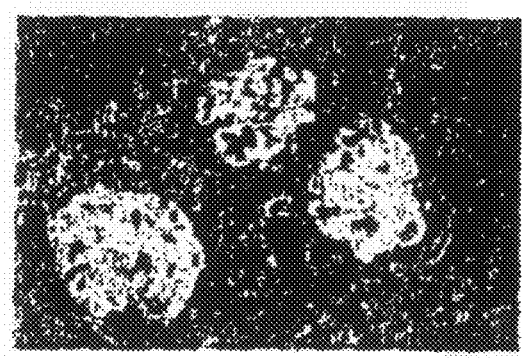
Figure 16F:
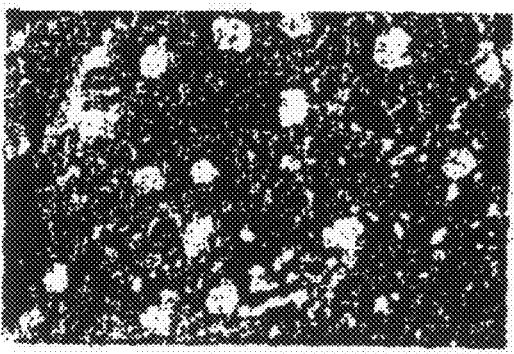

Therefore, an additional experiment was performed in which mice were treated with 200 and 300 µg/mouse. A control peptide was used in this experiment, the reversed hCDR1. The aim of this experiment has been, in addition to the comparison between the 200 and 300 µg treatment doses, to study the effect of treatment on the cytokine production in the treated mice. Sixty BALB/c mice were immunized and boosted with the 16/6Id. Three months after the boost, the mice were divided into groups (15 mice per group) that either were not further treated or were weekly treated with 200 or 300 µg of hCDR1. An additional group was treated with 300 µg of reversed hCDR1. A fifth group (control) was not immunized and was not further treated. Mice were followed for antibody production and disease manifestations. As seen in Table 12, the anti-16/6Id antibody levels (at a dilution of 1:10000) in sera of the mice did not differ between groups. Treatment with both 200 and 300 µg reduced the anti-DNA antibody levels as can be seen in the Table (the sera were diluted 1:1250). Table 12 also summarizes the clinical manifestations in the different groups of mice. It can be seen that, although both doses were effective in reducing leukopenia and proteinuria, the effect of the 200 µg dose in this experiment did not reach significance (mice were sacrificed a month after the end of treatment).

treated mice. The latter tests were performed at the end of treatment (after 10 treatment injections). It can be seen that treatment with hCDR1 (both doses) down regulated INF-γ (FIG. 15A), IL-10 (FIG. 15C) and TNF-α (FIG. 15B). On the other hand, hCDR1 up-regulated the levels of TGF-β. Because splenocytes usually secrete more TGF-β (FIG. 15D) than lymph node cells, TGF-β was also measured in supernatants of 16/6Id triggered spleen cells of mice of the different groups (FIG. 15E).

Thus, hCDR1 ameliorates disease manifestations and immunomodulates cytokine production in mice afflicted with an induced experimental SLE.

Example 11

Transfer of the Beneficial Effects on Lupus Manifestations by Splenocytes of hCDR1-Treated Mice It was of importance to investigate whether the beneficial effects of treatment with hCDR1, that are manifested by the down-regulation of disease manifestations, can be transferred by spleen cells of treated mice. To this end, we have performed an experiment in which 8-month old (NZB×NZW)F1 mice, that suffer already from the full-blown lupus-like disease, were divided into 2 groups. Group 1 was not treated and mice of group 2 were transferred with $20 \times 10^6$ spleen cells of 3-month old (NZB×NZW)F1 mice that were injected 3 times (s.c., every other day) with 300 µg/mouse of hCDR1. All splenocytes were injected intraperitoneally. Mice were tested for anti-dsDNA autoantibody production, disease manifestations, and were sacrificed 4 weeks after cell transfer. Transfer

TABLE 12

Effect of treatment of BALB/c mice afflicted with experimental SLE with 200 µg or 300 µg hCDR1 or 300 µg revhCDR1

|  | 16/6Id<br>Mean ± SD | 16/6Id +<br>hCDR1<br>200<br>µg/mouse<br>Mean ± SD | 16/6Id +<br>hCDR1<br>300<br>µg/mouse<br>Mean ± SD | 16/6Id +<br>rev-hCDR1<br>300<br>µg/mouse<br>Mean ± SD | Control<br>Mean ± SD |
|---|---|---|---|---|---|
| Proteinuria g/l | 0.58 ± 0.34 | 0.17 ± 0.15<br>p = 0.0366 | 0.085 ± 0.01<br>p = 0.0088 | 0.8 ± 0.3<br>p > 0.5 | 0.031 ± 0.09 |
| WBC/mm$^3$ | 2800 ± 300 | 4900 ± 800<br>p = 0.004 | 5800 ± 300<br>p = 0.004 | 4180 ± 831<br>p = 0.0079 | 7900 ± 400 |
| Intensity of ICD in kidneys | 1.6 ± 0.55 | 1 ± 0.63<br>p = 0.0887 | 0.5 ± 0.5<br>p = 0.0152 | 0.85 ± 0.75<br>p = 0.0628 | 0 |
| Anti-dsDNA antibodies 1:1250 | 0.47 ± 0.3 | 0.23 ± 0.1<br>p = 0.0234 | 0.2 ± 0.1<br>p = 0.0145 | 0.35 ± 0.3<br>p = 0.343 | 0.002 ± 0.002 |
| Anti-16/6 Id antibodies 1:10000 | 0.89 ± 0.1 | 0.96 ± 0.2 | 0.93 ± 0.1 | 0.95 ± 0.13 | 0.03 ± 0.1 |

FIGS. 14A-F represent one kidney of each group where A,B represent an untreated mouse; C,D represent a kidney of a hCDR1-treated mouse and E,F represent a kidney section of a mouse treated with the reversed hCDR1. Pictures A,C,E× 100 and B,D,F×400.

FIGS. 15A-E shows levels of the different cytokines in supernatants of 16/6Id stimulated lymph node cultures of the of cells of hCDR1-treated mice caused a mild reduction in the levels of anti-DNA antibodies.

Table 13 demonstrates that transfer of splenocytes of hCDR1-treated mice resulted in a significantly lower proteinuria and in a reduction in immune complexes in the kidneys.

TABLE 13

Clinical lupus manifestation in mice recipient of spleen cells of mice treated with hCDR1

| Group No. | Treatment | Proteinuria g/L ± SEM | I.C.D ± SEM |
|---|---|---|---|
| 1 | Non-treated | 15.07 ± 4.92 | 2.25 ± 0.47 |
| 2 | 20 × 10$^6$ spleen cells from hCDR1 treated mice | 0.97 ± 0.67 p = 0.05 | 0.75 ± 0.47 p = 0.05 |

The p-values are calculated in comparison to gr1 of untreated mice

The experiment was repeated a few more times using revh-CDR1 as control. The results were similar to those in the first experiment, namely, cell transfer of the treated mice affected slightly anti-DNA antibody titers and significantly proteinuria and kidney damage. The clinical manifestations of a representative experiment are shown in Table 14.

TABLE 14

Clinical lupus manifestation in mice recipient of spleen cells of mice treated with hCDR1

| Group No. | Treatment | Proteinuria g/L ± SEM | I.C.D ± SEM |
|---|---|---|---|
| 1 | Non-treated | 10.9 ± 3.05 | 2.3 ± 0.26 |
| 2 | 20 × 10$^6$ spleen cells from hCDR1 treated mice | 2.91 ± 1.6 p = 0.0402 | 1.33 ± 0.35 p = 0.034 |
| 3 | 20 × 10$^6$ spleen cells from revhCDR1 treated mice | 5.38 ± 2.34 p = 0.0931 | 1.7 ± 0.23 p = 0.065 |

The p-values are calculated in comparison to gr1 of untreated mice

It can be seen that the down-regulating effect of treatment with hCDR1, could be transferred by spleen cells of the treated mice.

FIGS. 16A-F represent kidney sections of mice of group 1 (A, B—untreated mice), group 2 (C, D—recipients of splenocytes of 2-month old mice treated with hCDR1) and group 3 (E, F—recipients of splenocytes of 2-month old mice treated with revhCDR1). A,C,E×400; B,D,F×100.

The results of the above experiments indicate that the ameliorating effects on disease manifestations of hCDR1 can be transferred by immunocytes of healthy mice that were treated with hCDR1.

Example 12

Down-Regulation of MMP-3 and MMP-9 by the Murine mCDR Peptides

Matrix metalloproteinases (MMPs) (Shingleton et al., 1996; Goetzl et al., 1996; Massova et al., 1998) constitute a family of zinc containing endoproteinases that play an important role in the remodeling of extracellular matrix in normal tissues, and also contribute to pathological processes. They share structural domains but differ in substrate specificity, cellular sources and inducibility.

The MMPs are synthesized as zymogen-like latent precursors and are converted subsequently to an active form. MMP-2 and MMP-9, which are both gelatinases, can degrade type IV collagen, denatured collagens, types V, VII, X and XII collagens, vitronectin, aggrecan, galectin-3 and elastin. MMP-2 is the most widely expressed MMP. It is produced by a variety of cells and is frequently elevated in malignant tumor metastasis.

In terms of protein and domain structure, MMP-9 is the largest and most complex member identified so far. MMP-9 expression is characterized by a complex regulation with tight control at the levels of gene transcription and protein secretion (such as cytokines, chemokines, eicosanoids) inflammatory mediators, and action of tissue inhibitors of metalloproteinases (TIMPs). In addition, MMP-9 activity is modulated by the activation of pro-MMP-9, by components of the plasminogen activation system or other MMPs (Guedez et al., 1996).

The involvement of MMPs in autoimmune diseases was demonstrated in various autoimmune diseases such as multiple sclerosis (Ozenci et al., 1999) and its animal model experimental autoimmune encephalomyelitis (EAE) (Gijbels et al., 1994), rheumatoid arthritis (Keyszer et al., 1999), Guillain-Barré syndrome (Creange et al., 1999), experimental bullous pemphigoid (Liu et al., 1998) and experimental autoimmune neuritis (Hughes et al., 1998). Serum levels of MMP-3 and TIMP-2 in patients with lupus nephritis were reported to be significantly higher than those of healthy controls, but no correlation with disease activity was noted (Zucker, 1999; Keyszer et al., 1999).

The potential importance of the many activities of MMPs in inflammatory responses has been suggested by the inhibitory effects of MMP inhibitors in several animal models of autoimmune diseases. Specific inhibition of MMPs in vivo suppresses edema, pathologic tissue proliferation, and damage to specialized tissue structures in several inflammatory and autoimmune diseases (Gijbels et al., 1994; Wallace et al., 1999; Conway et al., 1995).

According to the present invention, we show that levels of MMP-3 and MMP-9 are elevated both in sera and in kidneys of mice afflicted with either the spontaneous or the induced experimental SLE. We also demonstrate that treatment of SLE-afflicted mice with the CDR-based murine peptides, that ameliorate manifestations of lupus in mice, diminished the levels of MMP-3 and MMP-9 in the serum and kidneys of the treated mice and also caused amelioration of disease manifestations. The same effects are expected to be presented by the human hCDR peptides of the invention.

Example 12(i)

Figure 17A:
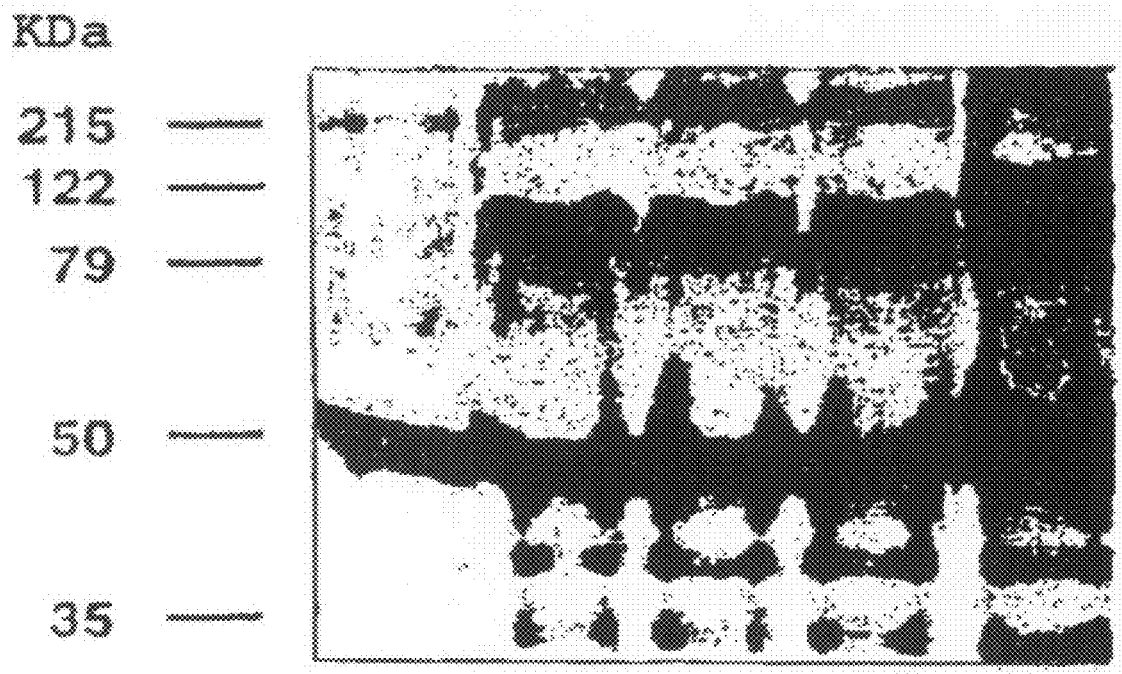
FIGS. 17A-17B depict kinetics of appearance of MMP-3, MMP-2, and MMP-9 in the sera of (NZB×NZW)F1 mice. (NZB×NZW)F1 mice (10 mice/group) were bled at the indicated time points. Pooled sera (4 μl) of mice from each group were tested for MMP-3 expression levels using Western blot (FIG. 17A) or for MMP-9 and MMP-2 activities using gel zymography (FIG. 17B). The results represent 4 similar experiments.
Figure 17B:
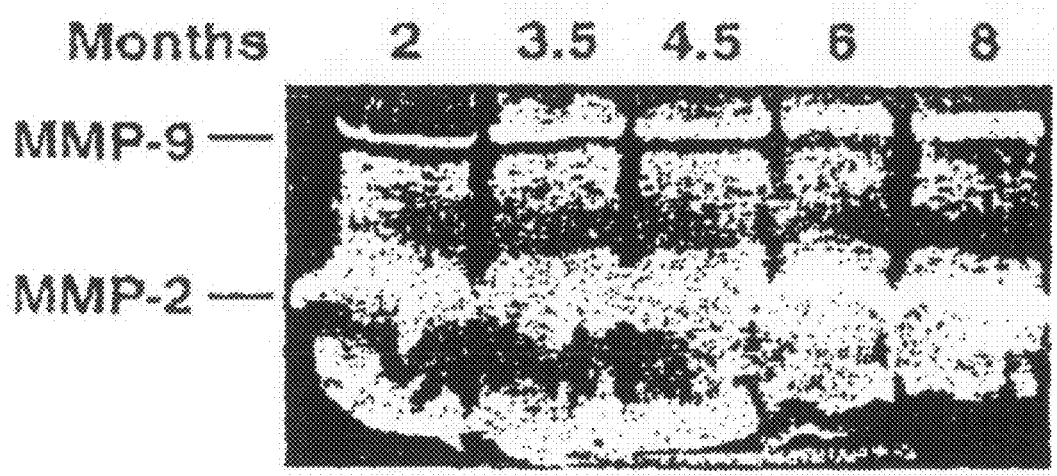

Kinetics of Appearance of MMP-3, MMP-2 and MMP-9 in sera of (NZB×NZW)F1 Mice We first examined if the development of spontaneous SLE in (NZB×NZW)F1 mice is associated with changes in the levels of MMP-3, MMP-2 and MMP-9 in their sera. We thus followed the levels of the latter starting at the age of 2 months, before disease manifestations are observed, until the age of 8 months when the mice suffer from a full blown disease. The results are shown in FIG. 17. As can be seen in FIG. 17A, both the 34 kd and the 40 kd forms of MMP-3 in sera of 2-month old mice are very low as detected by Western blot analysis. The levels of all forms are gradually elevated towards the age of 8 months, the last time point tested. Similarly, FIG. 17B shows that MMP-9 activity, assessed by gel zymography, is low at the age of 2 months and is gradually elevated in sera of mice with the progression of disease, until the age of 8 months. It is also seen in FIG. 17B that levels of MMP-2 are not changed significantly with the progression of disease.

Example 12(ii)

Figure 18A:
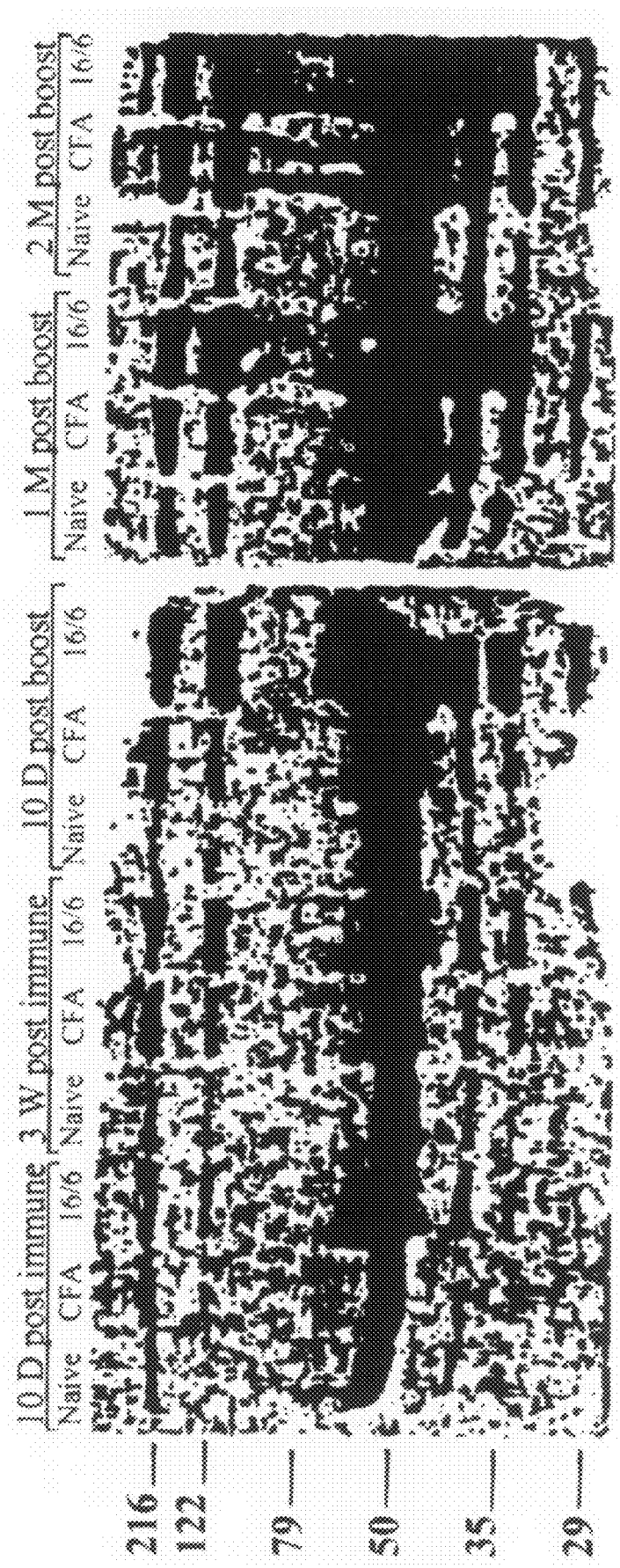
FIGS. 18A-18B depict kinetics of appearance of MMP-3, MMP-2, and MMP-9 in the sera of BALB/c mice. Non-immunized BALB/c mice (10 mice/group) or mice that were immunized with PBS/CFA (10 mice/group) or with the 16/6Id (in CFA; 10 mice/group), were bled at the indicated time points. Pooled sera of mice (4 μl) from each group were tested for MMP-3 expression levels using Western blot (FIG. 18A) or for MMP-9 and MMP-2 activities using gel zymography (FIG. 18B). The results are representative of 3 similar experiments.
Figure 18B:
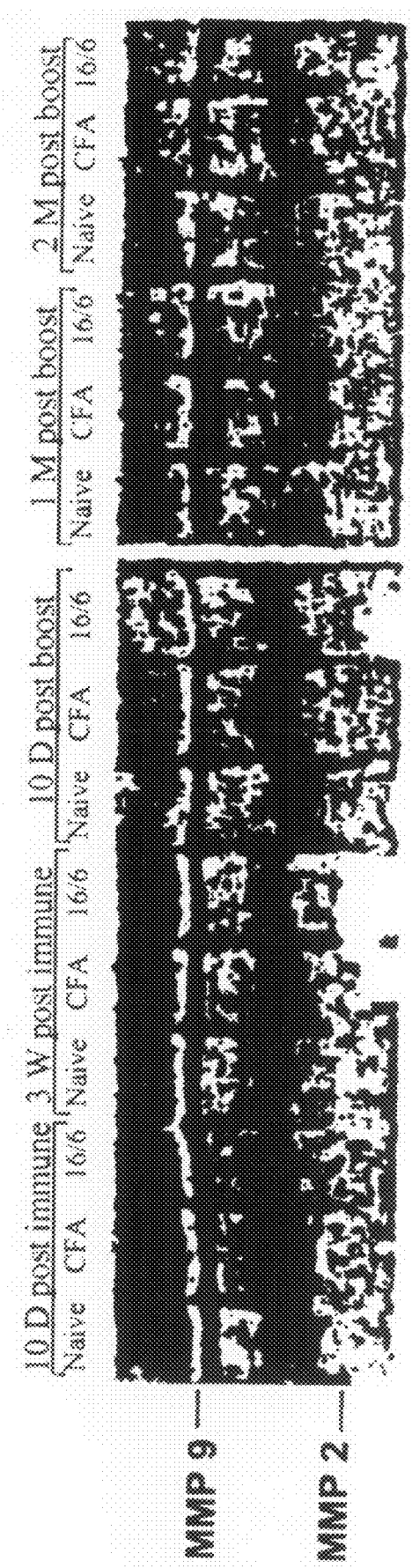

Kinetics of Appearance of MMP-3, MMP-2 and MMP-9 in Sera of BALB/c Mice that were Immunized with 16/6Id Previous results from our laboratory have shown that SLE can be induced in BALB/c mice following immunization with the 16/6Id (Mendlovic et al., 1988; Waisman et al., 1993). Therefore, it was of interest to test if the induced model of SLE resembles the (NZBxNZW)F1 model with respect to the changes in MMP-3 and MMP-9. We thus looked at levels of MMP-3 and MMP-9 in this experimental model of SLE. The results demonstrated in FIG. 18 indicate that the levels of MMP-3 (all isoforms) were elevated 10 days after the boost (4.5 weeks post-immunization), and were higher than in control unimmunized or CFA-immunized BALB/c mice of the same age (FIG. 18A). The levels of MMP-3 increased with aging in all groups, however, the latter were always higher in the 16/6Id immunized mice than in the control groups. In contrast, no induced changes in MMP-9 activity could be detected until 2 months after the boost (FIG. 18B). Higher activity of MMP-9 in the 16/6Id immunized mice than in non immunized mice, could be observed at about 4 months after the boost.

Example 12(iii)

Figure 19A:
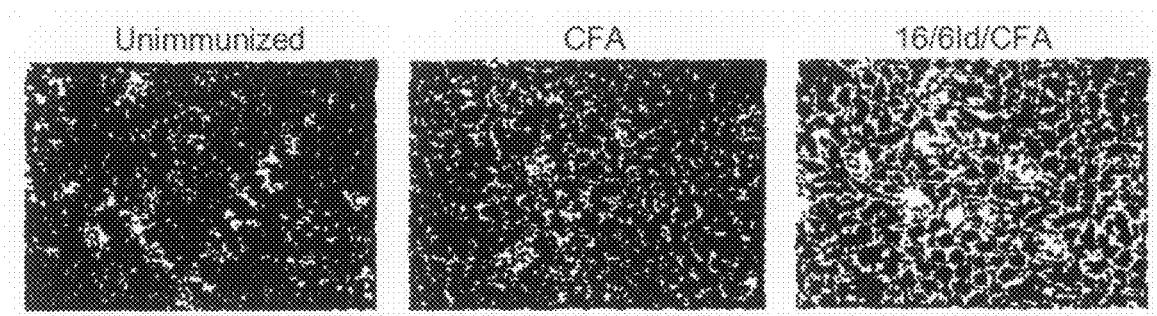
FIGS. 19A-19C depict immunostaining of kidney sections of immunized BALB/c mice for MMP-3 and MMP-9. Non-immunized BALB/c mice or mice that were immunized with PBS/CFA or with the 16/6Id (in CFA), (3 mice/group), were sacrificed 5.5 months following their boost with the 16/6Id. Kidneys were removed, and their 5 μm cryostat sections were immunostained for MMP-3 (19A) and MMP-9 (19B). A control staining to the efficiency of blocking, was performed (19C). (×200). The results are representative of 3 similar experiments.
Figure 19B:
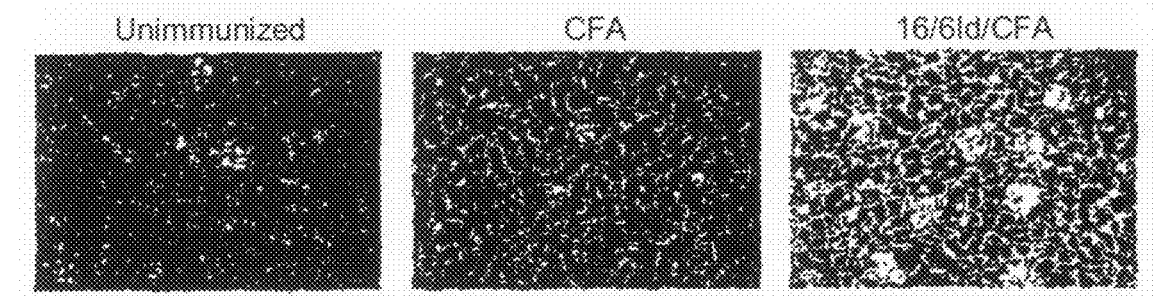
Figure 19C:
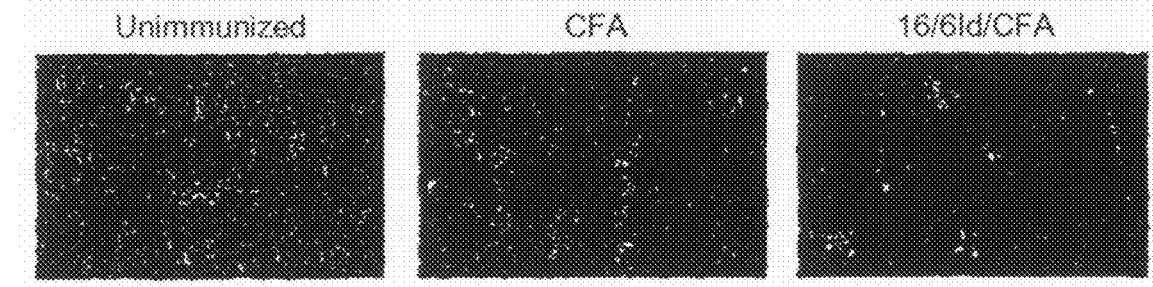

Specific up Regulation of MMP-3 and MMP-9 in Kidney Sections of BALB/c Mice that were Immunized with the 16/6Id Since immunization of BALB/c mice with the 16/6Id leads to clinical manifestations characteristic of SLE including kidney damage (Mendlovic et al., 1988; Waisman et al., 1993), and because kidney damage in (NZBxNZW)F1 mice was reported to be associated with elevation in the levels of MMP-3 and MMP-9 (Nakamura et al., 1993), we looked at the expression of these enzymes in kidneys of BALB/c mice that were immunized with 16/6Id. As controls, we used mice that were immunized with CFA and aged matched unimmunized mice. Both control groups were injected with PBS at the time point of the boost. Two months and 5 months after the boost with 16/6Id, kidney sections of mice were immunostained for MMP-3 or MMP-9. FIG. 19 represents immunohistology of kidneys taken 5 months after the boost. As can be seen in the figure, immunization of mice with CFA up-regulated the expression of both MMP-3 (19A) and MMP-9 (19B) in the kidneys, in the glomeruli and in the surrounding tissue. Nevertheless, immunization with 16/6Id in CFA further elevated significantly the expression levels of these two MMPs. This elevation was observed already two months after the boost with the 16/6Id (data not shown). The nonspecific background levels of the staining are also demonstrated (19C).

Example 12(iv)

Figure 20A:
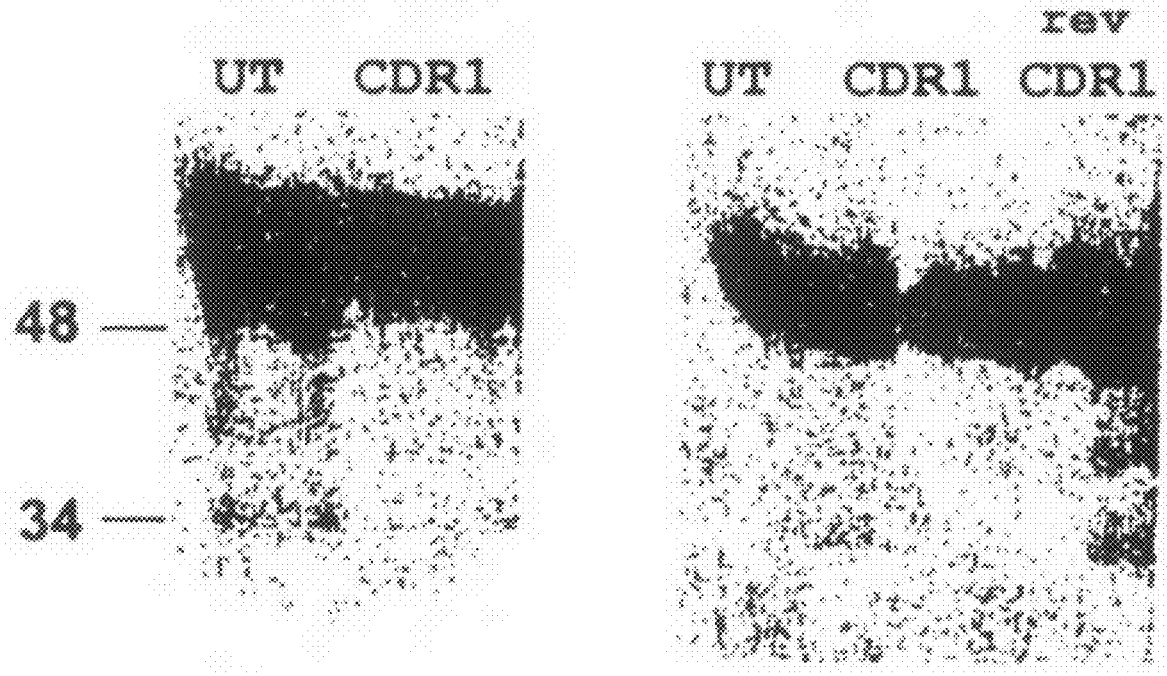
FIGS. 20A-20B depict levels of MMP-3 and MMP-9 in sera of (NZB×NZW)F1 mice treated with mCDR1. In prevention experiments, mice (10/group) were given weekly s.c. injections with mCDR1 starting at the age of 2 months during 10 weeks. The results represent sera taken 4 months after the end of the treatment. In treatment experiments, mice (10/group) were injected s.c. with either PBS or 250 μg/mouse of mCDR1 starting at the age of 5 months. The results represent sera taken 3 weeks after the end of the treatment. Pooled sera of each experimental group were tested for MMP-3 levels by Western blot analysis (20A) and for MMP-9 activity using gel zymography (20B). UT—untreated. The results are representative of 2 similar experiments.
Figure 20B:
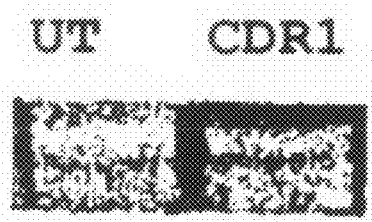
Figure 20B:
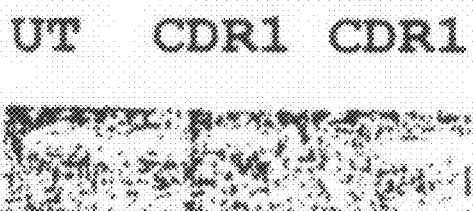

The Murine mCDR1 Peptide Down Regulates Levels of MMP-3 and Activity of MMP-9 in Sera of (NZBxNZW)F1 Mice Since we could show that levels of MMP-3 and MMP-9 are elevated in both experimental models of SLE, it was of interest to examine if the amelioration in the clinical symptoms of SLE observed following treatment with the mCDR1 peptide (Eilat et al., 2000; Eilat et al., 2001), is accompanied by a reduction in levels of MMP-3 and MMP-9. We thus treated (NZBxNZW)F1 mice that develop SLE-like disease spontaneously, at the age of 2 months (before clinical manifestations are observed) by injecting them weekly with mCDR1 in PBS (250 µg/mouse) s.c. for 10 weeks. This prevention protocol resulted in the amelioration of all clinical symptoms (Eilat et al., 2000). As can be seen in FIG. 20, there is a reduction in the two lower bands of MMP-3 (20A) and in MMP-9 activity (20B) in the serum. This reduction is associated with the reduction in the clinical manifestations (Eilat et al., 2000). As seen in FIG. 20A, the 45 kd form of MMP-3 was not affected.

It was also of interest to find out whether the mCDR1 peptide is capable of down regulating elevated levels of MMP-3 and activity of MMP-9. We thus looked at the levels of MMP-3 and at MMP-9 activity in the sera of (NZBxNZW)F1 mice that were treated with mCDR1 at the time that disease manifestations were already observed. As a control peptide we used the reversed mCDR1. As can be seen (FIG. 20, at the right), treatment of sick mice with mCDR1, but not with revmCDR1, specifically down-regulated the levels of MMP-3 (20A) and the activity of MMP-9 (20B) in the sera.

Example 12(v)

Figure 21A:
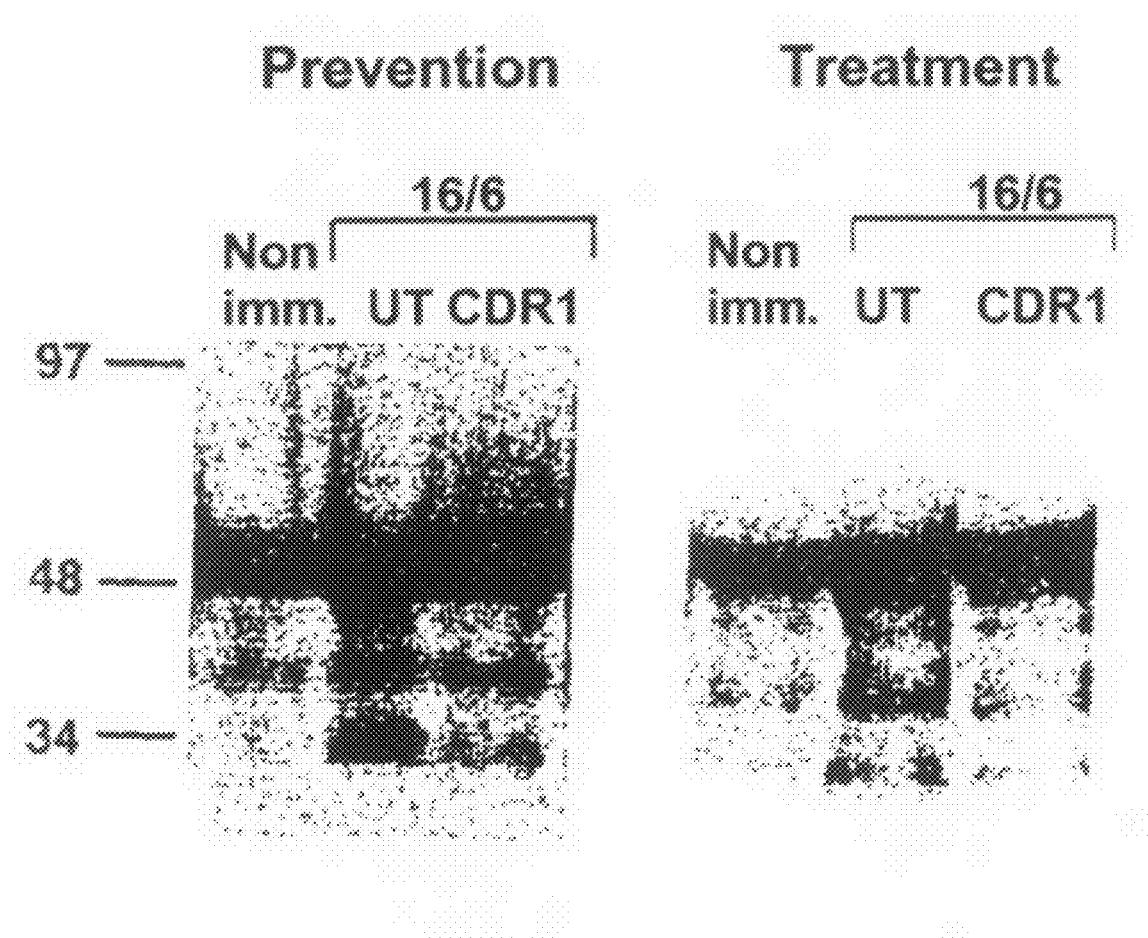
Figure 21B:
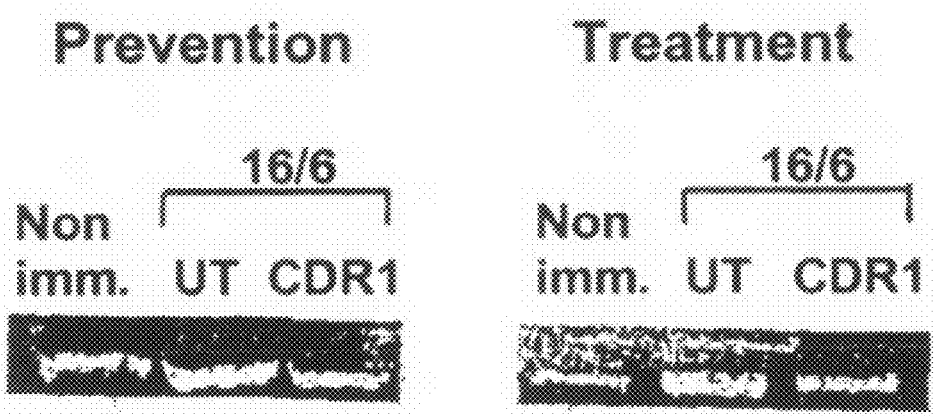

The mCDR1 Peptide Down-Regulates Levels of MMP-3 and Activity of MMP-9 in Sera of 16/6Id Immunized Mice As we have demonstrated, activity of MMP-9 is elevated in both experimental models [(NZBxNZW)F1 and 16/6Id-induced] of SLE. Because the mCDR1 peptide was shown to ameliorate the disease in both models, and to down-regulate MMP-3 levels and MMP-9 activity in sera of treated (NZBxNZW)F1 mice, we further looked for the effect of treatment on these enzymes in sera of 16/6Id immunized BALB/c mice. FIG. 21 represents results of a prevention and a treatment experiments. The figure shows that mCDR1 could down regulate MMP-3 and MMP-9 in this experimental model as well. Down regulation of levels of MMP-3 and of MMP-9 activity was observed for both the prevention and the treatment protocols. Thus, in vivo administration of mCDR1, either at the stage of disease induction or at the stage of a full blown disease, could reduce the levels of MMP-3 (21A) and MMP-9 (21B). This reduction was specific, since treatment with the reversed mCDR1 did not affect MMP-3 or MMP-9 activity (not shown). Preliminary results, using the MMP-9 activity assay system (from Amersham-Pharmacia Biotech UK Limited, England) show that the activity of sera from unimmunized BALB/c mice is comparable to 7 ng/ml of pure active MMP-9. Immunization with the 16/6Id elevates the activity to 16 ng/ml and treatment with the mCDR1 peptide down regulates it almost to the normal levels (8.5 ng/ml).

Example 12(vi)

Figure 22A:
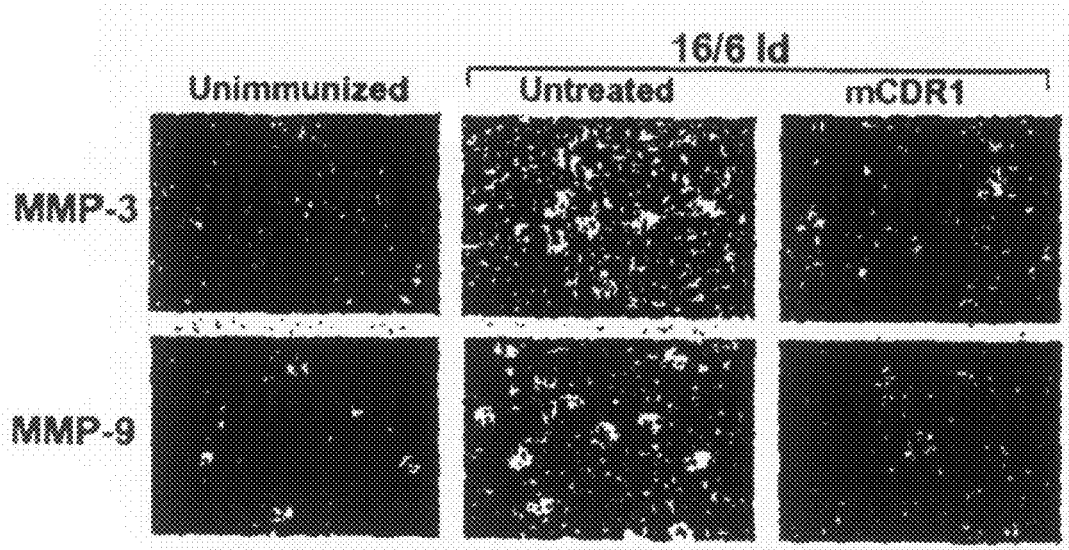
Figure 22B:
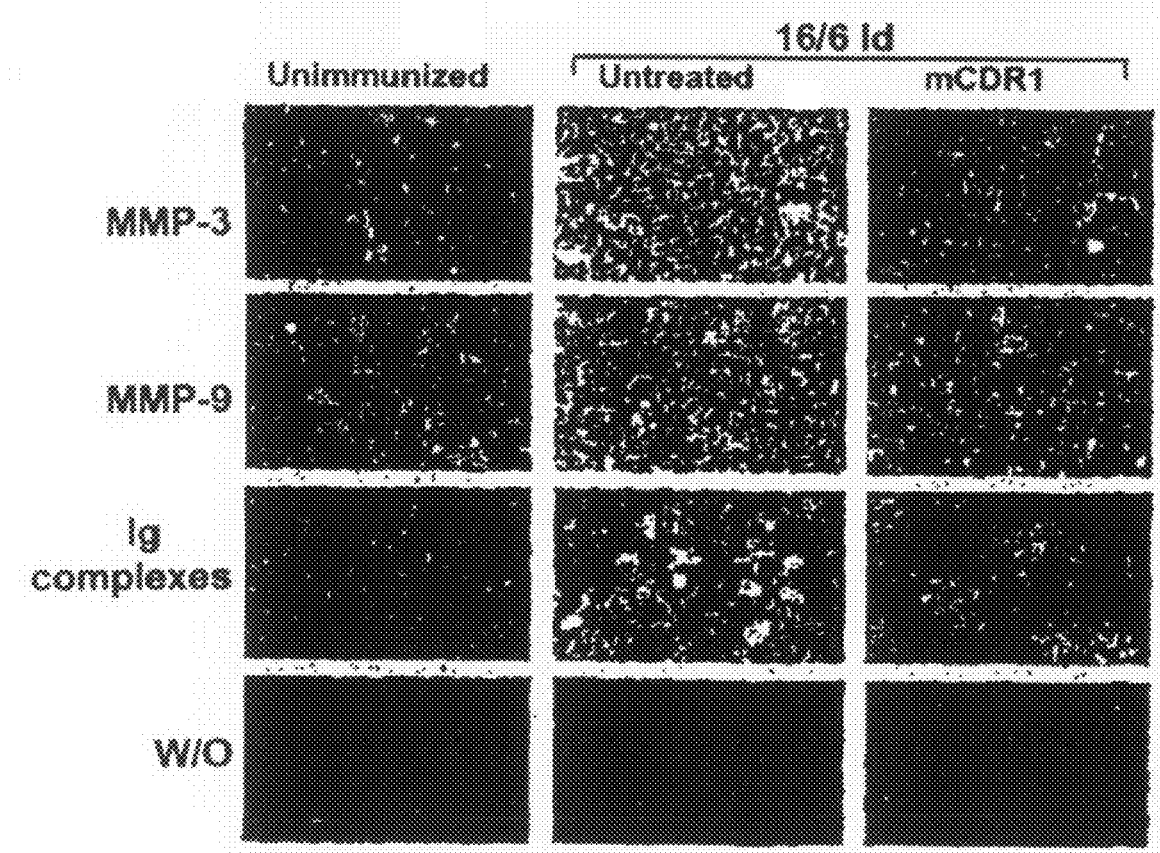

Effect of Treatment with the mCDR1 Peptide on the Levels of MMP-3 and MMP-9 in Kidney Sections of 16/6Id Immunized BALB/c Mice Because MMP-3 and MMP-9 were shown to be elevated in kidneys of mice with induced experimental SLE, it was of interest to look for the effect of treatment with the mCDR1 peptide on the expression of the latter MMPs in the kidneys of the treated mice. FIG. 22 demonstrates that in both prevention (FIG. 22A) and treatment (FIG. 22B) experiments, mCDR1 down-regulated the expression levels of both MMP-3 and MMP-9 in the kidneys of the treated mice. The reduction in the levels of MMP was observed in both the glomeruli and interstitium. The observed reduction in MMP expression correlated with the reduction in staining for immune complex deposits using anti-Ig (FIG. 22B).

Figure 23A:
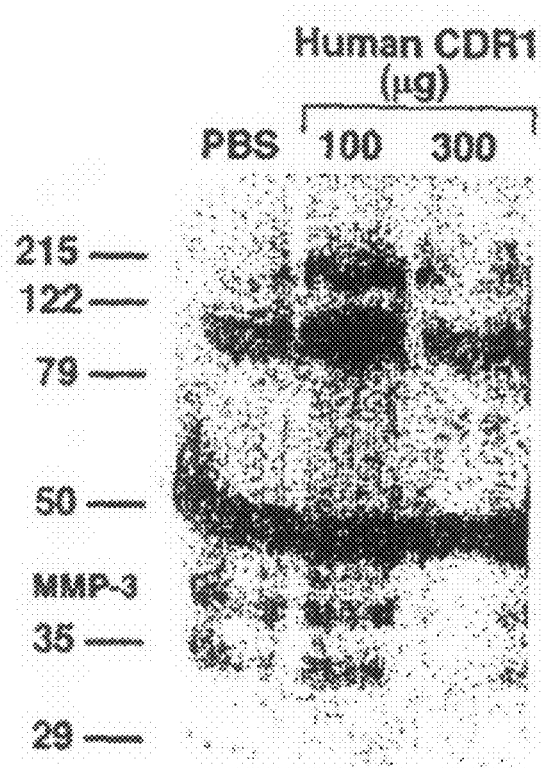
FIGS. 23A-23B depict levels of MMP-3 and MMP-9 in sera of (NZB×NZW)F1 mice treated with hCDR1. In treatment experiments, mice (10/group) were injected s.c. with either PBS or 100 μg or 30 μg/mouse of hCDR1 once a week for ten weeks starting at the age of 7 months. The results represent sera collected at the middle of the treatment. Pooled sera of each experimental group were tested for MMP-3 levels by Western blot analysis (23A) and for MMP-9 activity using gel zymography (23B). The results are representative of 2 similar experiments.
Figure 23B:
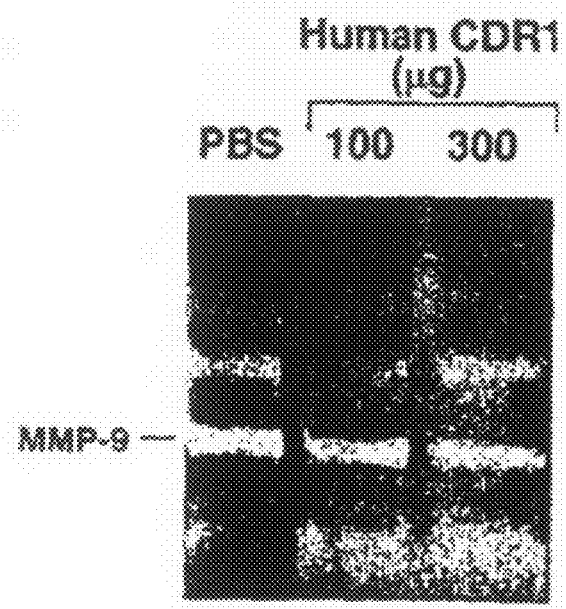

Because of the apparent involvement of MMP-3 and MMP-9 in the pathogenesis of SLE, we tested whether the human hCDR1 peptide is capable of down-regulating the levels of the latter in correlation with the amelioration of disease manifestations. To this end, pooled sera of groups of (NZB×NZW)F1 mice that were treated with the hCDR1 by s.c. injections of 100 μg or 300 μg/mouse once a week for ten weeks were tested for MMPs levels at various periods during the treatment. FIG. 23 represents results of an experiment in which mice were treated starting at the age of 7 months when all clinical manifestations were observed. The results are of sera collected at the middle of treatment, after 5 injections of hCDR1. The results of FIG. 23 indicate that treatment of mice with 300 μg hCDR1 down regulated the levels of MMP-3 and the activity of MMP-9. These results are in agreement with the significant amelioration of disease manifestations following treatment with hCDR1.

Discussion

The above results show that both MMP-3 and MMP-9 are elevated in sera and in kidneys of murine models of SLE. The murine mCDR1 peptide could down regulate the levels of MMP-9 and MMP-3 in both sera and kidneys of SLE-afflicted mice. It is demonstrated that in the spontaneous model of SLE, up regulation of both MMP-9 and MMP-3 in the serum occurs at the first 3.5 months. In the induced model the elevation in the levels of MMP-3 in sera is very early (10 days after the boost with the 16/6Id), while the elevation of MMP-9 activity occurs about 3-4 months later. Based on the results with the 16/6Id induced model that allows us to follow processes at the first stages of the disease, it seems that MMP-3 is involved in disease induction while MMP-9 is involved in disease progression.

Our results showing the elevation of MMP-3 in the mouse models of SLE, are in agreement with results demonstrating that MMP-3 is significantly increased in sera of patients with SLE (Kotajima et al., 1998) and that MMP-3 transcript is significantly increased with the progression of nephritis in (NZB×NZW)F1 mice (Nakamura et al., 1993). Taken together, these results suggest that MMP-3 may contribute to the development of glomerular injury in lupus nephritis.

Our results show that activity levels of MMP-2 in sera are not elevated significantly with disease progression in both the induced and the spontaneous models of SLE. These results are compatible with those reported previously (Zucker, 1999) that MMP-2 levels were not increased in SLE. Accordingly, this enzyme was not modulated by treatment with the CDR1-based peptide (data not shown). Levels of MMP-2 were secreted constitutively and did not change in other pathological conditions (like optic neuritis and multiple sclerosis) as well, whereas levels of MMP-9 were elevated relatively to the healthy controls (Gijbels et al., 1992; Paemen et al., 1994).

Interestingly, the mCDR1 peptide, that specifically and directly affects SLE-associated T-cell responses, could down regulate levels of MMP-3 and MMP-9 that are already up regulated (treatment protocol) as well as to prevent their elevation (prevention protocol).

MMP-9 activity in sera was neither reported in SLE patients nor in animal models of SLE. This is the first time that a correlation between SLE and MMP-9 is shown and that MMP-9 is demonstrated to be elevated in sera and kidneys of SLE-afflicted mice. Although the elevation in sera appears relatively late (around 4 months after the boost), the elevation of MMP-9 in the kidneys is observed at early stages after disease induction (2 months) (data not shown). It is further shown herein for the first time that peptides that ameliorate SLE manifestations in mice (mCDR1 and hCDR1 as shown above), also down regulate MMP-9 both in sera and in kidneys. The latter data were also supported by preliminary results, using the MMP-9 activity assay system that showed that immunization with the 16/6Id elevated MMP-9 activity, whereas treatment with the CDR1-based peptide down regulated it to the activity levels of unimmunized mice.

It is also demonstrated here for the first time that MMP-3 and MMP-9 differ in the kinetics of their induction in experimental models of autoimmune diseases as shown here specifically for SLE. This may indicate the different roles of the above MMPs in the pathogenesis of the disease. Our results demonstrate that peptides that immunomodulate SLE-associated T-cell responses and down regulate disease manifestations can control the secretion (although not necessarily by the T cells themselves) of those MMPs in sera and kidneys. These results indicate that MMP-3 and MMP-9 play a role in the pathogenesis of SLE and may serve as surrogate markers of disease progression on one hand, and of disease amelioration by a given treatment, on the other hand.

Example 13

Activity of MMP-9 (but not of MMP-2) is Elevated in Sera of SLE Patients

In the present example, we determined the levels of MMP-9 and MMP-2 in sera of 40 patients with SLE and we demonstrate that MMP-9 but not MMP-2 activity is significantly elevated in sera of SLE patients compared to healthy controls. High MMP-9 activity correlated with the presence of discoid rash, Raynaud phenomenon, pneumonitis, mucosal ulcers and the presence of anti-phospholipid antibodies (APLA). In addition, elevated levels of MMP-9 correlated with SLE activity in the group of male patients.

Materials and Methods

Patients. Forty patients, 32 females and 8 males with SLE participated in this study. All patients revealed at least four of the revised diagnostic criteria of the American College of Rheumatism (ACR) for the diagnosis of SLE (Winchester, 1996). Twenty-five sex- and age-matched healthy volunteers served as a control group in our studies. The mean age of patients at diagnosis was 29±9.7 (range 15-48) years and the mean follow-up period was 11±10 (range 1-32) years. Disease activity was determined according to the SLEDAI lupus activity index (Bombardier et al., 1992) and by the BILAG index (Hay et al., 1993). The study was approved by the ethic committee of the Kaplan Medical Center, Rehovot, Israel.

Measurement of MMP-2 and MMP-9 by activity assay kits. Activities of MMP-2 and MMP-9 were measured by specific Biotrak MMP-2 or MMP-9 activity assay kits (Amersham Pharmacia Biotech UK Limited, UK) according to the manufacturer's instructions. Sera were diluted 1:100 and 1:32 for the determination of MMP-2 and MMP-9 activities, respectively. The appropriate standards were added in each assay. In order to measure the total content of the MMPs, activation of the pro form of the MMPs was performed using p-aminophenylmercuric acetate (APMA).

Measurement of MMP-2 and MMP-9 Activities by Gel Zymography. MMP-2 and MMP-9 activities were tested by gelatin zymography. A 5 μl sample of serum was separated by an 8% SDS-PAGE gel polymerized with 1 mg/ml gelatin. Gels were washed once for 30 min in 2.5% Triton X-100 to remove the SDS, and once for 30 min in the reaction buffer containing 50 mM Tris-HCl, 200 mM NaCl, 10 mM $CaCl_2$ and 0.02% (w/v) Brij 35 (pH 7.5). The reaction buffer was changed to a fresh one, and the gels were incubated at 37° C. for 24 h. Gelatinolytic activity was visualized by staining the gels with 0.5% Coomassie brilliant blue and was quantified by densitometry.

Statistical analyses. The data were evaluated using chi-square or Fisher exact tests, unpaired t-test and two tailed P-values. Pearson, Spearman and multivariate analyses were also used.

Example 13 (i)

Activity of MMP-9 but not of MMP-2 is Elevated in SLE

Figure 24:
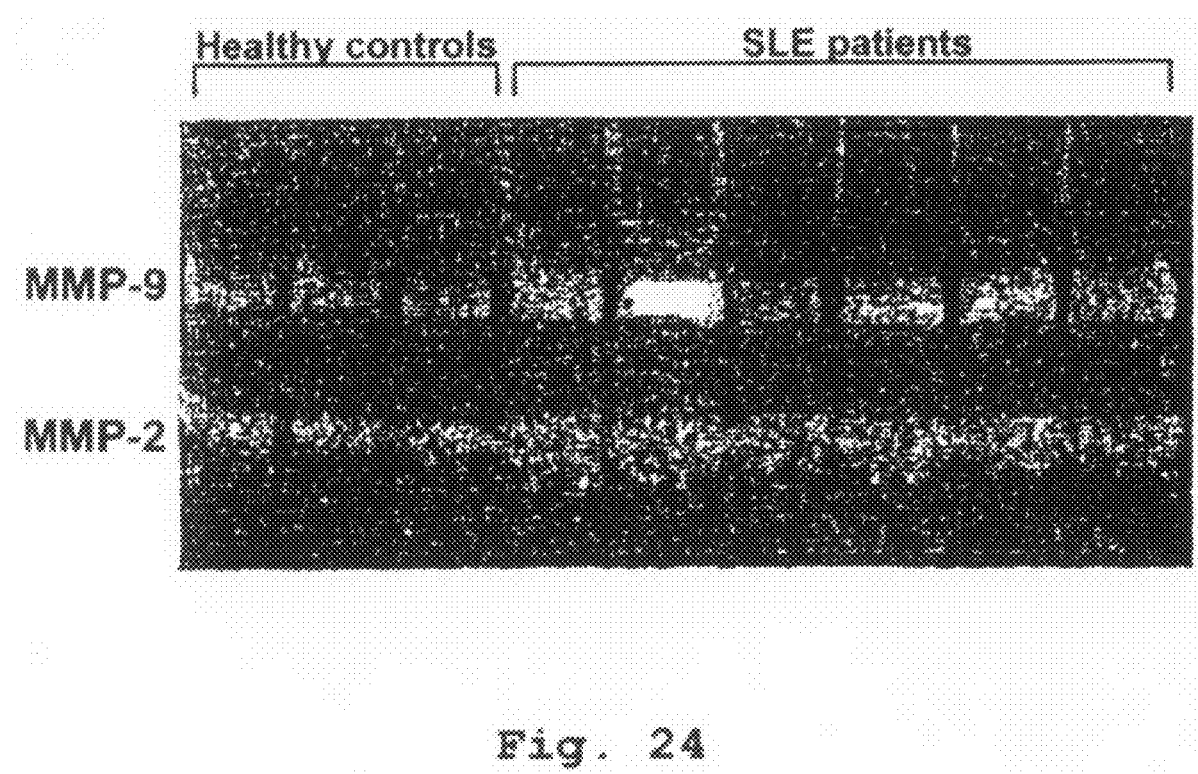
FIG. 24 depicts a representative gel showing activity of MMP-2 and MMP-9 in sera of SLE patients and healthy controls. Sera (5 μl) of 40 individual SLE patients and 25 healthy controls were analysed for their MMP-2 or MMP-9 activities by gel zymography. The figure shows representative results with serum samples of the two groups.

As described above, MMP-9 was shown to be involved in several autoimmune diseases as well as in animal models of SLE. Thus, we were interested in studying whether MMP-9 is also elevated in sera of SLE patients. For this purpose, we examined sera of 40 SLE patients and of 25 healthy controls by gel zymography, in which both MMP-9 and MMP-2 activities can be visualized. A representative gel is shown in FIG. 24. As can be seen in this figure, levels of MMP-9 are elevated in the sera of SLE patients when compared to healthy controls. Densitometric analysis of the zymograms of sera of 40 SLE patients and 25 healthy controls indicated that the mean MMP-9 activity for SLE patients was 109±5.6 densitometry units and for the healthy controls, 76.5±4.2 densitometry units (P=0.0001). Activity values of above 85 densitometry units (mean of healthy controls+2 s.e.) were considered high. The results demonstrated high activity levels of MMP-9 in 68% of the SLE patients. Only 3% of healthy controls exhibited high MMP-9 activity (P=0.001). Densitometric analysis of MMP-2 levels in the same serum samples revealed that the differences in MMP-2 activity between sera of SLE patients and of healthy controls were not significant. Thus values of 109±7 and of 123±5 (mean activity densitometry units±s.e.) were determined for healthy controls and SLE patients, respectively (P=0.0531). To quantify the activity levels of MMP-9 and MMP-2 in the serum further, we used activity assay kits.

Figure 25:
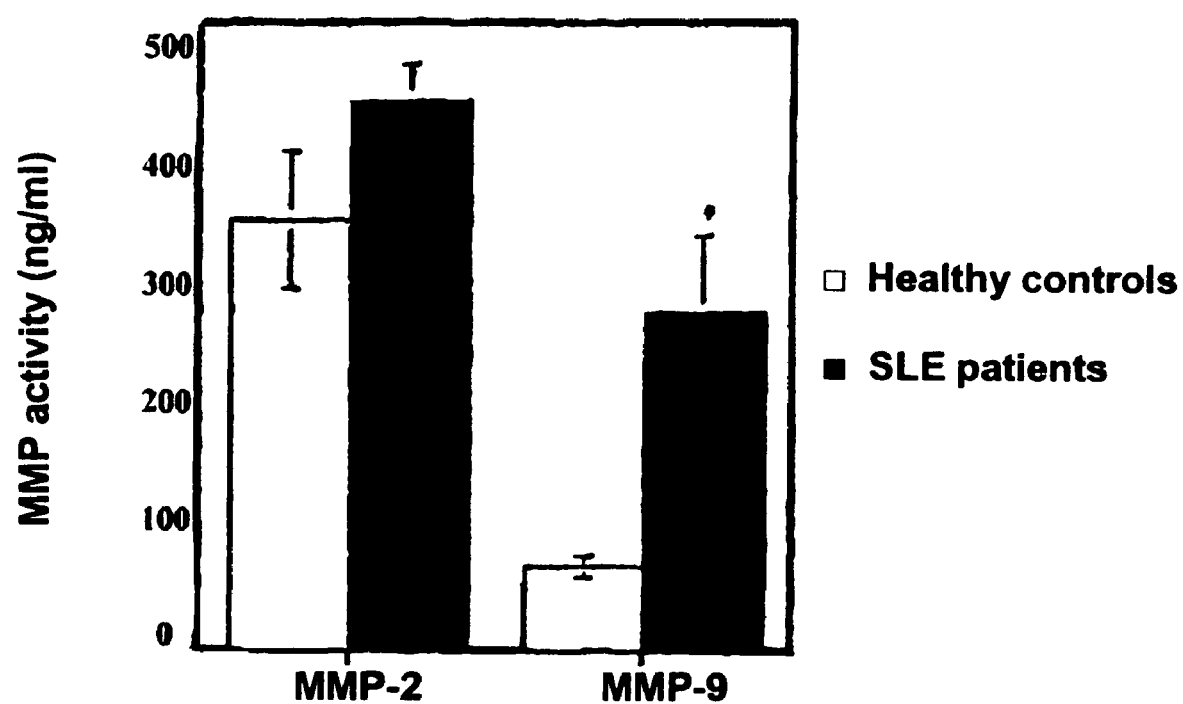
FIG. 25 depicts a graph showing quantitative analysis of MMP-2 and MMP-9 activities in sera of SLE patients (dark columns) and healthy controls (white columns). Thirty-six serum samples of SLE patients and 15 serum samples of healthy controls were tested for MMP-2 or MMP-9 activity using specific activity assay kits. Results are expressed as the mean±s.e.m.*P=0.0302.

FIG. 25 shows that the activity of MMP-9 is elevated by threefold in sera of SLE patients compared with sera of healthy controls, and this elevation is statistically significant (P=0.0302). In contrast, the differences in the levels of MMP-2 between the two groups are not significant (P=0.1254).

Since we, as well as others (Ebihara et al., 1998 and 1999) detected high MMP-9 levels in sera of patients with non-SLE chronic renal failure (e.g. diabetes mellitus, hypertension) probably due to the retention of the enzyme, we analysed the correlation between levels of MMP-9 and kidney function in the group of SLE patients tested. No correlation was observed between creatinine levels and MMP-9 levels ($r^2$=0.01), indicating that the elevated levels of MMP-9 in SLE patients were not the result of retention of the enzyme due to renal impairment.

Example 13(ii)

Correlation of MMP-9 Activity with Clinical and Laboratory Parameters

The elevation in the activity levels of MMP-9 in sera of SLE patients prompted us to look for possible correlation between clinical and laboratory parameters, and serum MMP-9 levels. Statistical analysis (chi-square or Fisher exact tests) was performed by investigating the number of patients with high and normal MMP-9 levels for each clinical manifestation (Table 15) as well as by taking into consideration the actual mean activity levels of MMP-9 for patients with or without a certain clinical symptom. The results were similar by both analyses. It is noteworthy that for all clinical symptoms, the percent of patients with elevated MMP-9 levels is much higher than that in the group of healthy controls. Levels of MMP-9 did not correlate with gender, duration of disease or the age of its onset (Pearson, Spearman).

Table 15 shows the clinical and laboratory characteristics of the SLE patients according to their MMP-9 activity levels (lower or equal to healthy controls=normal). High levels of MMP-9 correlated significantly with the presence of Raynaud phenomenon (P=0.0138) and APLA (P=0.041). A strong correlation could be observed with pneumonitis, discoid rash, neurological disorders and mucosal ulcers. However, the number of patients with the latter manifestations was too small to perform a statistical analysis. Multivariate analysis revealed that Raynaud phenomenon and low complement (C3, C4) levels are positively correlated with high MMP-9 levels (P=0.0001 and 0.0137, respectively). In contrast, photosensitivity, arthritis and hematological disorders are negatively correlated with MMP-9 activity levels (P=0.0381, 0.0014 and 0.0065, respectively).

TABLE 15

Clinical characteristics of SLE patients with high and normal MMP-9 activities according to their MMP-9 levels.

| | | | MMP-9 LEVELS (%) | |
| --- | --- | --- | --- | --- |
| | | | High | Normal |
| Number of Patients (%) | 40 | (100) | 27 (68) | 13 (32) |
| Photosensitivity | 13 | | 8 (62) | 5 (38) |
| Mucosal ulcers | 9 | | 8 (89) | 1 (11) |
| Malar rash | 9 | | 7 (78) | 2 (22) |
| Discoid rash | 5 | | 5 (100) | 0 (0) |
| Raynaud phenomenon | 8 | | 8 (100) | 0 (0) |
| Vasculitis | 18 | | 14 (78) | 4 (22) |
| Arthritis | 31 | | 21 (68) | 10 (32) |
| Serositis | 9 | | 7 (78) | 2 (22) |
| Pneumonitis | 4 | | 4 (100) | 0 (0) |
| Neurological disorders | 4 | | 4 (100) | 0 (0) |
| Renal disorder | 16 | | 11 (69) | 5 (31) |
| Hematological Disorders | 29 | | 18 (62) | 11 (38) |
| ANA | 40 | | 27 (68) | 13 (32) |
| αds-DNA | 36 | | 24 (67) | 12 (33) |
| APLA | 25 | | 20 (80) | 5 (20) |
| Low complement (C3, C4) | 30 | | 21 (70) | 9 (30) |

Clinical involvement was defined according to the ACR revised criteria (Winchester, 1996). Anti-nuclear antibodies (ANA) and anti-ds DNA antibodies were determined by using Hep2 cells and *Crithidia luciliae*, respectively. Anti-phospholipid antibodies (APLA) were defined as reactivity with one or more of the following assays: false positive VDR, lupus anti-coagulant (LAC) or ELISA for anticardiolipin antibodies.

Figure 26A:
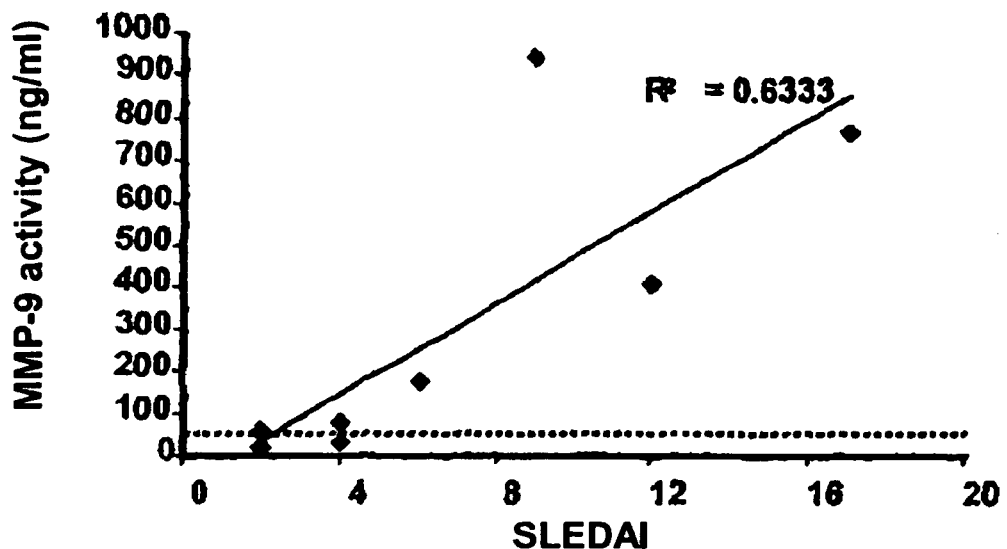
FIGS. 26A-26B are graphs showing MMP-9 activity levels and disease activity indices (SLEDAI) in patients with SLE. Thirty-five serum samples from 8 males (FIG. 26A) and 27 females (FIG. 26B) SLE patients were tested for MMP-9 activity by a specific activity assay kit. The distribution of MMP-9 activity according to the SLEDAI of the patients is presented. The dashed line represents the activity of MMP-9 in healthy controls.
Figure 26B:
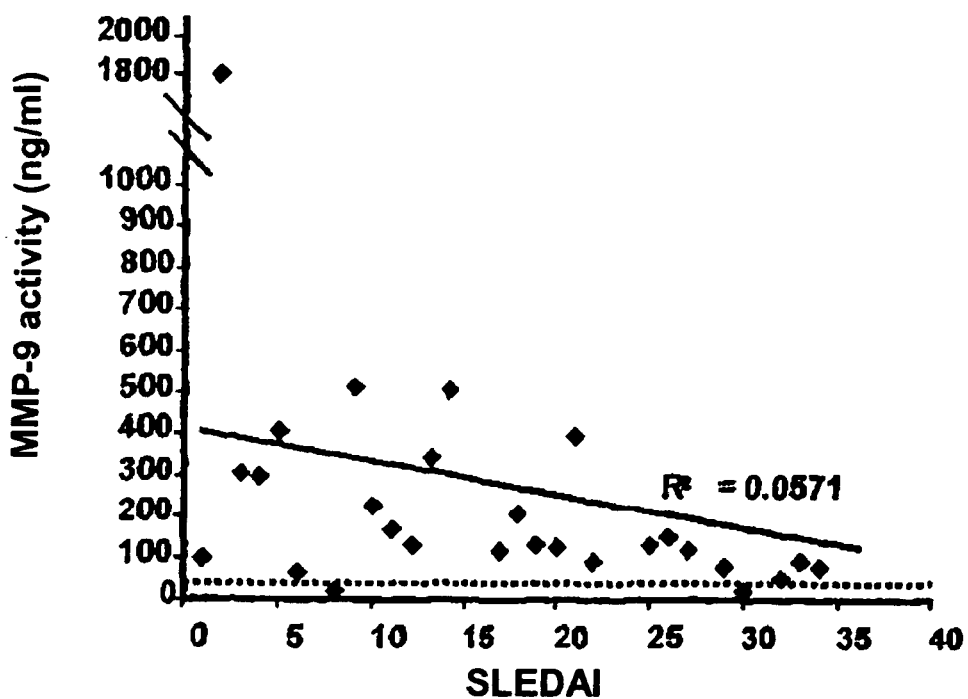

We also looked for a possible correlation between SLEDAI and MMP-9 activity in male (FIG. 26A) and female patients (FIG. 26B). Interestingly, the correlation coefficient was significant and positive for men ($r^2$=0.6333) but insignificant and negative for women ($r^2$=0.0571). Similar results were obtained using the BILAG scoring system. Thus, a positive correlation coefficient between MMP-9 activity and BILAG scores was observed for men ($r^2$=0.6442) and an insignificant one for women.

It was also of interest to determine whether a correlation exists between the use of various treatment modalities by the patients and MMP-9 activity. As can be seen in Table 16(A), there was no significant correlation between the current treatment of the patients and MMP-9 activity. However, when we looked at treatment of patients at any time during their disease course (Table 16(B)), high MMP-9 levels were associated with usage of cytotoxic agents (82%).

TABLE 16

Treatment modalities of SLE patients according to their MMP-9 levels.

| | Total Number of Patients | MMP-9 Levels (%) | |
|---|---|---|---|
| | | High | Normal |
| A. Current treatment. | | | |
| Cytotoxic agents | 8 | 6 (75) | 2 (25) |
| Steroids | 23 | 17 (74) | 6 (26) |
| Anti-Malarial | 21 | 14 (67) | 7 (33) |
| NSAID | 7 | 5 (71) | 2 (29) |
| B. Treatment along the follow up period. | | | |
| Cytotoxic agents | 17 | 14 (82) | 3 (18) |
| Steroids | 29 | 19 (66) | 10 (34) |
| Anti-Malarial | 26 | 16 (62) | 10 (38) |
| NSAID | 18 | 12 (67) | 6 (33) |

The anti-malarial agent hydroxychloroquine was used at dose of 200-400 mg/day. Steroid treatment was defined as a daily dose$\geq$5 mg of prednisone. Cytotoxic agents used were cyclophosphamide (0.5-1g/m$^2$ monthly) or azathioprine (100-150 mg/day).

Example 13(iii)

Figure 27A:
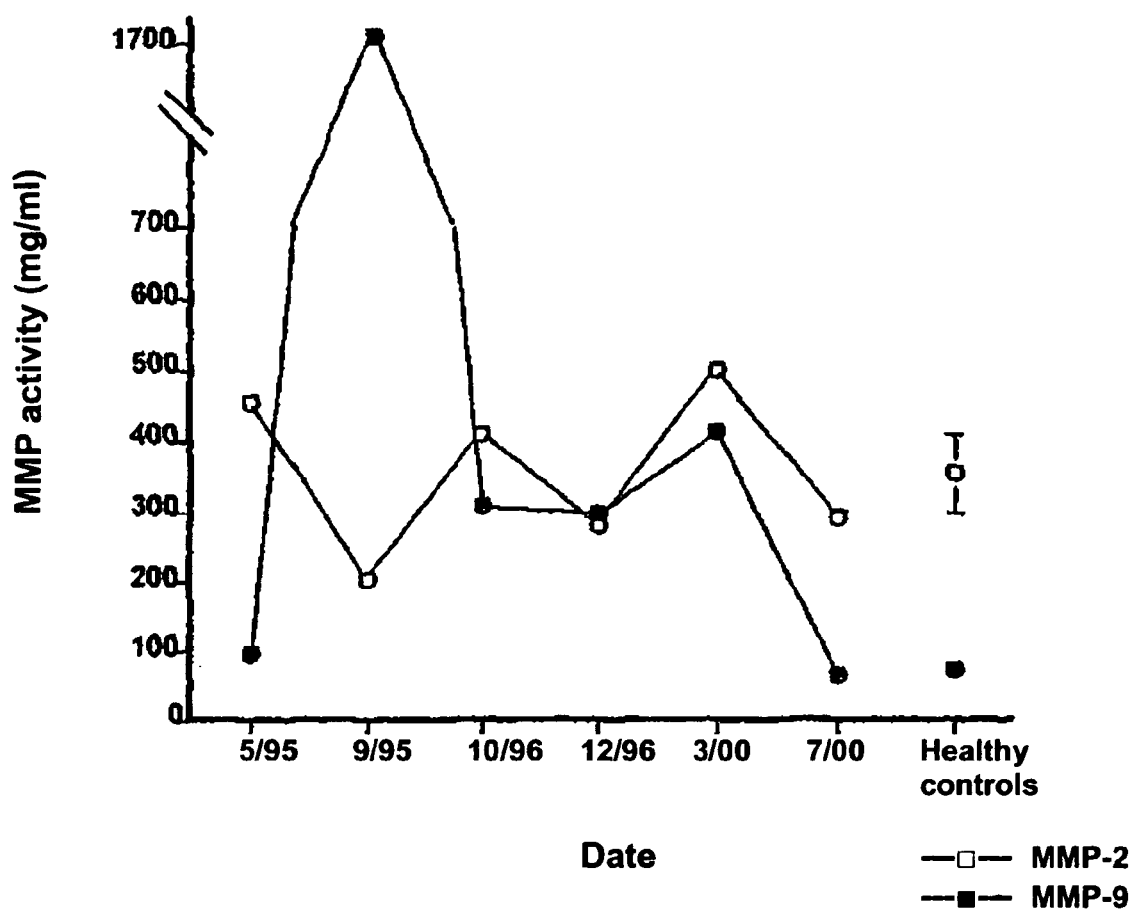
FIGS. 27A-27B are graphs showing pattern of MMP-2 (white circles) and MMP-9 (black circles) activities in sera of two SLE patients sampled during 4-6 years of disease. The sera were tested for MMP-2 or MMP-9 activities by specific activity assay kits. The assays were performed in duplicate.
Figure 27B:
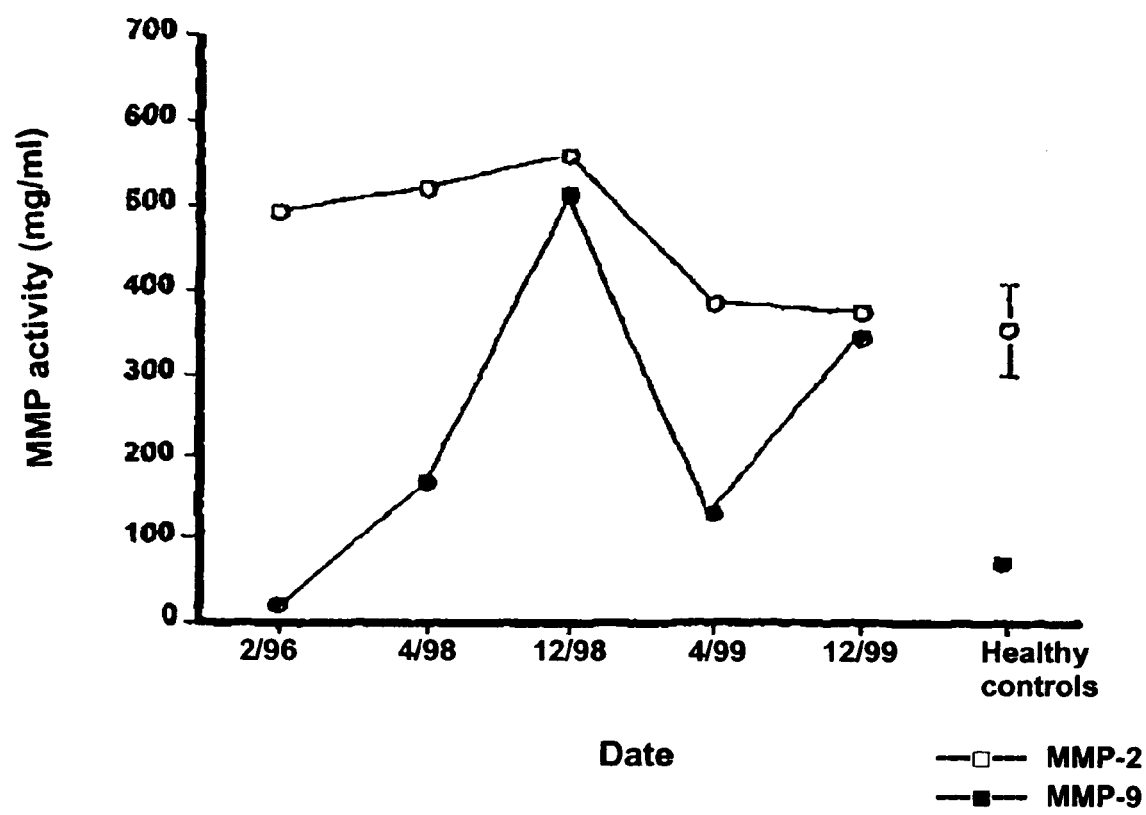

Variations in MMP-9 Activity in Serum Samples Taken from Individual SLE Patients at Different Time Points Since disease activity varies over time, we measured the activity levels of MMP-9 and MMP-2 in the serum of individual patients that were sampled during 4-6 years of follow-up. Sera of nine patients taken at different time points were analysed. Levels of MMP-2 did not vary significantly between patients and healthy controls. In 5 out of the 9 patients tested, variations in MMP-9 activity in serum samples of individual patients could be observed with time. The results for 2 representative SLE patients are shown in FIG. 27. As can be seen, MMP-9 activity, but not MMP-2 activity, has been changing with time in the same patients. These changes were not associated with disease activity indices as determined by either the SLEDAI or BILAG systems. Changes in MMP-9 activity were not detected in sera of 5 healthy controls that were sampled at different time points (data not shown). In 4 other SLE patients, no substantial changes in MMP-9 or MMP-2 activity were observed with time, and MMP-9 activity levels remained either high or low, depending on the individual patient.

Discussion

The present study demonstrates for the first time the involvement of MMP-9 in human SLE. We show that the activity of MMP-9, but not MMP-2, is significantly elevated in sera of 68% of SLE patients compared with healthy controls. High MMP-9 levels correlated with Raynaud phenomenon, pneumonitis, neurological disorders, discoid rash and the presence of APLA. Changes in MMP-9 activity were observed in serum of the same patient at different periods of the disease. MMP-9 activity levels did not correlate with disease activity index (SLEDAI, BILAG) in female patients, but correlated with SLE activity in the group of male patients.

The present study shows that activity levels of MMP-2 are not elevated significantly in sera of SLE patients. These results are compatible with those reported previously (Zucker, 1999) that MMP-2 levels were not increased in SLE. Levels of MMP-2 were also constitutive and unchanged in other pathological conditions (like optic neuritis and multiple sclerosis) in which levels of MMP-9 were elevated relatively to the healthy controls (Gijbels et al., 1992; Paemen et al., 1994).

Involvement of an additional MMP, namely, MMP-3 was suggested in the pathogenesis of SLE, since it was significantly increased in sera of patients with SLE (Kotajima et al., 1998). The frequency of SLE patients with elevated MMP-9 activity (68%) shown in the present example, resembles the frequencies reported (Kotajima et al., 1998) for high MMP-3 levels in SLE (76%) and in RA (82%) patients. Furthermore, the MMP-3 transcript was shown to increase significantly with the progression of nephritis in (NZB×NZW)F1 mice (Nakamura et al., 1993).

The origin of the elevated MMPs in sera of SLE patients is not known. MMP-9 has been shown to be secreted by peripheral blood cells such as T cells, neutrophils, and macrophages (for review, see Goetzl et al., 1996). The fact that no correlation was found between MMP-9 activity levels and the number of peripheral blood cells in the patients may suggest that MMP-9 was not secreted by peripheral blood immune cells but rather, by SLE-affected organs like kidneys or lungs/pleura. The observation that all SLE patients with pneumonitis exhibited high MMP-9 activity levels may suggest the diseased lung as a source of high MMP-9 levels. Moreover, the association between cytotoxic treatment, which represents the severity of SLE-related organ impairment, and high levels of MMP-9 in the sera may also support the notion that the diseased organs are the source of MMP-9 activity in SLE patients. Nevertheless, the possibility still exists that less peripheral blood lymphocytes secreted higher activity levels of MMP-9.

TNF-α and IL-1 were shown to play an important role in the pathogenesis of SLE both in the human disease (Dean et al., 2000) and in murine models (Segal et al., 1997; Theofilopoulos et al., 1999; Eilat et al., 2001). It has been shown in several systems that these cytokines induce MMP-9 production (Guedez et al., 1996), and thus, it is possible that the induction of the latter MMPs is part of the pathogenic effect of these cytokines in SLE. It has been reported that levels of MMP-9, that are secreted spontaneously by peripheral blood monocytes of healthy individuals, were upregulated upon exposure to TNF-α and IL-1β (Saren et al., 1996). In addition, MMPs of both T cells and macrophages facilitate secretion of TNF-α by cleavage of the membrane-bound form (Gearing et al., 1994). Thus, these examples demonstrate the mutual regulatory effects of MMP on the proinflammatory cytokines and vice versa. Nevertheless, the fact that in the sera of some of the patients the activity levels of MMP-9 remained within the normal range during the follow-up period, whereas high activity levels of MMP-9 were measured in the sera of most patients, may suggest the involvement of genetic factors in the regulation of the latter.

The results herein indicate that MMP-9 might play a role in the pathogenesis of SLE, and that measurement of plasma/serum activity levels of this metalloproteinase may provide important information when monitoring patients treated with drugs that interfere with MMP-9 activity.

REFERENCES

Bombardier C, Gladman D D, Urowitz M B et al. Derivation of the SLEDAI. A disease activity index for lupus patients. Arthritis Rheum 35:630-40 (1992).

Conway, J. G., J. A. Wakefield, R. H. Brown, B. E. Marron, L. Sekut, R. L. Clark, G. McGeechan, and K. M. Connolly. Inhibition of cartilage and bone destruction in adjuvant arthritis in the rat by a matrix metalloproteinase inhibitor. J. Exp. Med. 182, 449 (1995).

Creange, A., Sharshaor, T., Planchenault, T., Christov, C., Poron, F., Raphael, J-C. and Gherardi, R. K., Matrix metalloproteinase-9 is increased and correlates with severity in Guillain-Barre syndrome. Neurology 53:1683-1691 (1999).

Dayan, M., Segal, R., Sthoeger, Z., Waisman, A., Brosh, N., Elkayam, O., Eilat, E., Fridkin, M. and Mozes, E. Immune response of SLE patients to peptides based on the complementarity determining regions of a pathogenic anti-DNA monoclonal antibody. J. Clin. Immunol. 20, 187 (2000).

Dean G S, Tyrrell-Price J, Crawley E et al. Cytokines and systemic lupus erythematosus. Ann Rheum Dis 59:243-51 (2000).

Ebihara I, Nakamura T, Shimada N et al. Increased plasma metalloproteinase-9 concentrations precede development of microalbuminuria in non-insulin-dependent diabetes mellitus. Am J Kidney Dis 32:544-50 (1998).

Ebihara I, Nakamura T, Ushiyama C et al. Effect of oral adsorbent AST-120 on plasma metalloproteinase-9 and serum tissue inhibitor of metalloproteinase-1 concentrations in chronic renal failure. Nephron 83:169 (1999).

Eilat, E., Zinger, H., Nyska, A. and Mozes, E. Prevention of systemic lupus erythematosus-like disease in (NZB× NZW)F1 mice by treating with CDR1- and CDR3-based peptides of a pathogenic autoantibody. J. Clin. Immunol. 20, 268 (2000).

Eilat, E., Dayan, M., Zinger, H. and Mozes, E. The mechanism by which a peptide based on the complementarity determining region-1 of a pathogenic anti-DNA autoantibody ameliorates experimental SLE. Proc. Natl. Acad. Sci. U.S.A., 98, 1148 (2001).

Fricke, H., Offen, D., Mendlovic, S., Shoenfeld, Y., Bekimer, R., Sperling, J. and Mozes, E. Induction of experimental systemic lupus erythematosus in mice by immunization with a monoclonal anti-La autoantibody. Int. Immunol. 2, 225 (1990).

Fricke, H., Mendlovic, S., Blank, M., Shoenfeld, Y., Ben-Bassat, M. and Mozes, E. Idiotype specific T-cell lines inducing experimental systemic lupus erythematosus in mice. Immunology. 73, 421 (1991).

Gearing A J H, Beckett P, Christodoulou M et al. Processing of tumour necrosis factor alpha precursor by metalloproteinases. Nature 370:555-7 (1994).

Gijbels K, Masure S, Carton H et al. Gelatinase in the cerebrospinal fluid of patients with multiple sclerosis and other inflammatory neurological disorders. J Neuroimmunol 41:29-34 (1992).

Gijbels, K., R. E. Galardy, and L. Steinman. Reversal of experimental autoimmune encephalomyelitis with a hydroxamate inhibitor of matrix metalloproteinases. J. Clin. Invest. 94: 2177-82 (1994).

Goetzl, E. J., Banda, M. J. and Leppert, D., Matrix metalloproteinases in immunity. J. Immunol. 156:1-4 (1996).

Guedez, L., Lim, M. S. and Stetler-Stevenson, W. G., The role of metalloproteinases and their inhibitors in hematological disorders. Crit. Rev. Oncogenesis 7: 205-225 (1996).

Hay E M, Bacon P A, Gordon C et al. The BILAG index: a reliable and valid instrument for measuring clinical disease activity in systemic lupus erythematosus. Q J Med 86: 447-58 (1993).

Hughes, P. M., G. M. A. Wells, J. M. Clements, A. J. Gearing, E. J. Redford, M. Davies, K. J. Smith, R. A. Hughes, M. C. Brown, and K. M. Miller. Matrix metalloproteinase expression during experimental neuritis. Brain. 121, 481 (1998).

Isenberg, D. A., Shoenfeld, Y., Madaio, M. P., Rauch, J., Reichlin, M., Stollar, B. D. and Schwartz, R. S. Anti-DNA antibody idiotypes in systemic lupus erythematosus. Lancet. 2, 417 (1984).

Isenberg, D. A. and Collins, C. Detection of cross-reactive anti-DNA antibody idiotypes of renal tissue-bound immunoglobulins from lupus patients. J. Clin. Invest. 76, 287 (1985).

Keyszer, G., I. Lambiri, R. Nagel, C. Keysser, M. Keysser, E. Gromnica-hle, J. Franz, G. R. Burmester, and K. Jung. Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers. J. Rheumatol. 26, 251 (1999).

Kotajima, L., Aotsuka, S., Fujimani, M., Okawa-Takatsuji, M., Kinoshita, M., Sumiya, M. and Obata, K., Increased levels of matrix metalloproteinase-3 in sera from patients with active lupus nephritis. Clin. Exp. Rheum. 16:409-415 (1998).

Liu, Z., Shipley, J. M., Vu, T. H., Zhou, X., Diaz, L. A., Werb, Z. and Senior, R. M., Gelatinase B-deficient mice are resistant to experimental bullous Pemphigoid. J. Exp. Med. 188:475-482 (1998).

Massova, I., Kotra, L. P., Fridman, R. and Mobashery, S., Matrix metalloproteinases: structures, evolution and diversification. Faseb. J. 12: 1075-1095 (1998).

Mendlovic, S., Brocke, S., Shoenfeld, Y., Ben-Bassat, M., Meshorer, A., Bakimer, R. and Mozes, E. Induction of a systemic lupus erythematosus-like disease in mice by a common human anti-DNA idiotype. Proc. Natl. Acad. Sci. U.S.A. 85, 2260 (1988).

Mendlovic, S., Fricke, H., Shoenfeld, Y., and Mozes, E. The role of anti-idiotypic antibodies in the induction of experimental systemic lupus erythematosus in mice. Eur. J. Immunol. 19, 729 (1989).

Mozes, E., Dayan, M., Zisman, E., Brocke, S., Licht, A. and Pecht, I. Direct binding of a myasthenia gravis related epitope to MHC class II molecules on living murine antigen-presenting cells. EMBO J. 8, 4049 (1989)

Nakamura, T., I. Ebihara, S. Osada, T. Takahashi, M. Yamamoto, Y. Tomino, and H. Koide. Gene expression of metalloproteinases and their inhibitor in renal tissue of New Zealand Black/White F1 mice. Clin. Sci. 85: 295-301 (1993).

Ozenci, V., L. Rinaldi, N. Teleshova, D. Matusevicius, p. Kivisak, M. Kouwenhoven, and H. Link. Metalloproteinases and their tissue inhibitors in multiple sclerosis. J. Autoimmun. 12, 297 (1999).

Paemen, L., Olsson, T., Soderstrom, M., Van Damme, J. and Opdenakker, G., Evaluation of gelatinases and IL-6 in the cerebrospinal fluid of patients with optic neuritis, multiple sclerosis and other inflammatory neurological disease. Eur. J. Neurol. 1:55-63 (1994).

Saren P, Welgus H G, Kovanen P T. TNF-α and IL-1β selectively induce expression of 92-kDa gelatinase by human macrophages. J Immunol 157:4159-65 (1996).

Segal R, Bermas B L, Dayan M et al. Kinetics of cytokine production in experimental systemic lupus erythematosus: involvement of T helper cell 1/T helper cell 2-type cytokines in disease. J Immunol 158:3009-16 (1997).

Shingleton, W. D. Hodges, D. J., Brick, P. and Cawston, T. E., Collagenases: a key enzyme in collagen turnover. Biochem. Cell. Biol. 74:759-775 (1996).

Shoenfeld, Y., Isenberg, D. A., Rauch, J., Madaio, M. P., Stollar, B. D. and Schwartz, R. S. Idiotypic cross-reaction of monoclonal human lupus antibodies. J. Exp. Med. 158, 718 (1983).

Shoenfeld, Y., Hsu-Lin, S. C., Gabriels, J. E., Silberstein, L. E., Furie, B. C., Furie, B., Stollar, B. D. and Schwartz, R. S., Production of autoantibodies by human-human hybridomas. J. Clin. Invest. 70:205-208 (1982).

Sthoeger, Z. M., Tartakovsky, B., Bentwitch, Z. and Mozes, E. Monoclonal anticardiolipin antibodies derived from mice with experimental systemic lupus erythematosus: characterization and the induction of a secondary antiphospholipid syndrome. J. Clin. Immunol. 13, 127 (1993).

Tan E M, Cohen A S, F. F J, Talal N, Winchester R J. The 1982 revised criteria for the classification of systemic lupus erythematosus. Arthritis Rheum 25:1271-77 (1982)

Theofilopoulos A N, Lawson B R. Tumor necrosis factor and other cytokines in murine lupus. Ann Rheum Dis 58 suppl: 149-55 (1999).

Waisman, A. and Mozes, E. Variable region sequences of autoantibodies from mice with experimental systemic lupus erythematosus. Eur. J. Immunol. 23, 1566 (1993).

Waisman, A., Mendlovic, S., Ruiz, P. J., Zinger, H., Meshorer, A. and Mozes, E. The role of the 16/6Id idiotype network in the induction and manifestations of systemic lupus erythematosus. Int. Immunol. 5, 1293 (1993).

Waisman, A., Shoenfeld, Y., Blank, M., Ruiz, P. J. and Mozes, E. The pathogenic human monoclonal anti-DNA that induces experimental systemic lupus erythematosus in mice is encoded by a $V_H4$ gene segment. Int. Immunol. 7, 689 (1995).

Waisman, A., Ruiz, P. J., Israeli, E., Eilat, E. Konin-Waisman, S., Zinger, H., Dayan, M. and Mozes, E. Modulation of murine systemic lupus erythematosus with peptides based on complementarity determining regions of a pathogenic anti-DNA monoclonal antibody. Proc. Natl. Acad. Sci. U.S.A. 94, 4 620 (1997).

Wallace, G. R., R. A. Whiston, M. R. Stanford, G. M. A. Wells, A. J. H. Gearing, and J. M. Clements. The matrix metalloproteinase inhibitor BB-1101 prevents experimental autoimmune uveoretinitis (EAU). Clin. Exp. Immunol. 118, 364 1999).

Winchester R J. Systemic lupus erythematosus pathogenesis. In: Koopman W J, ed. Birmingham, Ala.: William and Wilkins, pp. 1361-91 (1996).

Zucker, S. Increased serum stromelysin-1 levels in systemic lupus erythematosus: lack of correlation with disease activity. J. Rheumatol. 26, 78 (1999).

```
                        SEQUENCE LISTING

<160> NUMBER OF SEQ ID NOS: 30

<210> SEQ ID NO 1
<211> LENGTH: 20
<212> TYPE: PRT
<213> ORGANISM: Murine

<400> SEQUENCE: 1

Thr Gly Tyr Tyr Met Gln Trp Val Lys Gln Ser Pro Glu Lys Ser Leu
1               5                   10                  15

Glu Trp Ile Gly
            20

<210> SEQ ID NO 2
<211> LENGTH: 20
<212> TYPE: PRT
<213> ORGANISM: Murine

<400> SEQUENCE: 2

Glu Ile Asn Pro Ser Thr Gly Gly Thr Thr Tyr Asn Gln Lys Phe Lys
1               5                   10                  15

Ala Lys Ala Thr
            20

<210> SEQ ID NO 3
<211> LENGTH: 20
<212> TYPE: PRT
<213> ORGANISM: Murine

<400> SEQUENCE: 3

Tyr Tyr Cys Ala Arg Phe Leu Trp Glu Pro Tyr Ala Met Asp Tyr Trp
1               5                   10                  15

Gly Gln Gly Ser
            20
```

-continued

```
<210> SEQ ID NO 4
<211> LENGTH: 19
<212> TYPE: PRT
<213> ORGANISM: Murine

<400> SEQUENCE: 4

Gly Tyr Asn Met Asn Trp Val Lys Gln Ser His Gly Lys Ser Leu Glu
1               5                   10                  15

Trp Ile Gly

<210> SEQ ID NO 5
<211> LENGTH: 17
<212> TYPE: PRT
<213> ORGANISM: Murine

<400> SEQUENCE: 5

Tyr Tyr Cys Ala Arg Ser Gly Arg Tyr Gly Asn Tyr Trp Gly Gln Thr
1               5                   10                  15

Leu

<210> SEQ ID NO 6
<211> LENGTH: 19
<212> TYPE: PRT
<213> ORGANISM: Human

<400> SEQUENCE: 6

Gly Tyr Tyr Trp Ser Trp Ile Arg Gln Pro Pro Gly Lys Gly Glu Glu
1               5                   10                  15

Trp Ile Gly

<210> SEQ ID NO 7
<211> LENGTH: 22
<212> TYPE: PRT
<213> ORGANISM: Human

<400> SEQUENCE: 7

Tyr Tyr Cys Ala Arg Gly Leu Leu Arg Gly Gly Trp Asn Asp Val Asp
1               5                   10                  15

Tyr Tyr Gly Met Asp Val
            20

<210> SEQ ID NO 8
<211> LENGTH: 7
<212> TYPE: PRT
<213> ORGANISM: Human

<400> SEQUENCE: 8

Phe Ser Gly Tyr Tyr Trp Ser
1               5

<210> SEQ ID NO 9
<211> LENGTH: 16
<212> TYPE: PRT
<213> ORGANISM: Human

<400> SEQUENCE: 9

Glu Ile Asn His Ser Gly Ser Thr Asn Tyr Lys Thr Ser Leu Lys Ser
1               5                   10                  15

<210> SEQ ID NO 10
<211> LENGTH: 18
<212> TYPE: PRT
<213> ORGANISM: Human
```

```
<400> SEQUENCE: 10

Gly Leu Leu Arg Gly Gly Trp Asn Asp Val Asp Tyr Tyr Gly Met
1               5                   10                  15

Asp Val

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide based on the CDR1 of the
      heavy chain of human 16/6id mAb. Note:Thr (position 1) may be
      missing.
<220> FEATURE:
<221> NAME/KEY: MISC_FEATURE
<222> LOCATION: (1)..(20)
<223> OTHER INFORMATION: Xaa in position 9 is Arg or Lys; Xaa in
      position 11 is Pro or Ser; Xaa in position 13 is Gly or Glu; Xaa
      in position 14 is Lys or Asp; Xaa in position 16 is Glu, Leu or
      Ser.

<400> SEQUENCE: 11

Thr Gly Tyr Tyr Trp Ser Trp Ile Xaa Gln Xaa Pro Xaa Xaa Gly Xaa
1               5                   10                  15

Glu Trp Ile Gly
            20

<210> SEQ ID NO 12
<211> LENGTH: 19
<212> TYPE: PRT
<213> ORGANISM: Artificial Sequence
<220> FEATURE:
<223> OTHER INFORMATION: Synthetic. Note: a peptide of SEQ ID NO:11
      wherein Thr (position 1) is missing, Xaa(9) is Arg, Xaa(11) is
      Pro, Xaa(13) is Gly, Xaa(14) is Lys, and Xaa(16) is Leu.

<400> SEQUENCE: 12

Gly Tyr Tyr Trp Ser Trp Ile Arg Gln Pro Pro Gly Lys Gly Leu Glu
1               5                   10                  15

Trp Ile Gly

<210> SEQ ID NO 13
<211> LENGTH: 19
<212> TYPE: PRT
<213> ORGANISM: Artificial Sequence
<220> FEATURE:
<223> OTHER INFORMATION: Synthetic. Note: a peptide of SEQ ID NO: 11
      wherein Thr (position 1) is missing, Xaa(9) is Arg, Xaa(11) is
      Pro, Xaa(13) is Gly, Xaa(14) is Lys, and Xaa(16) is Ser.

<400> SEQUENCE: 13

Gly Tyr Tyr Trp Ser Trp Ile Arg Gln Pro Pro Gly Lys Gly Ser Glu
1               5                   10                  15

Trp Ile Gly

<210> SEQ ID NO 14
<211> LENGTH: 19
<212> TYPE: PRT
<213> ORGANISM: Artificial sequence
<220> FEATURE:
<223> OTHER INFORMATION: Synthetic. Note: a peptide of SEQ ID NO: 11
      wherein Thr (position 1) is missing, Xaa(9) is Arg, Xaa(11) is
      Pro, Xaa(13) is Gly, Xaa(14) is Asp, and Xaa(16) is Glu.
```

```
<400> SEQUENCE: 14

Gly Tyr Tyr Trp Ser Trp Ile Arg Gln Pro Pro Gly Asp Gly Glu Glu
1               5                   10                  15

Trp Ile Gly

<210> SEQ ID NO 15
<211> LENGTH: 19
<212> TYPE: PRT
<213> ORGANISM: Artificial Sequence
<220> FEATURE:
<223> OTHER INFORMATION: Synthetic. Note: a peptide of SEQ ID NO: 11
      wherein Thr (position 1) is missing, Xaa(9) is Lys, Xaa(11) is
      Pro, Xaa(13) is Gly, Xaa(14) is Lys, and Xaa(16) is Glu.

<400> SEQUENCE: 15

Gly Tyr Tyr Trp Ser Trp Ile Lys Gln Pro Pro Gly Lys Gly Glu Glu
1               5                   10                  15

Trp Ile Gly

<210> SEQ ID NO 16
<211> LENGTH: 19
<212> TYPE: PRT
<213> ORGANISM: Artificial Sequence
<220> FEATURE:
<223> OTHER INFORMATION: Synthetic. Note: a peptide of SEQ ID NO: 11
      wherein Thr (position 1) is missing, Xaa(9) is Arg, Xaa(11) is
      Ser, Xaa(13) is Gly, Xaa(14) is Lys, and Xaa(16) is Glu.

<400> SEQUENCE: 16

Gly Tyr Tyr Trp Ser Trp Ile Arg Gln Ser Pro Gly Lys Gly Glu Glu
1               5                   10                  15

Trp Ile Gly

<210> SEQ ID NO 17
<211> LENGTH: 19
<212> TYPE: PRT
<213> ORGANISM: Artificial Sequence
<220> FEATURE:
<223> OTHER INFORMATION: Synthetic. Note: a peptide of SEQ ID NO:11
      wherein Thr (position 1) is missing, Xaa(9) is Arg, Xaa(11) is
      Pro, Xaa(13) is Glu, Xaa(14) is Lys, and Xaa(16) is Glu.

<400> SEQUENCE: 17

Gly Tyr Tyr Trp Ser Trp Ile Arg Gln Pro Pro Glu Lys Gly Glu Glu
1               5                   10                  15

Trp Ile Gly

<210> SEQ ID NO 18
<211> LENGTH: 20
<212> TYPE: PRT
<213> ORGANISM: Artificial Sequence
<220> FEATURE:
<223> OTHER INFORMATION: Synthetic. Note: a peptide of SEQ ID NO: 11
      wherein Xaa(9) is Arg, Xaa(11) is Pro, Xaa(13) is Gly, Xaa(14)
      is Lys, and Xaa(16) is Glu.

<400> SEQUENCE: 18

Thr Gly Tyr Tyr Trp Ser Trp Ile Arg Gln Pro Pro Gly Lys Gly Glu
1               5                   10                  15

Glu Trp Ile Gly
            20
```

```
<210> SEQ ID NO 19
<211> LENGTH: 22
<212> TYPE: PRT
<213> ORGANISM: Artificial Sequence
<220> FEATURE:
<223> OTHER INFORMATION: Synthetic peptide based on CDR3 of the heavy
      chain of human 16/6id mAb.
<220> FEATURE:
<221> NAME/KEY: MISC_FEATURE
<222> LOCATION: (1)..(22)
<223> OTHER INFORMATION: Xaa in position 6 is Gly or Phe; Xaa in
      position 9 is Arg or Ala; Xaa in position 10 is Gly or Ala; Xaa
      in position 11 is Gly or Ala; Xaa in position 12 is Trp or Ala;
      Xaa in position 13 is Asn or Ala; Xaa in position 18 is Tyr or
      Trp; Xaa in position 20 is Met or Gln.

<400> SEQUENCE: 19

Tyr Tyr Cys Ala Arg Xaa Leu Leu Xaa Xaa Xaa Xaa Xaa Asp Val Asp
1               5                   10                  15

Tyr Xaa Gly Xaa Asp Val
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Arg, Xaa(10) is Gly, Xaa(11)
      is Gly, Xaa(12) is Trp, Xaa(13) is Ala, Xaa(18) is Tyr, and
      Xaa(20) is Met.

<400> SEQUENCE: 20

Tyr Tyr Cys Ala Arg Gly Leu Leu Arg Gly Gly Trp Ala Asp Val Asp
1               5                   10                  15

Tyr Tyr Gly Met Asp Val
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Arg, Xaa(10) is Gly, Xaa(11) is
      Gly, Xaa(12) is Ala, Xaa(13) is Asn, Xaa(18) is Tyr, and Xaa(20)
      is Met.

<400> SEQUENCE: 21

Tyr Tyr Cys Ala Arg Gly Leu Leu Arg Gly Gly Ala Asn Asp Val Asp
1               5                   10                  15

Tyr Tyr Gly Met Asp Val
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Arg, Xaa(10) is Gly, Xaa(11) is
      Ala, Xaa(12) is Trp, Xaa(13) is Asn, Xaa(18) is Tyr, and Xaa(20)
      is Met.
```

<400> SEQUENCE: 22

Tyr Tyr Cys Ala Arg Gly Leu Leu Arg Gly Ala Trp Asn Asp Val Asp
1               5                   10                  15

Tyr Tyr Gly Met Asp Val
            20

<210> SEQ ID NO 23
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Arg, Xaa(10) is Ala, Xaa(11) is
      Gly, Xaa(12) is Trp, Xaa(13) is Asn, Xaa(18) is Tyr, and Xaa(20)
      is Met.

<400> SEQUENCE: 23

Tyr Tyr Cys Ala Arg Gly Leu Leu Arg Ala Gly Trp Asn Asp Val Asp
1               5                   10                  15

Tyr Tyr Gly Met Asp Val
            20

<210> SEQ ID NO 24
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Ala, Xaa(10) is Gly, Xaa(11) is
      Gly, Xaa(12) is Trp, Xaa(13) is Asn, Xaa(18) is Tyr, and Xaa(20)
      is Met.

<400> SEQUENCE: 24

Tyr Tyr Cys Ala Arg Gly Leu Leu Ala Gly Gly Trp Asn Asp Val Asp
1               5                   10                  15

Tyr Tyr Gly Met Asp Val
            20

<210> SEQ ID NO 25
<211> LENGTH: 22
<212> TYPE: PRT
<213> ORGANISM: Artificial Sequence
<220> FEATURE:
<223> OTHER INFORMATION: Sunthetic. Note: a peptide of SEQ ID NO:19
      wherein Xaa(6) is Phe, Xaa(9) is Arg, Xaa(10) is Gly, Xaa(11) is
      Gly, Xaa(12) is Trp, Xaa(13) is Asn, Xaa(18) is Tyr, and Xaa(20)
      is Met.

<400> SEQUENCE: 25

Tyr Tyr Cys Ala Arg Phe Leu Leu Arg Gly Gly Trp Asn Asp Val Asp
1               5                   10                  15

Tyr Tyr Gly Met Asp Val
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Arg, Xaa(10) is Gly, Xaa(11) is
      Gly, Xaa(12) is Trp, Xaa(13) is Asn, Xaa(18) is Tyr, and Xaa(20)
      is Gln.

```
<400> SEQUENCE: 26

Tyr Tyr Cys Ala Arg Gly Leu Leu Arg Gly Gly Trp Asn Asp Val Asp
1               5                   10                  15

Tyr Tyr Gly Gln Asp Val
            20

<210> SEQ ID NO 27
<211> LENGTH: 22
<212> TYPE: PRT
<213> ORGANISM: Artificial Sequence
<220> FEATURE:
<223> OTHER INFORMATION: Synthetic. Note: a peptide of SEQ ID NO:19
      wherein Xaa(6) is Gly, Xaa(9) is Arg, Xaa(10) is Gly, Xaa(11) is
      Gly, Xaa(12) isTrp, Xaa(13) is Asn, Xaa(18) is Trp, and Xaa(20)
      is Met.

<400> SEQUENCE: 27

Tyr Tyr Cys Ala Arg Gly Leu Leu Arg Gly Gly Trp Asn Asp Val Asp
1               5                   10                  15

Tyr Trp Gly Met Asp Val
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide prepared in the reversed
      order of SEQ ID NO: 1.

<400> SEQUENCE: 28

Gly Ile Trp Glu Leu Ser Lys Glu Pro Ser Gln Lys Val Trp Gln Met
1               5                   10                  15

Tyr Tyr Gly Thr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide prepared in reversed order
      of SEQ ID NO: 3.

<400> SEQUENCE: 29

Ser Gly Gln Gly Trp Tyr Asp Met Ala Tyr Pro Glu Trp Leu Phe Arg
1               5                   10                  15

Ala Cys Tyr Tyr
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic peptide prepared in the reversed
      order of SEQ ID NO: 6.

<400> SEQUENCE: 30

Gly Ile Trp Glu Glu Gly Lys Gly Pro Pro Gln Arg Ile Trp Ser Trp
1               5                   10                  15

Tyr Tyr Gly
```

The invention claimed is:

1. A compound selected from the group consisting of:
   (a) a peptide the amino acid sequence of which is set forth in SEQ ID NO: 6 or SEQ ID NO: 7;
   (b) a salt of the peptide of (a);
   (c) a peptide the amino acid sequence of which is set forth in SEQ ID NO: 6 or SEQ ID NO: 7 and the carboxyl group at the C-terminus of which is amidated;
   (d) a salt of the peptide of (c);
   (e) a peptide consisting of amino acids whose sequence is set forth in SEQ ID NO: 6 covalently linked directly to amino acids whose sequence is set forth in SEQ ID NO: 7;
   (f) a peptide comprising two peptides the amino acid sequence of each of which is set forth in SEQ ID NO: 6, covalently linked by peptide bond to one another either directly or through a short linking chain;
   (g) a peptide comprising two peptides the amino acid sequence of each of which is set forth in SEQ ID NO: 7, covalently linked by peptide bond to one another either directly or through a short linking chain;
   (h) a salt of the peptide of (e), (f) or (g); and
   (i) a peptide of (a), (c), (e), (f) or (g), or a salt of (b), (d) or (h), attached to a macromolecular carrier.

2. The compound according to claim 1, selected from the group consisting of:
   (a) a peptide the amino acid sequence of which is set forth in SEQ ID NO: 6;
   (b) a salt of the peptide of (a);
   (c) a peptide the amino acid sequence of which is set forth in SEQ ID NO: 6 and the carboxyl group at the C-terminus of which is amidated;
   (d) a salt of the peptide of (c);
   (e) a peptide comprising two peptides of (a), covalently linked by peptide bond to one another either directly or through a short linking chain;
   (f) a salt of the peptide of (e); and
   (g) a peptide of (a), (c) or (e), or a salt of (b), (d) or (f), attached to a macromolecular carrier.

3. The compound according to claim 2, which is the peptide the amino acid sequence of which is set forth in SEQ ID NO: 6.

4. A compound selected from the group consisting of:
   (a) a peptide the amino acid sequence of which is set forth in SEQ ID NO: 6;
   (b) a salt of the peptide of (a);
   (c) a peptide the amino acid sequence of which is set forth in SEQ ID NO: 6 and the carboxyl group at the C-terminus of which is amidated; and
   (d) a salt of the peptide of (c).

5. The compound according to claim 1, selected from the group consisting of:
   (a) a peptide the amino acid sequence of which is set forth in SEQ ID NO: 7;
   (b) a salt of the peptide of (a);
   (c) a peptide the amino acid sequence of which is set forth in SEQ ID NO: 7 and the carboxyl group at the C-terminus of which is amidated;
   (d) a salt of the peptide of (c);
   (e) a peptide comprising two peptides of (a), covalently linked by peptide bond to one another either directly or through a short linking chain;
   (f) a salt of the peptide of (e); and
   (g) a peptide of (a), (c) or (e), or a salt of (b), (d) or (f), attached to a macromolecular carrier.

6. The compound according to claim 5, which is the peptide the amino acid sequence of which is set forth in SEQ ID NO: 7.

7. A compound selected from the group consisting of:
   (a) a peptide the amino acid sequence of which is set forth in SEQ ID NO: 7;
   (b) a salt of the peptide of (a);
   (c) a peptide the amino acid sequence of which is set forth in SEQ ID NO: 7 and the carboxyl group at the C-terminus of which is amidated; and
   (d) a salt of the peptide of (c).

8. The compound according to claim 1, which is the peptide consisting of consecutive amino acids, the sequence of which is set forth in SEQ ID NO:6, covalently linked directly to consecutive amino acids, the sequence of which is set forth in SEQ ID NO:7.

9. A pharmaceutical composition comprising a pharmaceutically acceptable carrier and the compound according to claim 1.

10. The pharmaceutical composition according to claim 9, wherein the compound is a peptide selected from the group consisting of:
    (a) a peptide the amino acid sequence of which is set forth in SEQ ID NO: 6 or SEQ ID NO: 7;
    (b) a salt of the peptide of (a);
    (c) a peptide the amino acid sequence of which is set forth in SEQ ID NO: 6 or SEQ ID NO: 7 and the carboxyl group at the C-terminus of which is amidated; and
    (d) a salt of the peptide of (c).

11. The pharmaceutical composition according to claim 10, for the treatment of systemic lupus erythematosus.

12. The pharmaceutical composition according to claim 11, adapted for oral, intravenous, subcutaneous, intraarticular, intramuscular, inhalation, intranasal, intrathecal, intraperitoneal, intradermal, transdermal or enteral administration.

13. A method of treatment of systemic lupus erythematosus (SLE) comprising administering to a SLE patient an effective amount of the compound according to claim 1.

14. The method according to claim 13, which comprises administering to the SLE patient an effective amount of the peptide of the SEQ ID NO: 6.

15. The method according to claim 13, which comprises administering to the SLE patient an effective amount of the peptide of the SEQ ID NO: 7.

16. A method for immunomodulation of systemic lupus erythematosus (SLE)-associated responses in a SLE patient, which comprises administering to said SLE patient an effective amount of the compound according to claim 1.

17. The method according to claim 16, which comprises down-regulating the levels of matrix metalloproteinase (MMP)-3 and/or MMP-9 activities in the SLE patient.

18. The method according to claim 16, which comprises immunomodulating the level of a cytokine activity in the SLE patient.

19. The method according to claim 18, which comprises down-regulating the level of IL-2 and/or IFN-γ activity in the SLE patient.

20. The method according to claim 18, which comprises up-regulating the level of TGF-β activity in the SLE patient.

21. The method according to claim 16, which comprises administering to the SLE patient an effective amount of the peptide of the SEQ ID NO: 6.

22. The method according to claim 16, which comprises administering to the SLE patient an effective amount of the peptide of the SEQ ID NO: 7.

* * * * *